United States Patent
Sakai et al.

(10) Patent No.: US 7,507,207 B2
(45) Date of Patent: Mar. 24, 2009

(54) PORTABLE BIOLOGICAL INFORMATION MONITOR APPARATUS AND INFORMATION MANAGEMENT APPARATUS

(75) Inventors: Kazuhiro Sakai, Anjo (JP); Teiyuu Kimura, Nagoya (JP); Katsuyoshi Nishii, Okazaki (JP); Kazuya Inokawa, Obu (JP); Tetsuya Nakashima, Ichinomiya (JP)

(73) Assignee: DENSO CORPORATION, Kariya (JP)

( * ) Notice: Subject to any disclaimer, the term of this patent is extended or adjusted under 35 U.S.C. 154(b) by 536 days.

(21) Appl. No.: 10/957,663

(22) Filed: Oct. 5, 2004

(65) Prior Publication Data

US 2005/0075553 A1   Apr. 7, 2005

(30) Foreign Application Priority Data

| Oct. 7, 2003 | (JP) | ............................. 2003-348445 |
| Dec. 1, 2003 | (JP) | ............................. 2003-401927 |
| Dec. 1, 2003 | (JP) | ............................. 2003-401928 |

(51) Int. Cl.
*A61B 5/00* (2006.01)
(52) U.S. Cl. ........................ 600/485; 600/300; 600/500
(58) Field of Classification Search ................ 600/300, 600/301, 481, 485, 490, 500
See application file for complete search history.

(56) References Cited

U.S. PATENT DOCUMENTS

| 5,197,489 | A | * | 3/1993 | Conlan ........................ 600/595 |
| 5,313,940 | A | * | 5/1994 | Fuse et al. ................... 600/310 |
| 5,697,374 | A | | 12/1997 | Odagiri et al. |
| 5,781,511 | A | * | 7/1998 | Yasukawa et al. .............. 368/11 |
| 5,782,757 | A | * | 7/1998 | Diab et al. ................... 600/323 |
| 5,807,267 | A | * | 9/1998 | Bryars et al. ................. 600/500 |
| 6,022,321 | A | * | 2/2000 | Amano et al. ................ 600/500 |
| 6,212,427 | B1 | * | 4/2001 | Hoover ........................ 600/515 |
| 6,241,684 | B1 | | 6/2001 | Amano et al. |
| 6,714,811 | B1 | * | 3/2004 | Padmanabhan et al. ...... 600/509 |

FOREIGN PATENT DOCUMENTS

| JP | A-09-294727 | 11/1997 |
| JP | A-11-34688 | 2/1999 |

(Continued)

OTHER PUBLICATIONS

Notice of reason of rejection from Japan Patent Office dated Apr. 10, 2007 (English translation thereof) in a corresponding Japanese patent application No. 2003-348445.

*Primary Examiner*—Robert L Nasser
(74) *Attorney, Agent, or Firm*—Posz Law Group, PLC

(57) ABSTRACT

In a portable biological information monitor apparatus, a pulse wave detection signal obtained by light emission from a green LED and a body motion detection signal obtained by light emission from an infrared LED are detected as biological information. This biological information is analyzed to compute various barometers. In a wake normal mode of a set generation mode, body motion and pulse are calculated as wake evaluation barometers for evaluation of a test subject's status in wake. In a wake steady state motion mode, body motion, pulse, and pitch are calculated as motion evaluation barometers for evaluation of the test subject's status in steady state motion. In a sleep mode, body motion, pulse, and autonomic nervous function are calculated as sleep evaluation barometers for evaluation of the test subject's status in sleep. Necessary barometers are thereby generated regardless of the test subject's action using the portable monitor apparatus alone.

53 Claims, 30 Drawing Sheets

FOREIGN PATENT DOCUMENTS

| | | |
|---|---|---|
| JP | A-11-299740 | 11/1999 |
| JP | A-2001-112725 | 4/2001 |
| JP | A-2002-330935 | 11/2002 |
| JP | A-2003-052649 | 2/2003 |
| JP | B2-2950038 | 7/2004 |

* cited by examiner

PORTABLE BIOLOGICAL INFORMATION MONITOR APPARATUS AND INFORMATION MANAGEMENT APPARATUS

CROSS REFERENCE TO RELATED APPLICATIONS

This application is based on and incorporates herein by reference Japanese Patent Applications No. 2003-348445 filed on Oct. 7, 2003, No. 2003-401927 filed on Dec. 1, 2003, and No. 2003-401928 filed on Dec. 1, 2003.

FIELD OF THE INVENTION

The present invention relates to a portable biological information monitor apparatus used in a status where it is attached to a test subject's body, and to an information management apparatus to process and display information generated by the monitor apparatus.

BACKGROUND OF THE INVENTION

Conventionally, detection of biological information such as electroencephalogram, body motion, heart beat and respiration, and evaluation of activities (activity amount during waking hours) and sleep based on the result of detection have been proposed.

As an apparatus of this type, a sleep evaluation apparatus is known (for example, see JP2950038 B2). This sleep evaluation apparatus detects biological information in sleeping hours by using piezoelectric devices and an encephalograph integrated with bedding, and evaluates the quality of sleep from the result of detection. Further, another apparatus is known (for example, see JP2816944 B2 (U.S. Pat. No. 5,697,374). This apparatus detects an electroencephalogram from a piezoelectric microphone attached to a finger tip and at the same time detects body motion from an acceleration sensor attached to a belt or the like; then the apparatus obtains a pulse rate and motion pitch from the result of detection for evaluation of exercise intensity or the like.

However, these apparatuses are used for measurement and evaluation of limited actions such as exercise and sleeping but are not used for comprehensive evaluation of test subject's status.

To have a good sleep, sufficient activities and appropriate fatigue in day times are necessary. A person who suffers from a sleep abnormality such as an insomniac, abnormally awakes at night and abnormally feels drowsy in the day time. That is, daytime activities (degree of wake and momentum) are closely related to sleeping. Accordingly, sufficient information cannot be obtained from some limited actions, so that accurate evaluation and advice cannot be made.

Further, when different apparatuses are used for measurement of biological information on various actions, attachment and removal of the apparatuses is very troublesome. Especially, in the case of measurement of electroencephalogram as in the above-described sleep evaluation apparatus, since the test subject's actions are limited by electrodes attached to the test subject's body and a cable connected to the apparatus main body, biological information in normal living conditions cannot be obtained without difficulty.

SUMMARY OF THE INVENTION

To solve the above problems, it is an object of the present invention to provide a portable biological information monitor apparatus which always monitors biological information without attachment and removal of apparatuses, and an information management apparatus which processes and displays information generated by the monitor apparatus.

In the portable biological information monitor apparatus according to the present invention made to attain the above object, biological information detection means repeatedly detects a test subject's biological information reflecting pulse, body motion, and autonomic nervous system function. Then, barometer generation means includes multiple generation modes corresponding to the test subject's actions and operates in any of generation modes based on the detected biological information. Here, the generation modes include at least a first generation mode to generate sleep evaluation barometers for evaluation of the test subject's status in sleep and a second generation mode to generate wake evaluation barometers for evaluation of the test subject's status in wake. Storage means stores the generated barometers. "Barometer" is used to mean an "indicator.

In this manner, the portable biological information monitor apparatus according to the present invention, as a single apparatus, monitors biological information in sleep and biological information in wake. Then, a comprehensive evaluation of the test subject's status (e.g., life rhythm, activity amount (consumed calories), physical condition, and sleep quality) can be made based on sleep evaluation barometers and wake evaluation barometers generated from these pieces of biological information. Further, accurate advice can be dispensed to the test subject based on the result of evaluation.

Further, according to the present invention, as barometers for evaluation of different actions (sleep evaluation barometers and wake evaluation barometers) are generated from the same biological information, attachment and removal of apparatuses by action is not necessary. Further, as the apparatus itself is a portable type apparatus which does not limit the test subject's actions, biological information in normal living conditions can be easily obtained without the test subject's consciousness of measurement.

Further, according to the present invention, as barometers only necessary for evaluation in a selected generation mode is generated in correspondence with the generation mode, the amount of processing upon generation of barometers can be minimized. In addition, as unnecessary barometers are not generated, the storage capacity of storage means can be reduced.

BRIEF DESCRIPTION OF THE DRAWINGS

The above and other objects, features, and advantages of the present invention will become more apparent from the following detailed description made with reference to the accompanying drawings. In the drawings.

DETAILED DESCRIPTION OF THE PREFERRED EMBODIMENTS

First Embodiment

Hereinbelow, a first embodiment of the present invention will be described in accordance with the accompanying drawings.

Figure 1:
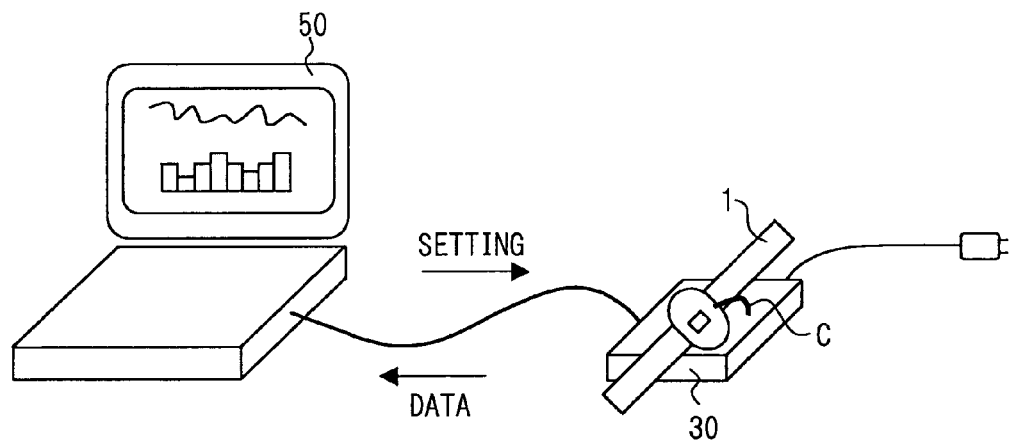
FIG. 1 is a perspective view showing the entire arrangement of a physical condition management system according to a first embodiment of the present invention.

FIG. 1 is a perspective view showing the entire arrangement of a physical condition management system to which the present invention is applied.

As shown in FIG. 1, the physical condition management system of the present embodiment has a portable biological information monitor apparatus 1 (hereinbelow, simply referred to as a "monitor") which is attached to a test subject as the subject of management when the apparatus is used; a charger 30 which charges the monitor 1 and interfaces communication with the monitor 1 via a cable C attachable to and removable from the monitor 1; and an information management unit 50 which performs communication with the monitor 1 via the charger 30 to thereby change internal settings of the monitor 1, and performs various processings based on data obtained from the monitor 1.

Note that the information management unit 50 includes a well-known personal computer having a keyboard, a display, a CPU, a ROM, a RAM, a hard disk, a communication interface, and the like. The communication interface is connected to a cable from the charger 30. A management database is formed on the hard disk. The management database is generated by accumulating data obtained from the monitor 1 via the communication interface and the charger 30, with separately-inputted various data (data on the test subject which cannot be inputted with the monitor 1, data on other test subjects, and the like). The CPU analyzes and evaluates the data accumulated in the management database, and performs processings for displaying the results of analysis and evaluation and the data accumulated in the management database on the display in various formats. Further, a management database server may be constructed through the Internet or the like so that a third person can also manage many data. In this case, the management of data may be performed via the information management apparatus or may be directly performed with the monitor. Further, data transmission and data reception are possible.

Figure 2A:
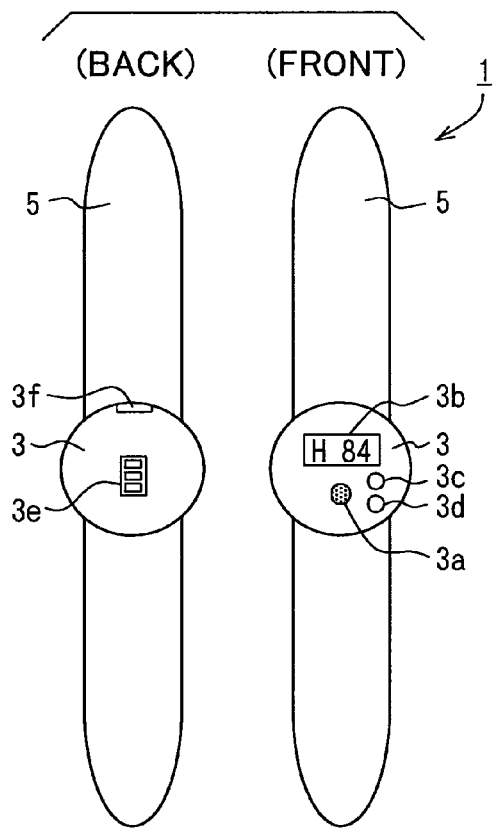
FIGS. 2A and 2B are explanatory views showing the arrangement of a portable biological information monitor apparatus and the monitor apparatus in use.
Figure 2B:
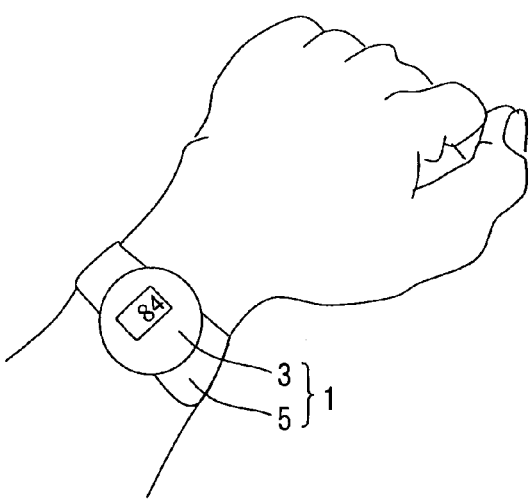

FIGS. 2A and 2B are explanatory views showing the arrangement of the monitor and the monitor apparatus in use. As shown in FIG. 2A, the monitor 1 has a main body 3 formed to approximately have a size of wrist watch, and a belt-type attachment portion 5 integrally formed with the main body 3.

An operation button 3a, a display panel 3b, a light emission diode (LED) 3c for operation check, and an LED 3d for charging check are provided on the front surface of the main body 3. A detection window 3e for transmitting light used in biological information detection and a connector 3f for connection with the cable C extended from the charger 30 are provided on the back surface of the main body 3. Further, the main body 3 is water-proof coated such that the test subject can have a bath while wearing the monitor 1.

As shown in FIG. 2B, the monitor 1 is fixed around the test subject's wrist or ankle with the attachment portion 5 when the monitor apparatus is used such that the detection window 3e on the back surface of the main body 3 is in contact with the test subject's skin. The attachment position is not limited to the wrist or ankle but may be set in any position from a finger tip to a root of all limbs. Further, the attachment portion 5 may be a supporter member in place of the belt.

Figure 3:
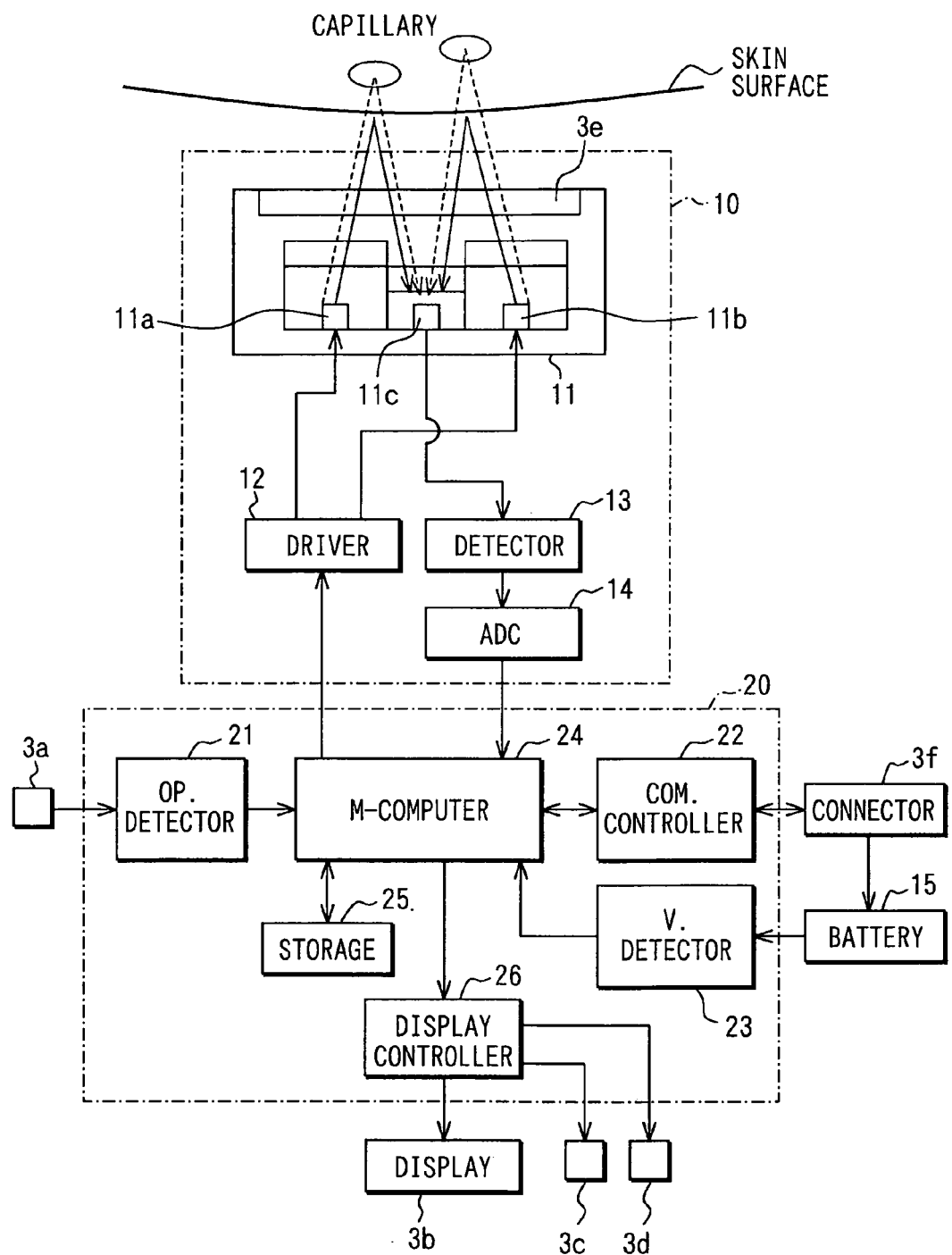
FIG. 3 is a block diagram showing the construction of the portable biological information monitor apparatus.

FIG. 3 is a block diagram showing the construction of the monitor 1. As shown in FIG. 3, the monitor 1 has an information detection unit 10 which emits light via the detection window 3e and receives reflected light to thereby detect biological information; an information processor 20 which processes the biological information detected by the information detection unit 10; and a battery 15 chargeable via the cable connected to the connector 3f, which supplies power to the respective elements of the apparatus.

The information detection unit 10 has an optical pulse wave and body motion sensor 11 having a green LED 11a to emit green light (in the present embodiment, the wavelength is about 520 nm), an infrared LED 11b to emit infrared light (in the present embodiment, the wavelength is about 950 nm), and a photo diode (PD) 11c to receive reflected light from the LEDs 11a and 11b; a driver 12 which drives the LEDs 11a and 11b in accordance with instructions from the information processor 20; a detector 13 which drives the PD 11c and generates a detection signal in correspondence with the intensity of reflected light; and an A/D converter 14 which converts the detection signal from the detector 13 into digital data.

Note that when light emitted from the LEDs 11a and 11b arrives at capillary artery running through the test subject's body, a part of the light is absorbed in hemoglobin in blood flowing through the capillary artery, and the rest of the light is reflected with the capillary artery and scattered. Then a part of the scattered light enters the PD 11c as reflected light.

At this time, as the amount of hemoglobin in the capillary artery changes in an undulating manner due to blood pulsation, the light absorbed into the hemoglobin also changes in an undulating manner. Further, as the amount of received light (signal level of the detection signal) reflected with the capillary artery and detected by the PD 11c also changes, information on pulse wave can be obtained from the detection signal.

Figure 8:
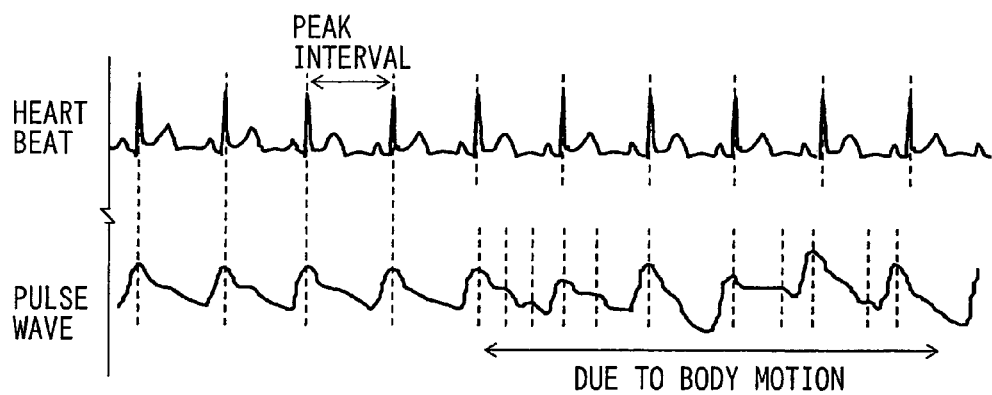
FIG. 8 is a wave form chart showing an example of pulse wave.

Note that as the blood stream is also influenced by body motion, the detection signal from the PD 11c includes a body motion component synchronized with body motion as well as a pulse component synchronized with pulse (see FIG. 8). Further, all the emitted light does not arrive at the capillary artery, and light reflected from the body surface (surface reflected light) is also received with the PD 11c. The surface reflected light also includes a body motion component.

Figure 9A:
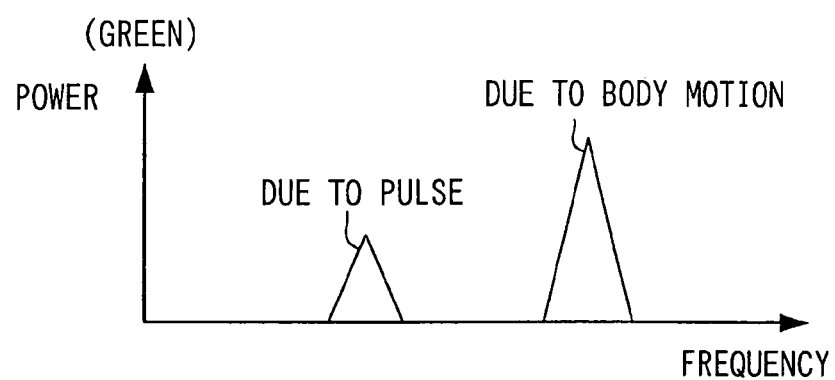
FIGS. 9A and 9B are graphs showing frequency spectra of pulse wave detection signal and body motion detection signal.
Figure 9B:
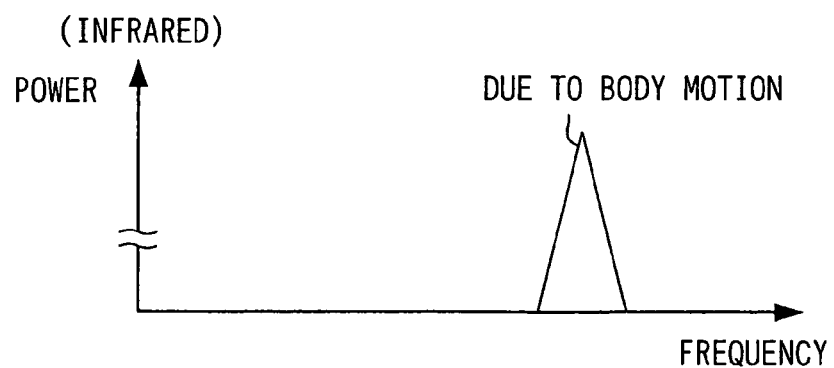

Note that infrared light has a low light absorption characteristic in comparison with green light. As shown in FIGS. 9A and 9B, in the detection signal obtained by the PD 11c upon light emission from the green LED 11a, the pulse component and body motion component are detected at extractable signal levels (see FIG. 9A). On the other hand, in the detection signal obtained by the PD 11c upon light emission from the infrared LED 11b, the pulse component is at a very low level in comparison with the body motion component and only the body motion component is detected at an extractable signal level (see FIG. 9B). Note that FIGS. 9A and 9B are graphs showing frequency spectra of the detection signal.

That is, upon light emission from the green LED 11a, the pulse wave and body motion sensor 11 operates as a pulse wave sensor which outputs a pulse wave detection signal including pulse component and body motion component, while upon light emission from the infrared LED 11b, operates as a body motion sensor which outputs a body motion detection signal including body motion component.

When the driver 12 is started in accordance with a command from the information processor 20, the driver 12 drives the LEDs 11a and 11b alternately at different timings, by preset sampling interval (50 msec in the present embodiment). Further, the A/D converter 14 operates in synchronization with the light emission timing of the driver 12, to thereby convert the pulse wave detection signal detected upon light emission from the green LED 11a and the body motion detection signal detected upon light emission from the infrared LED 11b into digital data, and provides these digital data, as biological information, to the information processor 20.

The information processor 20 has an operation detector 21 which detects an operation made with an operation button 3a; a communication controller 22 which detects cable connection with and disconnection from the connector 3f and controls communication with an external device via the cable connected to the connector 3f; a voltage detector 23 which detects a voltage of the battery 15; a microcomputer 24 which performs processing for generating barometers from biological information detected by the information detection unit 10, monitoring of battery voltage via the voltage detector 23, communication processing for communication with the external device via the communication controller 22; a storage unit 25 which holds the biological information detected by the information detection unit 10 and various information generated by the microcomputer 24 based on the biological information; and a display controller 26 which displays characters and figures on the display panel 3b and turns on and off the LEDs 3c and 3d in accordance with instructions from the microcomputer 24.

Note that at least a buffer area is ensured in the storage unit 25 for storing the biological information supplied from the information detection unit 10. The buffer area has a capacity to store data for a preset period (in the present embodiment, past 25 seconds or longer, i.e., 500 data or more by detection signal).

The microcomputer 24 is a well-known computer mainly having a CPU, a ROM, and a RAM. The microcomputer 24 performs timekeeping processing for obtaining time, data update processing for updating data in the buffer area ensured in the storage unit 25 when biological information is supplied from the information detection unit 10, and display processing for causing the display controller 26 to perform display on the display panel 3b, in addition to main processing to be described later.

Figure 4:
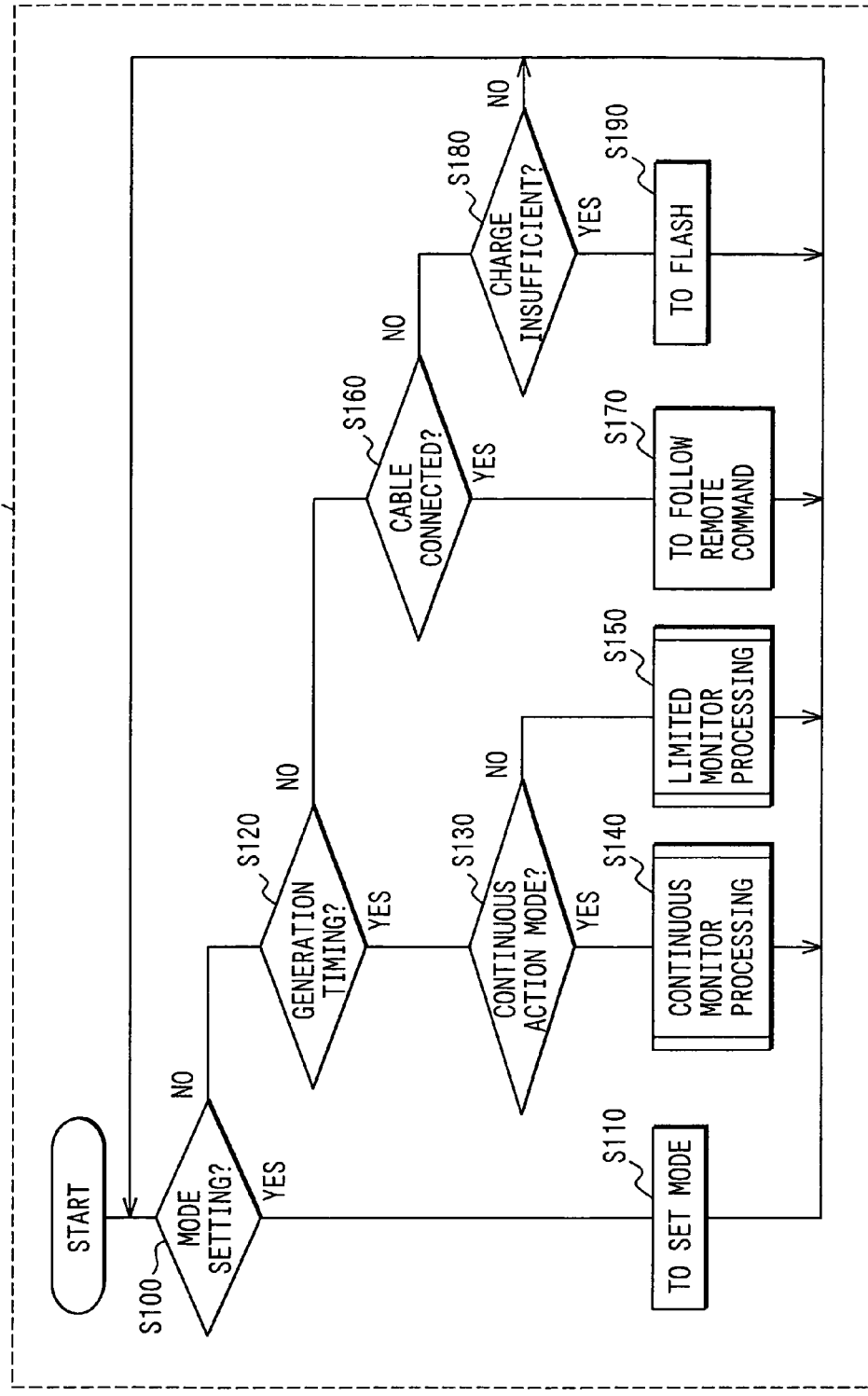
FIG. 4 is a flowchart showing the contents of main processing performed by a microcomputer of the portable biological information monitor apparatus.

Next, the main processing performed by the microcomputer 24 will be described in accordance with the flowchart of FIG. 4. When the power is turned on and the present processing is started, first, it is determined based on an input from the operation detector 21 whether or not a mode setting operation has been made via the operation button 3a (Step S100); then it is determined whether or not it is generation timing to analyze biological information detected by the information detection unit 10 and generate barometers (Step S120); then it is determined based on an input from the communication controller 22 whether or not the cable is connected to the connector 3f (Step S160); and it is determined based on an input from the voltage detector 23 whether or not the charging amount of the battery 15 is insufficient (Step S180). When the determinations are all negative (NO), these determinations are repeatedly performed as a stand-by status.

Then, when it is determined at Step S100 that the mode setting operation has been performed, various settings are performed to operate the monitor 1 in the mode set by the setting operation (Step S110), and the process returns to Step S100.

Note that in the mode setting operation, an action mode to designate a period for performing biological information monitoring (gathering and analysis), a generation mode to designate barometers generated from the biological information, and a display mode to designate contents to be displayed on the display panel 3*b* are set.

As the action mode, a continuous action mode to continuously perform monitoring without limitation of period and a limited action mode to perform monitoring within a designated period are prepared.

When one of the continuous action mode and the limited action mode has been selected as the action mode from an unselected (monitoring is not performed) status, a start command is outputted to the driver 12 of the information detection unit 10, to start detection of biological information by the information detection unit 10. On the other hand, when the system in the action mode has returned to the unselected status, the detection of biological information by the information detection unit 10 is stopped. Further, when the limited action mode has been selected, the operation check LED 3*c* is flashed while the limited action mode is maintained.

As the generation mode, a sleep mode to generate sleep evaluation barometers for evaluation of the test subject's status in sleep and a wake mode to generate wake evaluation barometers for evaluation of the test subject's status in wake are prepared. Note that the wake mode includes two sub modes for evaluation of the test subject's status in wake, i.e., a steady state motion mode to generate motion evaluation barometers for evaluation of the test subject's status in steady state motion such as jogging and a normal mode to generate wake evaluation barometers in other situations. Further, in addition to the above-described generation modes, an event mode to generate event evaluation barometers for evaluation of the test subject's status in a predetermined particular action (event) is prepared in a case where the action mode is the limited action mode.

Note that when the action mode is the continuous action mode, as the generation mode is automatically selected as described later, the generation mode can be selected only in a case where the action mode is the limited action mode.

Further, generation timing (see Step S120) to generate barometers is determined by each generation mode. The generation timing is changed in accordance with the selected generation mode. More particularly, as the change in pulse rate (barometer) increases during exercise, the generation time interval is shortened in the wake steady state motion mode in comparison with the wake normal mode, for detailed monitoring of heart rate change. Further, in sleep, as the pulse rate (barometer) does not greatly change, the generation time interval in the sleep mode is longer than that in the wake mode. That is, the generation time interval is set such that [sleep mode]>[wake normal mode]>[wake motion mode] (in the present embodiment, the generation time interval in the wake normal mode is set to 1 second or longer (1 second to 5 minutes)).

Note that the generation timing in the event mode is set such that the generation time interval becomes shorter as the frequency of change of event evaluation barometer increases.

On the other hand, as the display mode, a time display mode to display time, a barometer display mode to display barometers (pulse, body motion, autonomic nervous function, and motion lap) generated in the respective generation modes, and an evaluation result display mode to display the result of evaluation based on the barometers are prepared. Note that in the barometer display mode and the evaluation result display mode, as the displayable contents are different by set generation mode, the display contents are selected within a displayable range.

Returning to the flowchart, when it is determined at Step S120 that it is the generation timing, it is determined whether or not the set action mode is the continuous action mode (Step S130). When the action mode is the continuous action mode, continuous monitor processing is performed (Step S140), and the process returns to Step S100. On the other hand, when the action mode is not the continuous action mode but the limited action mode, limited monitor processing is performed (Step S150), and the process returns to Step S100.

Further, when it is determined at Step S160 that the cable C is connected to the connector 3*f*, remote command processing for performing processing corresponding to a remote command inputted via the cable from the information management unit 50 is performed (Step S170), and the process returns to Step S100.

In the remote command processing, for example, processing for transferring a part or all the information stored in the storage unit 25 to the information management unit 50, processing for updating programs executed at Step S140 (continuous monitor processing) and Step S150 (limited monitor processing), processing for changing the respective parameters and settings for generation timing, and the like can be performed. Further, it is determined via the cable C whether or not charging has been performed. When it is determined that charging has been performed, the charging check LED 3*d* is turned off.

Further, when it is determined at Step S180 that the amount of charging is insufficient, the charging check LED 3*d* is flashed (Step S190), and the process returns to Step S100. In this case, the charging check LED 3*d* is flashed, so that the insufficient charging is notified. However, it may be arranged such that the charging check LED 3*d* is omitted but the insufficient charging is notified by display on the display panel 3*b*, otherwise notified by voice via a separately provided speaker.

Next, the details of the continuous monitor processing performed at Step S140 will be described in accordance with the flowchart of FIG. 5. When the present processing is started, first, it is determined whether or not the set generation mode is the wake mode (Step S300). When the generation mode is the wake mode, it is determined whether or not the sub mode of the wake mode is the steady state motion mode (Step S310).

When the set mode is not the steady state motion mode but the normal mode, normal monitor processing is performed (Step S320). In the normal monitor processing, as the wake evaluation barometers for evaluation of the test subject's status in wake, the biological information stored in the buffer area of the storage unit 25 is analyzed to thereby calculate body motion and pulse. The result of calculation is then stored, along with biological information detection time, into the storage unit 25.

When the normal monitor processing (calculation of wake evaluation barometers) has been completed, it is determined based on the result of calculation (particularly the change of body motion) whether or not the test subject's action has been changed from a normal status to a status where a steady state motion such as jogging is performed, i.e., whether or not the test subject has started exercise (Step S330). When it is determined that the test subject has started exercise, the setting of the generation mode is changed to the wake steady state motion mode, and the setting of the generation timing is changed to that corresponding to the wake steady state motion mode (Step S340), and the process ends.

On the other hand, when it is determined at Step S310 that the generation mode is the steady state motion mode, motion monitor processing is performed (Step S380). In the motion monitor processing, as the motion evaluation barometers for evaluation of the test subject's status in steady state motion, the biological information stored in the buffer area of the storage unit 25 is analyzed, to thereby calculate body motion, pulse and motion pitch. The result of calculation is then stored, along with biological information detection time, into the storage unit 25.

When the motion monitor processing (calculation of motion evaluation barometers) has been completed, it is determined based on the result of calculation (particularly the change of body motion) whether or not the test subject's motion has been changed from the status of steady state motion to a normal status where the test subject does not do exercise, i.e., whether or not the test subject has completed the exercise (Step S390). When it is determined that the test subject has not ended the exercise, the process ends.

On the other hand, when it is determined that the test subject has ended the exercise, motion evaluation is performed, based on the motion evaluation barometers generated while the steady state motion mode was continued, to evaluate the load of exercise and influence of the exercise on the test subject's body (Step S400). Thereafter, the setting of the generation mode is changed to the wake normal mode, and the setting of the generation timing is changed to that corresponding to the wake normal mode (Step S410). The process then ends.

When it is determined at Step S330 that the test subject has not started exercise, it is determined based on the result of calculation in the normal monitor processing whether or not the test subject has fallen asleep (Step S350). For example, as the determination, it is determined that the test subject has fallen asleep when no body motion has occurred for a predetermined period or longer (e.g., 5 minutes) and the pulse rate has become lower than a mean value in the wake normal mode by predetermined pulse-beats (e.g., 5 beats).

When it is determined that the test subject has not fallen asleep, the present process ends. By contrast, when it is determined that the test subject has fallen asleep, daytime activity amount evaluation is performed, based on the wake evaluation barometers and the motion evaluation barometers generated while the wake mode was continued, to comprehensively evaluate the test subject's state through the wake mode (e.g., consumed calories and activity amount). Further, when the results of past daytime activity amount evaluation and sleep evaluation are stored in the storage unit 25, the test subject's status is comprehensively evaluated based on the past evaluation results and the result of current daytime activity amount evaluation (Step S360).

Thereafter, the setting of the generation mode is changed to the sleep mode, and the setting of the generation timing is changed to that corresponding to the sleep mode (Step S370). The process then ends.

Further, when it is determined at Step S300 that the generation mode is not the wake mode but the sleep mode, sleep monitor processing is performed (Step S420). In the sleep monitor processing, as the sleep evaluation barometers for evaluation of the test subject's status in sleep, the biological information stored in the buffer area of the storage unit 25 is analyzed to thereby calculate body motion, pulse and autonomic nervous activity amount. The result of calculation is then stored, along with biological information detection time, into the storage unit 25.

When the sleep monitor processing (calculation of sleep evaluation barometers) has been completed, sleep abnormality determination processing is performed (Step S430) based on the result of calculation, to determine abnormality in sleep (e.g., arrhythmia, apnea, or hyperanakinesia).

Figure 6:
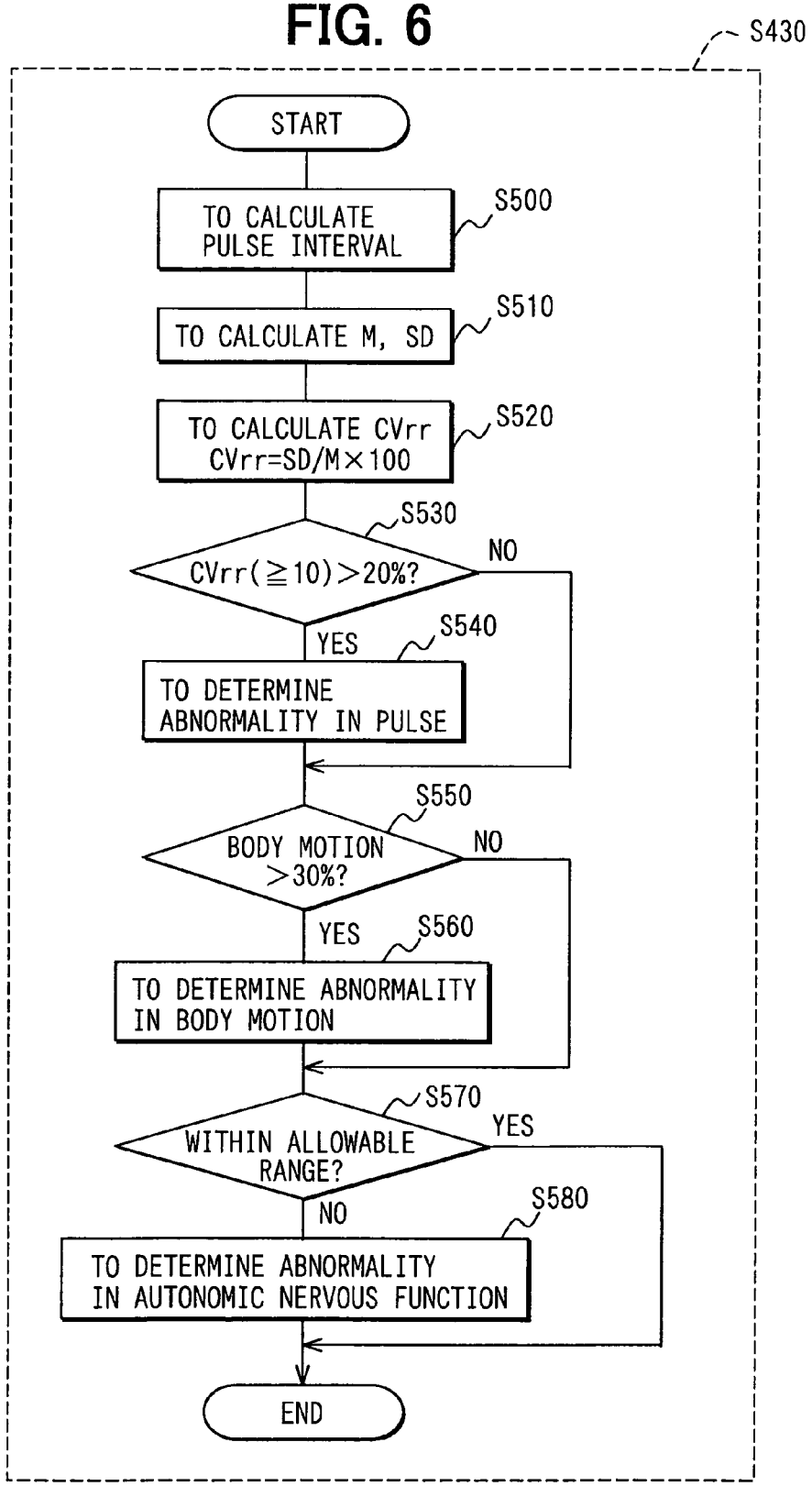
FIG. 6 is a flowchart showing the details of sleep abnormality determination.

As shown in FIG. 6, in the sleep abnormality determination processing, first, a pulse interval is calculated (Step S500) from the result of analysis of a pulse wave detection signal performed upon acquisition of pulse as one of the sleep evaluation barometers at Step S420 (sleep monitor processing). A mean pulse interval M and a standard deviation SD of pulse intervals are obtained (Step S510) with respect to a predetermined time range (e.g., 5 minutes). Further, based on the mean pulse interval M and the standard deviation SD, an evaluation value CVrr is calculated with respect to a predetermined time range (Step S520) from the following expression (1). Note that the evaluation value CVrr indicates the degree of change of nonsingular pulse variation regardless of time order.

$$CVrr = SD/M \times 100 \tag{1}$$

Then it is determined whether or not time where the evaluation value CVrr is 10 or greater is 20% or more of a preset period (e.g., from hypnagogic point to current time point) (Step S530). When this time is 20% or more, it is determined that the pulse has an abnormality (arrhythmia, apnea, hyperanakinesia or the like) (Step S540).

Further, it is determined based on the sleep evaluation barometers (body motion) calculated at Step S420 whether or not time, where it is determined that body motion occurred, is 30% or more of a preset period (e.g., from hypnagogic point to current time point) (Step S550). When this time is 30% or more, it is determined that the body motion has an abnormality (hyperanakinesia) (Step S560).

Further, it is determined based on the sleep evaluation barometer (autonomic nervous function) calculated at Step S420 whether or not a high frequency component HF and a low frequency component (parasympathetic nervous activity amount) LF appear in the pulse, and a ratio between the high frequency and low frequency components (sympathetic nervous activity amount) LF/HF, are within an allowable range (e.g., $10 \leq HF \leq 100$ and $10 \leq LF \leq 100$ and $LF/HF \leq 4$) (Step S570). If even one of them is without the allowable range, it is determined that an abnormality (arrhythmia, apnea, hyperanakinesia or the like) exists (Step S580), and the process ends.

Figure 5:
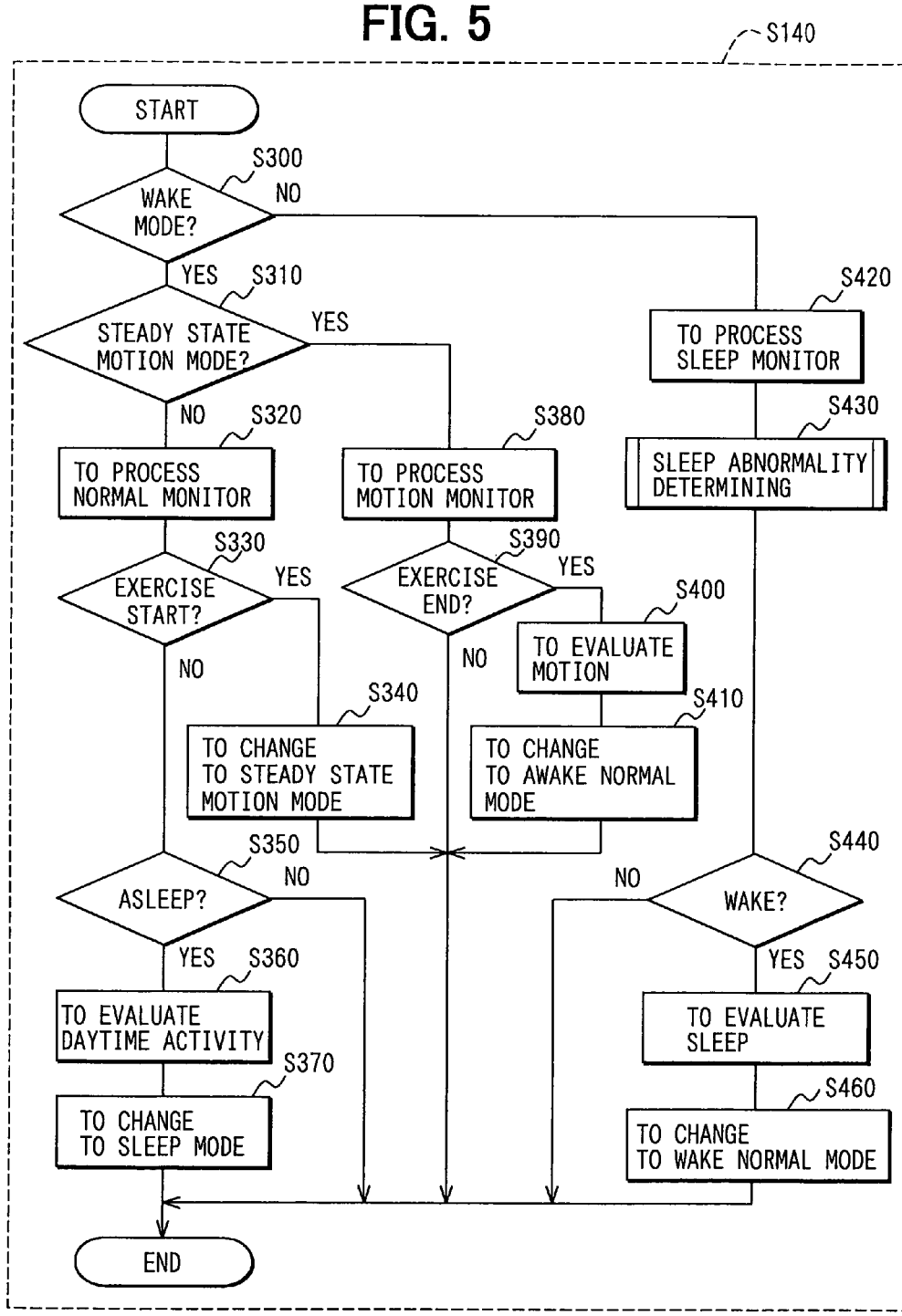
FIG. 5 is a flowchart showing the details of continuous monitor apparatus processing.

When the sleep abnormality determination has been completed, the process returns to FIG. 5, and it is determined based on the result of calculation in the sleep monitor processing whether or not the test subject has woke up (Step S440). For example, as the determination, when body motion has occurred in a period of predetermined or greater ratio (e.g., 1/6) of past predetermined period (e.g., 3 minutes) and the pulse rate has become higher than a mean value in the sleep mode by predetermined pulse-beats (e.g., 5 beats), it is determined that the test subject has woke up.

When it is determined that the test subject has not woke up, the process ends. By contrast, when it is determined that the test subject has woke up, sleep evaluation is performed based on the sleep evaluation barometers generated while the sleep mode was continued and the result of determination in the sleep abnormality determination processing, so as to evaluate the test subject's status through the entire sleep mode (e.g., the quality of sleep, the depth of sleep (rhythm), hypnagogic state, and the like). Further, when the results of past daytime activity amount evaluation and sleep evaluation are stored in the storage unit 25, the test subject's status is comprehensively evaluated based on these past evaluation results and the result of current sleep evaluation (Step S450).

Thereafter, the setting of the generation mode is changed to the wake normal mode, and the setting of the generation timing is changed to that corresponding to the wake normal mode (Step S460), and the process ends.

That is, in the continuous monitor processing (continuous action mode), the test subject's action is estimated from the biological information (barometers), and a generation mode corresponding to the action is automatically selected while barometers appropriate to the test subject's action are generated, and evaluation and comprehensive evaluation in the generation mode are performed upon each selection of generation mode.

Note that the sleep abnormality determination (Step S430) is performed at each detection timing; however, the determination may be performed simultaneously with the sleep evaluation (Step S450) upon changing from the sleep mode to the wake mode.

Figure 7:
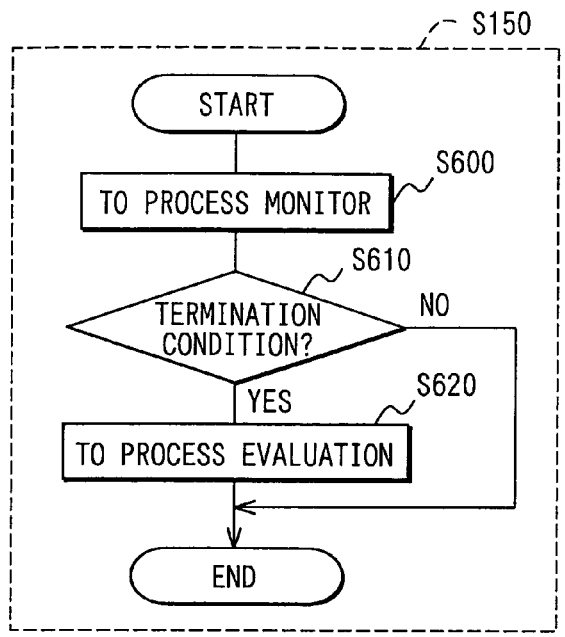
FIG. 7 is a flowchart showing the details of limited monitor processing.

Next, the limited monitor processing performed at Step S150 will be described in accordance with the flowchart of FIG. 7. When the present processing has been started, first, the monitor processing corresponding to the set generation mode is performed (Step S600). That is, when the generation mode is the wake normal mode, the normal monitor processing at Step S320 is performed. When the generation mode is the wake steady state motion mode, the motion monitor processing at Step S380 is performed. When the generation mode is the sleep mode, the sleep monitor processing at Step S420 is performed. When the generation mode is the event mode, event monitor processing is performed. In the event monitor processing, as event evaluation barometers, body motion, pulse, and autonomic nervous function are obtained.

Then it is determined whether or not a preset termination condition is satisfied (Step S610). When the termination condition is not satisfied, the process ends, while when the termination condition is satisfied, evaluation processing corresponding to the set generation mode is performed (Step S620), and the process ends.

Note that as the termination condition, for example, operation of the operation button 3a to request termination of monitoring, elapse of predetermined fixed period, change of the test subject's status estimated from the calculated barometers or the like may be used.

Further, in the evaluation processing, when the set generation mode is the wake normal mode, the daytime activity amount evaluation (except comprehensive evaluation) at Step S360 is performed. When the set generation mode is the wake steady state motion mode, the motion evaluation at Step S400 is performed. When the set generation mode is the sleep mode, the sleep abnormality determination at Step S430 and the sleep evaluation (except comprehensive evaluation) at Step S450 are performed. Note that when the set generation mode is the event mode, evaluation appropriate to the event is performed.

That is, in the limited monitor processing (limited action mode), while the generation mode is fixed, monitoring, generation of barometers, and evaluation based on the barometers are performed only within a limited period.

Next, an algorithm used in calculation of barometers such as body motion, pulse, autonomic nervous function, motion pitch, and the like from biological information (sampling data of pulse detection signal and body motion detection signal) in the normal monitor processing at Step S320, the motion monitor processing at Step S380, and the sleep monitor processing at Step S420 will be described.

First, as the body motion, an amplitude value of body motion detection signal or an amplitude value of differential waveform of body motion signal (e.g., mean or accumulated value by 1 second) is obtained. Then the occurrence and nonoccurrence of the body motion and the magnitude of body motion are obtained from the amplitude value and the number of zero-level crossings of the body motion detection signal is counted (so-called zero-crossing method), and the frequency of body motion is obtained from the count value.

The pulse is obtained by performing FFT (Fast Fourier Transform) processing on the pulse wave detection signal and the body motion detection signal and by thereby specifying a component having a maximum peak (pulse component) from the FFT result of the pulse wave detection signal. Note that in a case where body motion occurs, a body motion component is specified from the FFT result of the body motion detection signal, and the body motion component is eliminated from the FFT result of the pulse wave detection signal. Note that upon execution of FFT processing, zero addition (adding virtual data having a value of zero to actual data thereby increasing the number of data before FFT processing) as a well-known technique for improvement in frequency resolution and reduction of response time (time required for data accumulation) may be performed.

The motion pitch is obtained by specifying the body motion component from the FFT result of the body motion detection signal. In a case where the frequency peak (fundamental or harmonic wave) of the specified body motion component is clear, the motion pitch is obtained from the frequency of the body motion component on the assumption that the body motion is caused by steady state motion such as jogging.

The autonomic nervous function (HF, LF, and LF/HF) is obtained by using a well-known algorithm (e.g., see JP-2002-330935 A) to repeatedly perform complex demodulation analysis on a pulse wave signal.

In this manner, processing with different algorithms must be performed for the respective barometers (body motion, pulse, autonomic nervous function, and pitch). In the monitor 1, all the barometers are not always required. In the wake normal mode (normal monitor processing), body motion and pulse are obtained. In the wake steady state motion mode (motion monitor processing), body motion, pulse, and pitch are obtained. In the sleep mode (sleep monitor processing), body motion, pulse, and autonomic nervous function are obtained. Thus barometers only necessary for the set generation mode are obtained.

Figure 10:
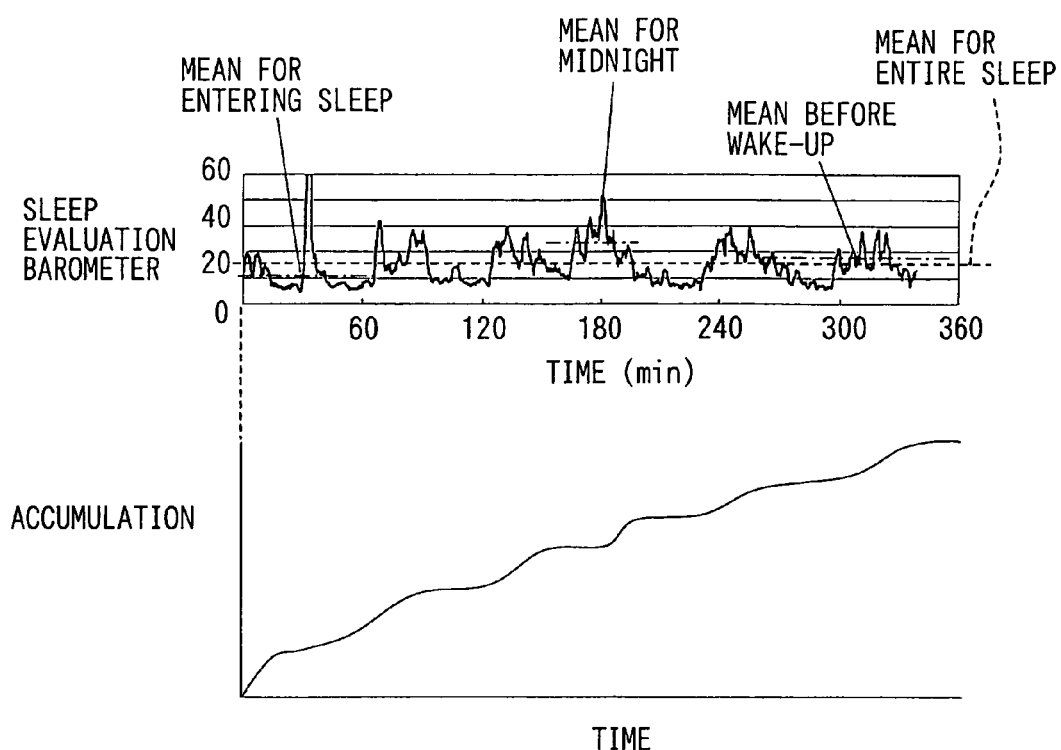
FIG. 10 is an explanatory diagram showing an example of sleep evaluation barometer and a description of secondary barometer generated based on the sleep evaluation barometers.

As the evaluation in the respective generation modes performed in the daytime activity amount evaluation at Step S360, the motion evaluation at Step S400 and the sleep evaluation at Step S450, primary barometers (body motion, pulse, and autonomic nervous function (HF, LF, and LF/HF)), obtained from the normal monitor processing at Step S320, the motion monitor processing at Step S380 and the sleep monitor processing at Step S420, may be used. Further, secondary barometers, obtained by processing based on the primary barometers (mean value, accumulated value, maximum value, minimum value, the difference between the maximum and minimum value of primary barometer, time change rate, CVrr, and the like), may be used. Further, a barometer to be subject of processing may be obtained in the entire period of the generation or may be obtained in a part of the period (see FIG. 10).

For example, in the daytime activity amount evaluation, it may be arranged such that consumed calories are obtained from an accumulated value (secondary barometer) of pulse rate (primary barometer) through the entire period of the wake mode, and the momentum is evaluated from the consumed calories. Further, the change in activity amount may be grasped from the frequency of body motion (primary barometer).

Further, in the sleep evaluation, it may be arranged such that the quality of sleep is evaluated from a mean value (or accumulated or maximum value) of sleep evaluation barometers in the entire or part of the period of sleep mode. Further, it may be arranged such that the depth of sleep (rhythm) is evaluated from the time change rate (or the difference between maximum and minimum values) of the sleep evaluation barometers. Further, it may be arranged such that the hypnagogic state is evaluated from the time change rate of the sleep evaluation barometers within a predetermined period from bedtime (e.g., 3 hours). Note that as the above-described period of time, several hours before or after the bedtime, particular midnight time zone or the like may be used.

Further, in the comprehensive evaluation, in addition to the daytime activity amount evaluation and the sleep evaluation, evaluation using barometers obtained in separately-performed event mode or results of evaluation using the barometers may be performed.

As described above, in the physical condition management system of the present embodiment, the monitor 1 is attached to the test subject and operated in the continuous action mode or limited action mode, so that information necessary for evaluation of the test subject's status can be obtained.

At this time, when the monitor 1 is operated in the continuous action mode, barometers appropriate to evaluate the test subject's status in the test subject's occasional actions can be continuously obtained for long hours without bothering the test subject.

That is, as attachment and removal of the monitor 1 in correspondence with the test subject's action is not required and connection between the monitor 1 and the cable is not required during monitor operation, the test subject's actions are not limited, and biological information in normal living conditions can be easily obtained.

The information continuously obtained for long hours includes information on various actions which appear in a day in addition to particular actions such as sleeping and exercise. Accordingly, the life rhythm, the exercise load, the physical condition, the consumed calories, the quality of sleep, and the like can be comprehensively evaluated based on these information, and accurate advice can be dispensed to the test subject based on the result of evaluation.

Further, in a case where the monitor 1 is operated in the limited action mode, as the generation mode can be arbitrarily designated, desired barometers can be obtained.

For example, suppose that it is arranged such that the event mode is selected as the generation mode and information (barometers) obtained by the monitor 1 are fed back to an external device (e.g., air ventilation device, air conditioning machine or the like) having influence on the test subject's status. Here, a system can be constructed to automatically control the environment in a closed space (car interior, bedroom, meeting room, and the like) to comfortable state in accordance with the test subject's status.

Further, in the monitor 1, multiple generation modes corresponding to the test subject's actions are prepared. The barometer generation timing (barometer generation interval) is changed for each generation mode, and barometers only necessary in the generation mode are generated. Accordingly, processing amount (by extension, electric power consumption) upon barometer generation can be suppressed to a minimum value.

Further, the information obtained by the monitor 1 (barometers and evaluation results) can be displayed on the display panel 3*b* of the monitor 1 by appropriately selecting the display mode. Accordingly, the test subject can check barometers and evaluation results in accordance with necessity.

Further, in the physical condition management system according to the present embodiment, information obtained by the monitor 1 can be transferred to the information management unit 50 while the monitor 1 is charged by the charger 30.

In the information management unit 50, data which cannot be obtained by the monitor 1 is also accumulated in the management database. Accordingly, by adding such data to data read from the monitor 1 and performing reanalysis and reevaluation, more detailed evaluation in comparison with that performed in the monitor 1 can be performed.

Further, differently from the monitor 1, the information management unit 50 can be provided with a large display screen. Accordingly, various data stored in the management database can be displayed in such a manner that the test subject's status can be more accurately grasped. For example, arbitrary information stored in the management database can be displayed within an arbitrary span (time unit, day unit, week unit, month unit, year unit or the like) for understanding of transition of data, or may be displayed in contrast with data on another test subject or mean value or the like of data on many other test subjects.

The physical condition management system according to the present embodiment can be used in physical condition management for athletes, patients, aged and disabled persons, as well as personal health care for a user as the test subject; thus, the system is applicable to fields of sports, medical, and public welfare.

The first embodiment of the present invention has been described as above; however, the present invention is not limited to the above embodiment but implemented as various aspects.

Figure 11:
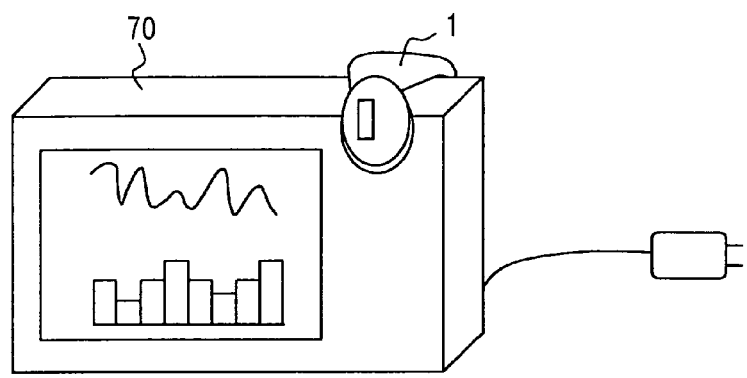
FIG. 11 is a perspective view of an example of information management apparatus integrated with a charger.

For example, in the above embodiment, the monitor 1 and the information management unit 50 communicate with each other via the charger 30; however, as shown in FIG. 11, the charger may be integrated with an information management unit 70. Further, it may be arranged such that the charger 30 is provided with a display unit having a screen larger than that of the monitor 1, and the monitor 1 is provided in the charger 30; thereby information obtained by the monitor 1 is displayed in more easily-viewable format in comparison with display on the display panel 3*b* of the monitor 1.

Further, it may be arranged such that multiple monitors 1 directly perform communication and mutually exchange data.

Further, in the above embodiment, the communication controller 22 performs cable communication via the cable C connected to the connector 3*f*; however, wireless communication may be performed. In this case, it may be further arranged such that the operation button 3*a* is omitted and a separately prepared remote controller is used, and various mode settings are performed via the communication controller 22.

Further, in the above embodiment, the sensor having the green LED 11*a* and the infrared LED 11*b* is employed for biological information detection; however, it may be arranged such that a sensor only having the green LED 11*a* is used and pulse component and body motion component are extracted from a pulse wave detection signal.

Further, in the above embodiment, the sensor for biological information detection is not limited to the optical sensor but any type of sensor can be used as long as it detects biological information reflecting body motion, pulse, and autonomic nervous function and has a small size for portability.

Further, as detected biological information, information reflecting skin temperature, diaphoretic amount, and the like as well as the above-described biological information may be detected.

Further, in the above embodiment, only the sleep mode is prepared as the generation mode in sleep; however, an midway wake mode may be provided.

Further, it may be arranged such that it is determined whether or not the monitor 1 is attached to the test subject based on the photoreception level or the like in the PD 11c, and when it is determined that the monitor 1 is not attached yet, barometers or the like are not displayed on the display panel 3b.

Further, it may be arranged such that immediately after the monitor 1 has been attached to the test subject, barometers or the like are not displayed on the display panel 3b before the pulse rate becomes stabled. At this time, a message requiring bed rest may be displayed on the display panel 3b.

Further, in the above embodiment, the monitor 1 performs operations including evaluation based on generated barometers; however, it may be arranged such that the monitor 1 performs operations including data acquisition or barometer generation, and then the information management unit 50 performs barometer generation or evaluation.

Second Embodiment

A second embodiment of the present invention relates to a biological status detection apparatus to detect a biological status indicating a pulse rate, pulse interval, and the like.

In recent years, there is an increasing need to monitor a heartbeat (heart rate) in daily life and upon exercise such as jogging for the purpose of health care. Generally, an action potential which occurs accompanying the heartbeat is measured from regions of chest with an electrocardiograph, and a heart rate is calculated from time interval of R wave which appears in the result of measurement (electrocardiogram). However, in the measurement using the electrocardiograph, electrodes attached to a test subject's body bother the test subject and further limit the test subject's actions.

Then a method using an optical pulse wave sensor, easily attachable to a finger or temple, in place of electrocardiograph, has been proposed. A pulse wave is a pressure fluctuation in an artery which occurs in accordance with a heartbeat and which is transmitted to a peripheral artery as a wave. The optical pulse wave sensor measures an undulating volume change of blood in the peripheral artery by utilizing light absorption characteristic of hemoglobin in the blood.

Figure 30:
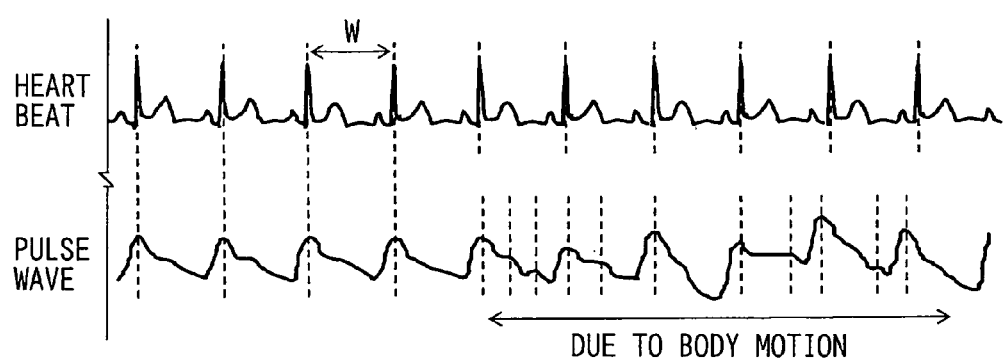
FIG. 30 is a graph showing an example of pulse wave form.

Upon use of the pulse wave sensor, as shown in FIG. 30, a pulse rate N is calculated from a pulse wave peak appearance interval W. However, when body motion occurs in a portion where the pulse wave sensor is attached, a peak synchronized with the body motion appears in the detected pulse wave independently of the pulse rate (heartbeat) due to turbulence of blood stream in the peripheral artery. As a result, the pulse rate calculated by using the pulse wave sensor does not correspond with the actual pulse rate. Further, the peak based on the body motion (body motion component) may appear in a frequency area overlapping with a peak based on the pulse, and cannot be easily eliminated with a filter or the like.

To solve this problem, an apparatus, having a body motion sensor (acceleration sensor) in addition to a pulse wave sensor is known (e.g., see JP2816944 B2 (U.S. Pat. No. 5,697,374)). When the body motion sensor has detected body motion, the apparatus eliminates a body motion component specified from a detection signal from the body motion sensor and extracts a pulse component based on the result of frequency analysis (spectra) of a detection signal obtained by the pulse wave sensor. Here, however, although a compact optical pulse wave sensor is used for not limiting the test subject's actions, a separate body motion sensor is required. This entails a problem of increase in the number of apparatus components.

Further, an apparatus using an optical pulse wave sensor to emit two types of lights having different wavelengths is known (e.g., see JP-H7-88092 A (U.S. Pat. No. 6,022,321)). The apparatus discriminates a pulse component from a body motion component and detects exercise intensity of the living body or the like, from a ratio and the change of rate between amplitudes of peak frequency components included in the respective detection signals. The detection signals are detected using the lights having different wavelengths. Here, two facts are utilized, i.e, the first fact that the light absorption characteristic of blood component changes in correspondence with light wavelength, and the second fact that the motion of living body influences blood flow rate.

Here, the separate body motion sensor is unnecessary, so that the size of the apparatus can be compact. However, note that a relationship between a body motion component and a pulse component is affected by various factors, i.e., an attachment state of the sensor, individual differences (e.g., in heart beat strength or in subcutaneous fat thickness) of the test subject. Further, note that the apparatus does not consider reflected light from the skin of the test subject that is significantly affected by the body motion. Therefore, the calculation processing adopted in the apparatus cannot obtain the pulse and exercise data with high accuracy. In particular, when the pulse sensor is attached to an arm or leg for aiming at convenience, a detection sensitivity for the pulse wave is decreased because of the subcutaneous fat compared with a case where the sensor is attached to a peripheral member such as a finger. The pulse component is thereby hidden by the body motion component.

Figure 12A:
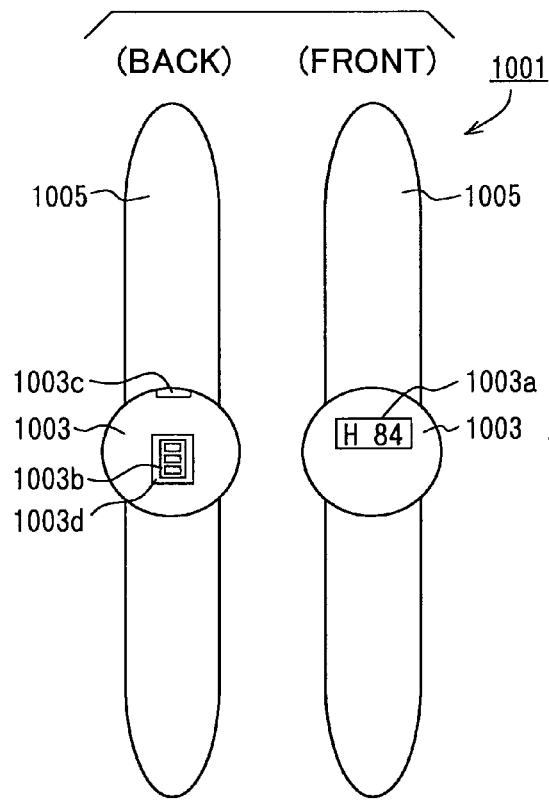
FIGS. 12A and 12B are explanatory views showing the arrangement of a biological status detection apparatus and the apparatus in use according to a second embodiment of the present invention.
Figure 12B:
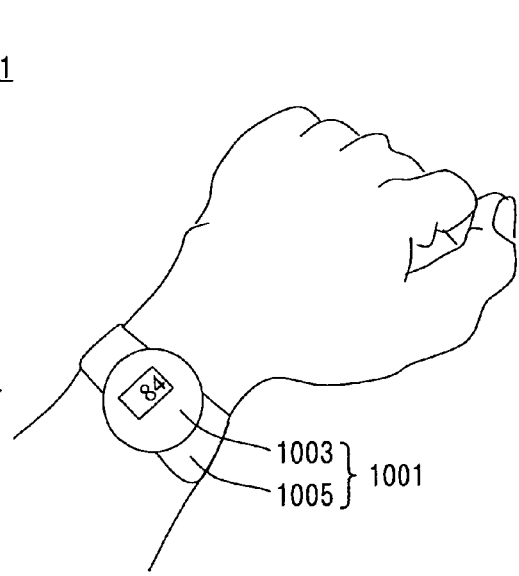

A biological status detection apparatus according to the second embodiment of the present invention can solve the above problems. FIGS. 12A and 12B are explanatory views showing the arrangement of a biological status detection apparatus 1001 and the apparatus in use.

As shown in FIGS. 12A and 12B, a biological status detection apparatus 1001 of the present embodiment has a main body 1003 formed to approximately have a size of wrist watch, and a belt-type attachment portion 1005 integrally formed with the main body 1003.

A display panel 1003a is provided on the front surface of the main body 1003. A light transmitting plate 1003b forming a detection window for transmitting light used in detection of biological information, and a connector 1003c for connection with a cable C for communication with an external device and for charging the apparatus are provided on the back surface of the main body 1003.

When the biological status detection apparatus 1001 is used, as shown in FIG. 12B, the apparatus is fixed around a test subject's wrist or ankle with the attachment portion 1005 such that the back surface of the main body 1003 where the light transmitting plate 1003b is formed is in contact with the test subject's skin. The attachment position is not limited to the wrist or ankle but may be set in any position from finger tip to root of all limbs. Further, the attachment portion 1005 may be a supporter member in place of the belt.

Figure 14:
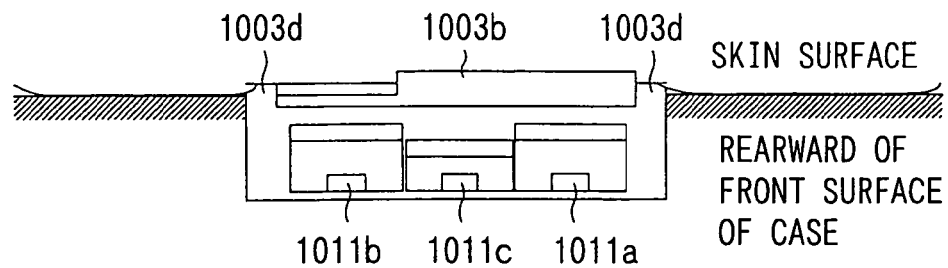
FIG. 14 is a cross-sectional view explaining the structure of a case and a light transmitting plate constructing a pulse wave sensor and the sensor in use.

A casing constructing the main body 1003 has a structure where a peripheral portion 1003d of the light transmitting plate 1003b is projected further than other portions (in the present embodiment, by about 0.2 mm) such that the light transmitting plate 1003b becomes in close contact with the test subject's skin upon attachment of the apparatus 1001 to the test subject (see FIG. 14). Further, the main body 1003 is water-proof coated such that the test subject can have a bath while wearing the biological status detection apparatus 1001.

Figure 13:
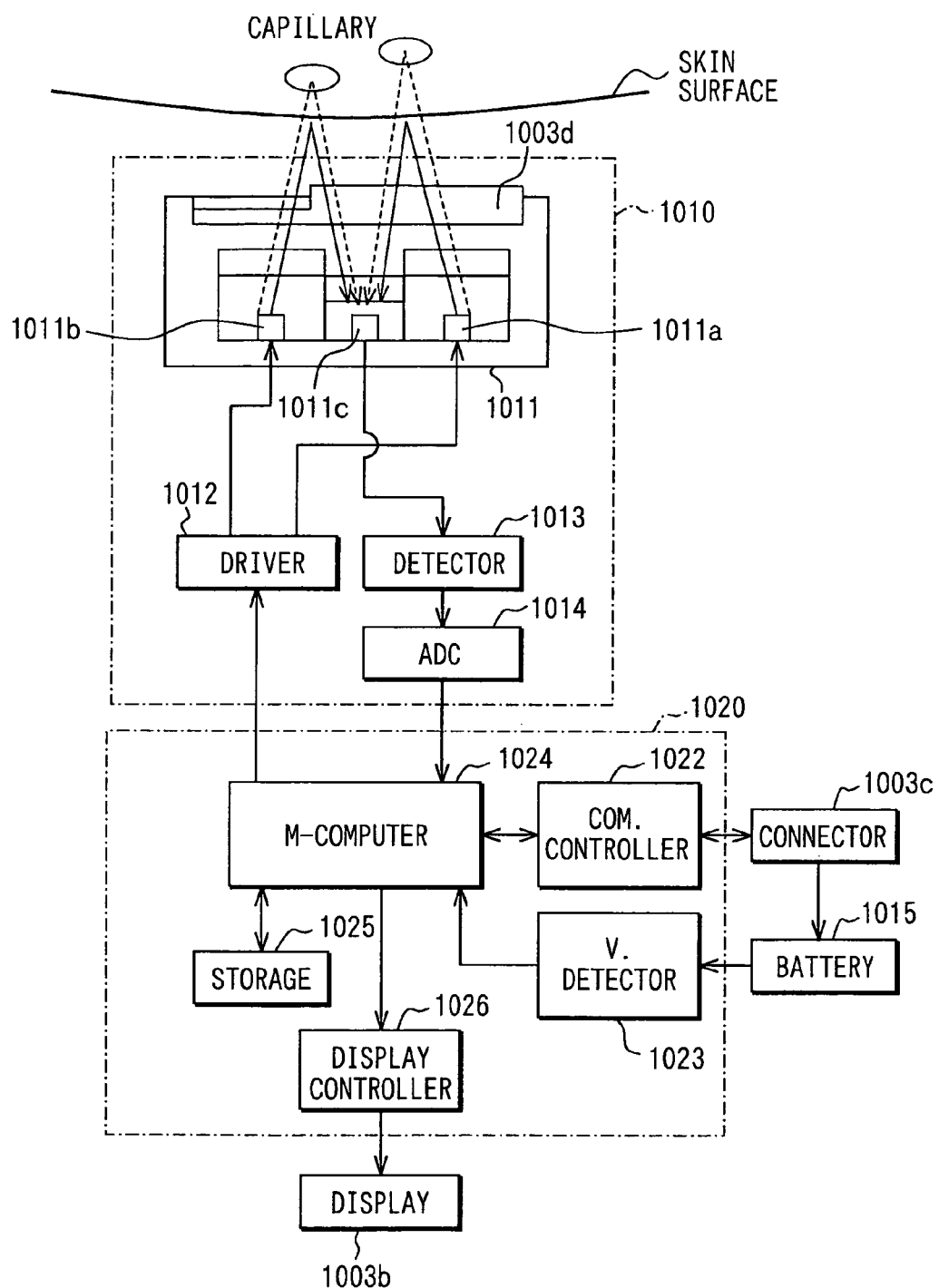
FIG. 13 is a block diagram showing the construction of the biological status detection apparatus.

Next, FIG. 13 is a block diagram showing the construction of the biological status detection apparatus. As shown in FIG. 13, the biological status detection apparatus 1001 has an information detection unit 1010 which emits light via the light transmitting plate 1003b and receives reflected light thereby detects biological information, an information processor 1020 which processes the biological information detected by the information detection unit 1010, and a battery 1015 chargeable via the cable connected to the connector 1003c, which supplies power to the respective elements of the apparatus.

The information detection unit 1010 has an optical pulse wave sensor 1011 having a green LED 1011a to emit green light (in the present embodiment, the wavelength is about 520 nm), an infrared LED 1011b to emit infrared light (in the present embodiment, the wavelength is about 950 nm), and a photo diode (PD) 1011c to receive reflected light from the LEDs 1011a and 1011b; a driver 1012 which drives the LEDs 1011a and 1011b in accordance with instructions from the information processor 1020; a detector 1013 which drives the PD 1011c and generates a detection signal in correspondence with the intensity of reflected light; and an A/D converter 1014 which converts the detection signal from the detector 1013 into digital data.

Further, in the light transmitting plate 1003b, a portion opposite to the green LED 1011a and the photo diode 1011c (hereinbelow, referred to as a "first portion"), i.e., a portion as a path of light emitted from the green LED 1011a and its reflected light, is projected further than the peripheral portion 1003d of the light transmitting plate 1003b (in the present embodiment, by 0.2 mm). By contrast, a portion opposite to the infrared LED 1011b (hereinbelow, referred to as a "second portion"), i.e., a portion as a path of light emitted from the infrared LED 1011b, has a shape dented further than the peripheral portion 1003d of the light transmitting plate 1003b (in the present embodiment, by 0.2 mm). Suppose the degree of adhesion to the test subject's skin when the apparatus 1001 is attached to the test subject, as shown in FIG. 14. Here, the degree of adhesion to the test subject's skin is high in the portion as a path of light emitted from the green LED 1011a (green light) and its reflected light. By contrast, the degree of adhesion to the test subject's skin is low (or the portion is not in close contact with the skin) in the portion as a path of light emitted from the infrared LED 1011b (infrared light).

When light emitted from the LEDs 1011a and 1011b to the test subject arrives at capillary artery running through the test subject's body, a part of the light is absorbed in hemoglobin in blood flowing through the capillary artery, and the rest of the light is reflected with the capillary artery and scattered. Then a part of the scattered light enters the PD 1011c as reflected light.

At this time, as the amount of hemoglobin in the capillary artery changes in an undulating manner due to blood pulsation, the light absorbed into the hemoglobin is also changed in an undulating manner. Further, as the amount of light (signal level of the detection signal) reflected with the capillary artery and detected by the PD 1011c is also changed, information on a pulse wave can be obtained from the detection signal.

Note that as a blood stream is also influenced by body motion, the detection signal from the PD 1011c includes a body motion component synchronized with body motion as well as a pulse component synchronized with the pulse (see FIG. 30). Further, all the emitted light does not arrive at the capillary artery, and light reflected from the body surface (surface reflected light) is also received with the PD 1011c. The surface reflected light also includes a body motion component.

Note that infrared light has a low light absorption characteristic in comparison with green light. In the detection signal detected by the PD 1011c upon light emission from the infrared LED 1011b (body motion detection signal), the pulse component synchronized with the pulse is smaller in comparison with the detection signal detected by the PD 1011c upon light emission from the green LED 1011a (pulse wave detection signal). The body motion component synchronized with body motion is thereby relatively emphasized in the detection signal detected by the PD 1011c upon light emission from the infrared LED 1011b.

Further, the green light emitted via the first portion of the light transmitting plate 1003b easily arrives at the capillary artery running through the test subject's body and reflected light from the capillary artery is easily received. Accordingly, the sensitivity of pulse component detection in the pulse wave detection signal is improved. On the other hand, the infrared light emitted via the second portion of the light transmitting plate 3b is easily reflected on the skin surface and its irradiation position is easily moved in accordance with body motion. Accordingly, the sensitivity of pulse component detection in the body motion detection signal is degraded but the sensitivity of body motion detection is improved.

Figure 15A:
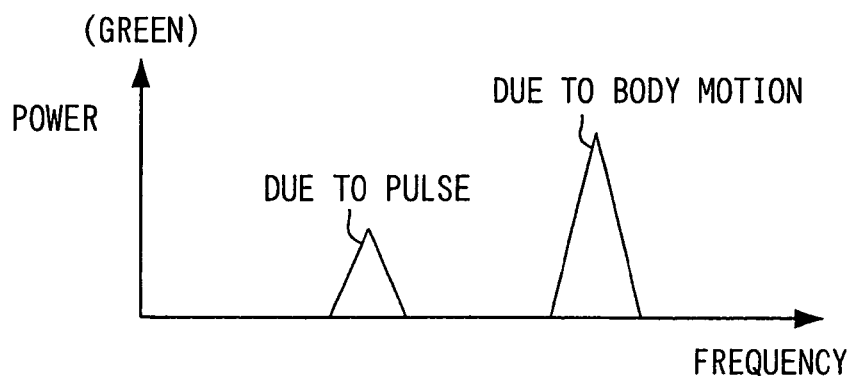
FIGS. 15A and 15B are graphs showing frequency spectra of pulse wave detection signal and body motion detection signal detected when body motion occurs in a test subject.
Figure 15B:
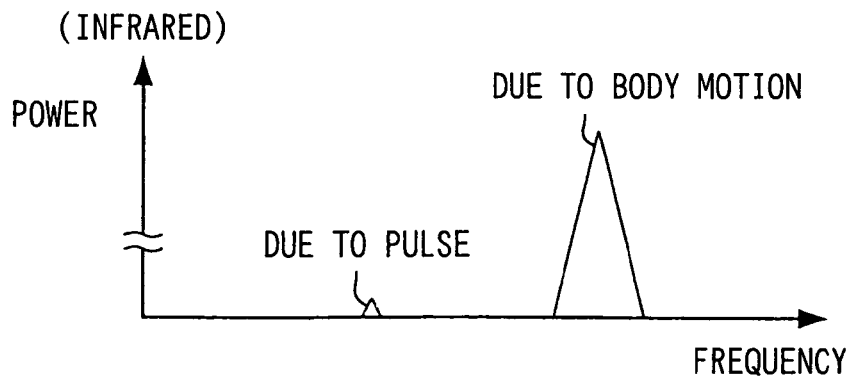

As a result, as shown in FIG. 15A, in the pulse wave detection signal, the pulse component and the body motion component are detected at signal levels not so different from each other (in the present embodiment, about 1:5). On the other hand, as shown in FIG. 15B, in the body motion detection signal, the pulse component is detected at a very low signal level in comparison with that of the body motion component (in the present embodiment, about 1:50). Note that FIGS. 15A and 15B are graphs showing frequency spectra of pulse wave detection signal and body motion detection signal detected when body motion occurs in a test subject.

When the driver 1012 is started in accordance with a command from the information processor 1020, the driver 1012 drives the LEDs 1011a and 1011b alternately at different timings, by preset sampling interval (50 msec in the present embodiment). Further, the driver 1012 controls the intensities of light emission from the LEDs 1011a and 1011b in accordance with commands from the information processor 1020.

Further, the A/D converter 1014 operates in synchronization with the light emission timing of the driver 1012 to thereby convert the pulse wave detection signal detected upon light emission from the green LED 1011a and the body motion detection signal detected upon light emission from the infrared LED 1011b into digital data. The A/D converter 1014 then provides the digital data, as biological information, to the information processor 1020.

Upon detection of body motion detection signal (upon light emission from the infrared LED 1011b), the detector 1013 amplifies a photoreception signal from the PD 1011c with an amplification factor greater than that upon detection of pulse wave detection signal (upon light emission from the green LED 1011a), such that the body motion component is further emphasized.

The information processor 1020 has a communication controller 1022 which detects cable connection to and disconnection from the connector 1003c and controls communication with the external device via the cable connected to the connector 1003c; a voltage detector 1023 which detects a voltage of the battery 1015; a microcomputer 1024, mainly having a CPU, a ROM, and a RAM, which controls the respective elements of the apparatus and performs analysis or the like on biological information detected by the information detection unit 1010; a storage unit 1025 which holds the biological information detected by the information detection unit 1010 and various information generated by the microcomputer 1024 based on the biological information; and a display controller 1026 which displays characters and figures on the display panel 1003*a* in accordance with instructions from the microcomputer 1024.

Note that at least a buffer area is ensured in the storage unit 1025 for storing the biological information supplied from the information detection unit 1010. The buffer area has a capacity to store data corresponding to or in an excessive amount to a preset FFT period (in the present embodiment, past 13 seconds or longer (=260 data or more)).

When the power of the apparatus 1001 is turned on, the microcomputer 1024 starts the information detection unit 1010. The microcomputer 1024 performs as follows: data update processing for updating data in the buffer area ensured in the storage unit 1025 each time biological information is supplied from the information detection unit 1010; analysis processing for analyzing the data stored in the storage unit 1025; barometer generation processing for obtaining pulse rate and pulse interval as barometers for evaluation of biological status in accordance with the result of analysis in the analysis processing; display processing for displaying the barometers generated in the barometer generation processing and charging status of the battery 1015 on the display panel 1003*b* via the display controller 1026; and communication processing for performing communication with the external device via the cable connected to the connector 1003*c* to transfer various data stored in the storage unit 1025, change settings of the respective elements of the apparatus 1001, and update programs executed by the microcomputer 1024, in accordance with commands inputted from the external device, and the like.

Figure 16:
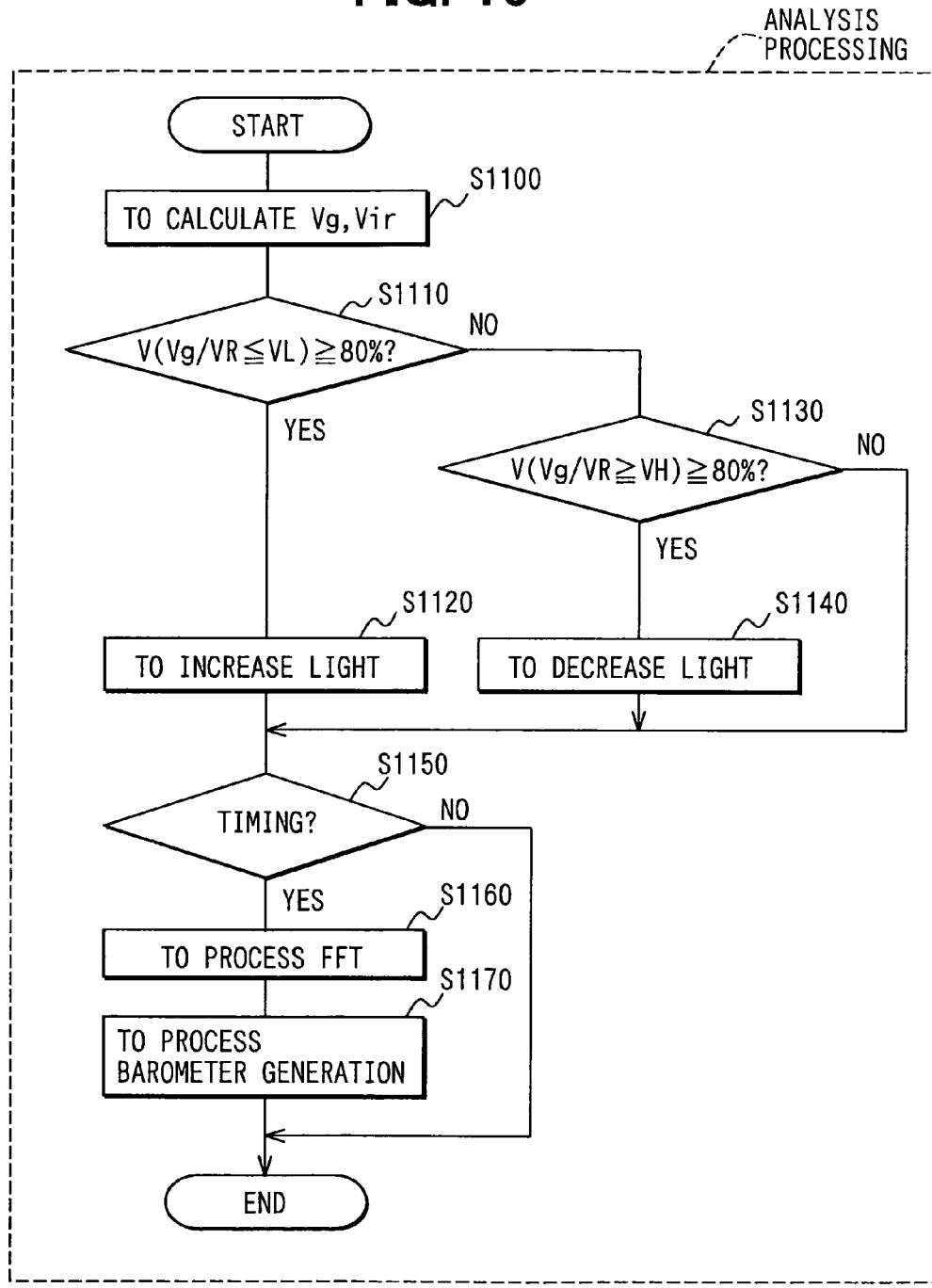
FIG. 16 is a flowchart showing the contents of analysis processing.

Hereinbelow, the details of the analysis processing and the barometer generation processing according to the present embodiment will be described. FIG. 16 is a flowchart showing the contents of the analysis processing. Note that when the information detection unit 1010 has been started, the analysis processing is started by a preset time interval (in the present embodiment, 1 second). Further, upon starting of the information detection unit 1010, the driver 1012 is initialized to a setting to cause light emission from the LEDs 1011*a* and 1011*b* at a maximum intensity.

Figure 17A:
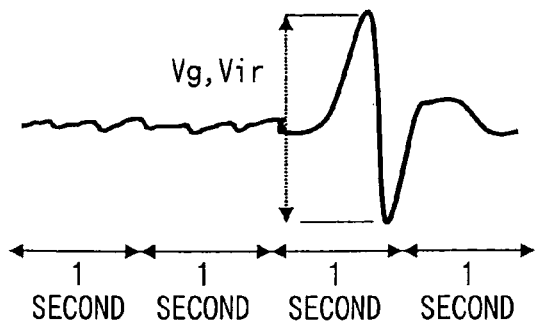
FIGS. 17A to 17C are explanatory diagrams showing parameters and the like used in the analysis processing.

When the process starts, with regard to the respective pulse wave detection signal and body motion detection signal, an amplitude Vg of the pulse wave detection signal and an amplitude Vir of the body motion detection signal are calculated based on digital data (in the present embodiment, 20 data) obtained within a unit section (i.e., 1 second) from the previous startup to the current time point (Step S1100). More particularly, as shown in FIG. 17A, a maximum value and a minimum value in the digital data obtained in the unit section are extracted, and the difference is obtained as the amplitudes Vg and Vir.

Figure 17B:

Next, with a voltage range where the pulse wave detection signal is detected as VR (see FIG. 17B), it is determined whether or not the percentage of unit sections, where Vg/VR is equal to or less than a lower limit value VL (in the present embodiment, 0.1) within a past preset period (in the present embodiment, 20 seconds), is equal to or higher than a predetermined percentage (in the present embodiment, 80%) (Step S1110). When the percentage is the predetermined or higher percentage, it is determined that the amount of light in the LEDs 1011*a* and 1011*b* are insufficient. Then a command to increase the light emission intensity is outputted to the driver 1012 (Step S1120).

On the other hand, when the determination at Step S1110 is negative, it is determined whether or not the percentage of unit sections, where Vg/VR is equal to or higher than an upper limit value (in the present embodiment, 0.7) within the past preset period, is equal to or higher than a predetermined percentage (in the present embodiment, 80%) (Step S1130). When the percentage is the predetermined or higher percentage, it is determined that the quantity of light in the LEDs 1011*a* and 1011*b* are superabundant. Then a command to decrease the light emission intensity is outputted to the driver 1012 (Step S1140).

Next, it is determined whether or not it is timing to perform the FFT processing (Step S1150). When it is not the FFT execution timing, the process ends. Note that in the present embodiment, the FFT execution timing is set to 13-second interval. However, the FFT execution timing may be an interval shorter than 13 seconds, e.g., 1-second interval (that is, the processing is performed upon every starting of the present processing), otherwise, may be an interval longer than 13 seconds.

Figure 17C:
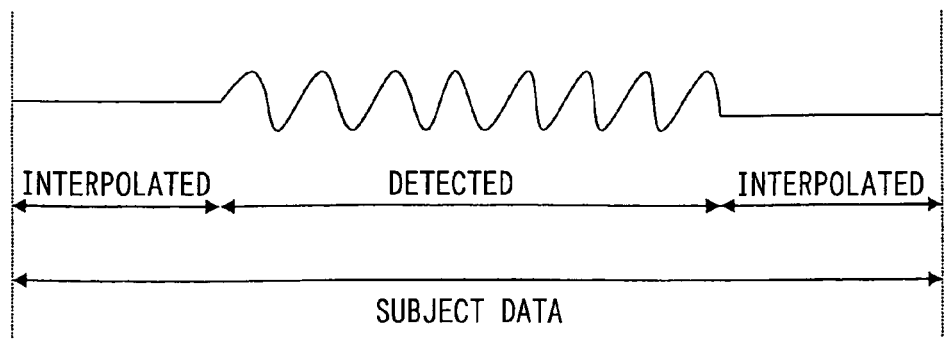

When the determination at Step S1150 is affirmative, the FFT processing is performed on the respective pulse wave detection signal and the body motion detection signal (Step S1160). Note that in the present embodiment, digital data for the FFT period (i.e., 260 data) stored in the buffer area of the storage unit 1025 are subjected to the FFT processing. As shown in FIG. 17C, upon FFT processing, interpolation data is added such that the number of data to be FFT processed becomes the power of 2 (in the present embodiment, $2^9$=512). That is, the analysis is performed with a frequency resolution higher than the actual number of data.

When the FFT processing has been completed, the pulse component is extracted based on the result of analysis, and the barometer generation processing for generating barometers indicating biological status such as a pulse rate and pulse interval is started (Step S1170). The process then ends.

That is, in the analysis processing, every time the present processing is started (i.e., by 1 second), the amplitudes Vg and Vir based on the waveform detected in the past unit section (i.e., 1 second) are obtained with regard to the pulse wave detection signal and the body motion detection signal. Further, at each FFT execution timing (i.e., by 13 seconds), the result of FFT processing is obtained based on the waveform detected in the past FFT period (i.e., 13 seconds).

Figure 18:
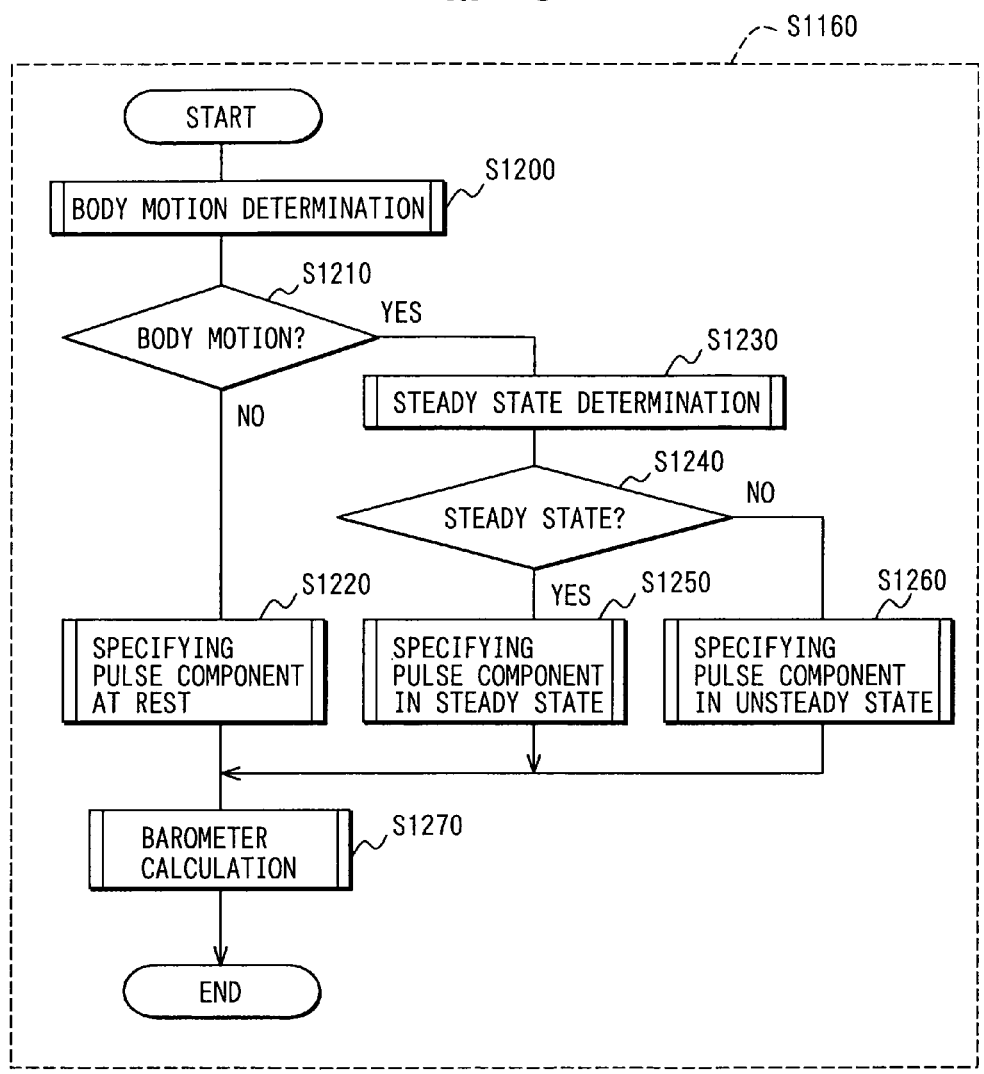
FIG. 18 is a flowchart showing the contents of barometer generation processing.

Next, the barometer generation processing started at Step S1170 will be described with reference to the flowchart of FIG. 18. When the present processing is started, first, body motion determination processing for determining the occurrence and nonoccurrence of the test subject's body motion is performed (Step S1200).

Figure 19:
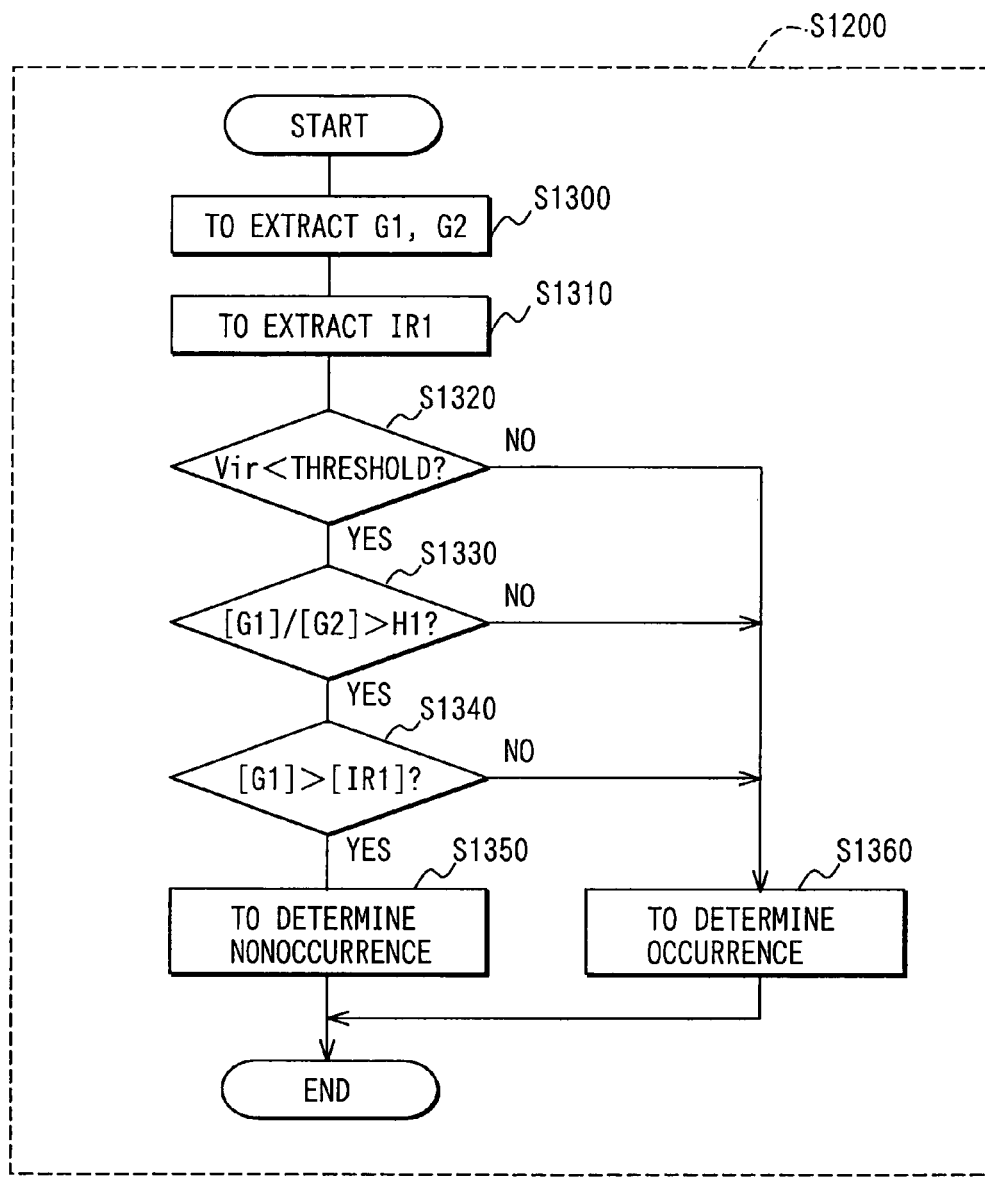
FIG. 19 is a flowchart showing the contents of body motion determination processing.

In the body motion determination processing, as shown in FIG. 19, first, a peak frequency component G1 having a maximum intensity and a peak frequency component G2 having a next maximum intensity are extracted within a frequency range including the fundamental wave of the pulse wave (in the present embodiment, 0.5 to 3.3 Hz), from the result of analysis of the pulse wave detection signal (Step S1300). Further, a frequency component IR1 having the same frequency as that of the peak frequency component G1 is extracted from the result of analysis of the body motion detection signal (Step S1310).

Then, with regard to the respective unit sections in the FFT period (past 13 seconds) used in the FFT processing on the body motion detection signal at Step S1160, it is determined whether or not the amplitude Vir in the unit section is less than a predetermined threshold value (Step S1320). When the amplitude is equal to or greater than the threshold value in even one unit section, it is determined that body motion has occurred (Step S1360), and the process ends.

Further, when the amplitude Vir is less than the threshold value in all the unit sections, it is determined whether or not the intensity ratio between the peak frequency components G1 and G2 of the pulse wave detection signal, [G1]/[G2] ([X] indicates the intensity of frequency component X), is greater than a predetermined value H1 (in the present embodiment, 10) (Step S1330). When it is determined that the intensity ratio is equal to or less than the predetermined value H1, it is considered that multiple peak frequency components having considerable sufficient intensities exist and overlap with peak frequency components based on other factor than the pulse i.e. the body motion. Accordingly, it is determined that body motion has occurred (Step S1360), and the process ends.

Further, when the intensity ratio between the peak frequency components G1 and G2, [G1]/[G2], is greater than the predetermined value H1, it is determined whether or not the intensity of the peak frequency component G1 of the pulse wave detection signal extracted at Step S1300 is higher than that of the frequency component IR1 of the body motion detection signal extracted at Step S1310 (Step S1340). When the intensity of the peak frequency component G1 is equal to or lower than that of the frequency component IR1, it is considered that the peak frequency component G1 is based on the body motion. Accordingly it is determined that body motion has occurred (Step S1360), and the process ends.

On the other hand, when the intensity of the peak frequency component G1 is higher than that of the frequency component IR1, it is determined that no body motion has occurred (Step S1350), and the process ends.

That is, it is determined that no body motion has occurred only in a case where the amplitude of the body motion detection signal is greater than the threshold value in all the sections within the FFT period, and in the result of analysis of the pulse wave detection signal, the number of peak frequency components having sufficient intensities is one ([G1]/[G2] >H1) and further the intensity of the peak frequency component is higher than that of the frequency component in the body motion detection signal having the same frequency ([G1]>[IR1]). It is determined that body motion has occurred in other cases than the above case.

Returning to FIG. 18, it is determined from the result of determination in the body motion determination processing (Step S1200) whether or not body motion has occurred (Step S1210). When it is determined that no body motion has occurred, processing for specifying pulse component at rest is performed (Step S1220). In this processing, the peak frequency component G1 of the pulse wave detection signal extracted at Step S1300 in the body motion determination processing is specified as a pulse component.

On the other hand, when it is determined that body motion has occurred in the body motion determination, steady state determination processing is performed for determining existence and absence of steady state of the body motion (Step S1230).

Figure 20:
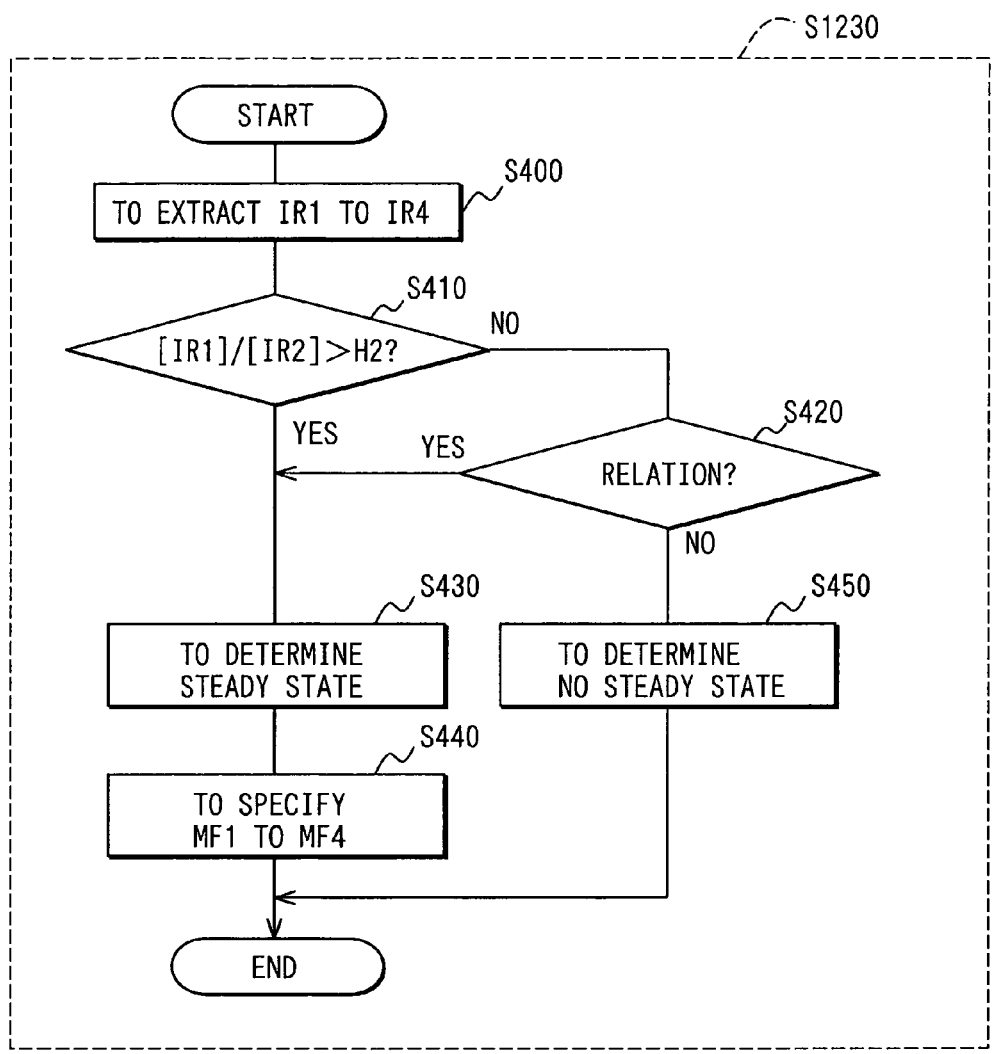
FIG. 20 is a flowchart showing the contents of steady state determination processing.

In the steady state determination processing, as shown in FIG. 20, first, four peak frequency components IR1 to IR4 are extracted from the highest intensity based on the result of analysis of the body motion detection signal (Step S1400). Then it is determined whether or not the intensity ratio between the peak frequency component IR1 having the highest intensity and the peak frequency component IR2 having the next highest intensity, [IR1]/[IR2], is greater than a predetermined value H2 (in the present embodiment, 10) (Step S1410). When the intensity ratio [IR1]/[IR2] is equal to or less than the predetermined value H2, it is determined whether or not the peak frequency component IR2 having the second highest intensity or the peak frequency component IR3 having the third highest intensity and the peak frequency component IR1 having the highest intensity are in relation of fundamental wave to second harmonic wave (Step S1420).

When it is determined at Step S1410 that the intensity ratio between the peak frequency components IR1 and IR2, [IR1]/[IR2], is greater than the predetermined value H2 or it is determined at Step S1420 that the peak frequency component IR2 or IR3 and the peak frequency component IR1 are in the relation of fundamental wave and second harmonic wave, it is determined that the body motion has a steady state (Step S1430). Further, a fundamental wave MF1 and second to fourth harmonic waves MF2 to MF4 of the body motion component are specified from the peak frequency components IR1 to IR4 (Step S1440), and the process ends.

Figure 21A:
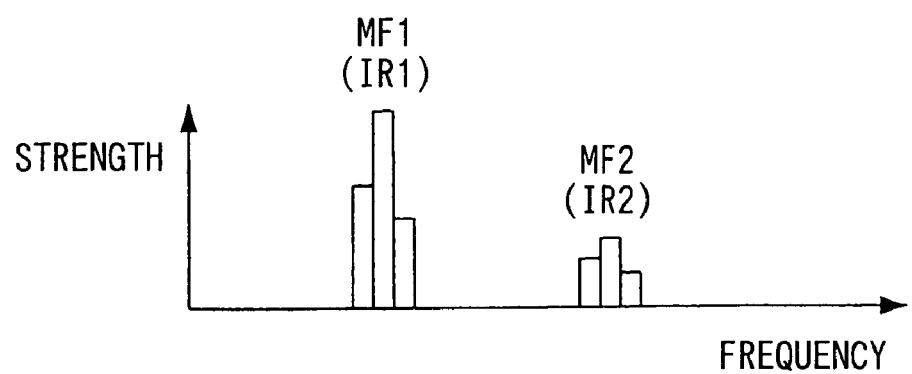
FIGS. 21A and 21B are graphs explaining the operation related to the steady state determination processing.
Figure 21B:
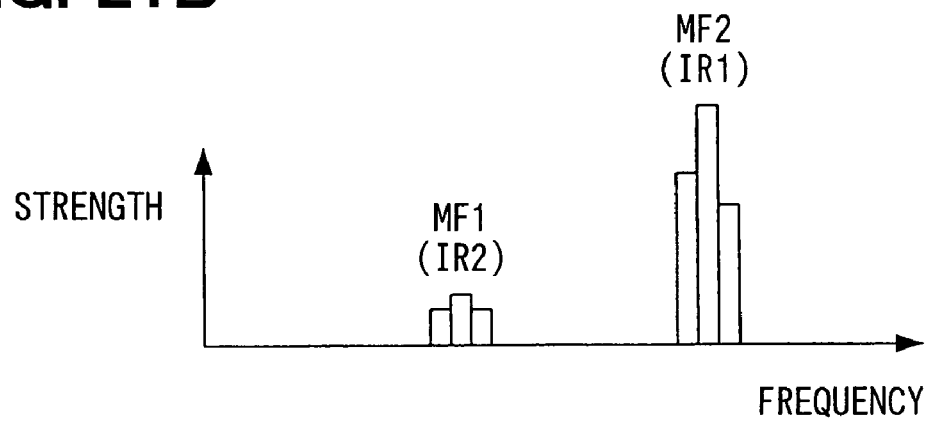

Note that when the determination at Step S1410 is affirmative, the peak frequency component IR1 is immediately specified as the fundamental wave MF1 at Step S1440. On the other hand, when the determination at Step S1420 is affirmative, as shown in FIG. 21A, the peak frequency component IR1 may be specified as the fundamental wave MF1. However, as shown in FIG. 21B, the peak frequency component IR2 or IR3 having the second or third highest intensity (in FIG. 21A, the peak frequency component IR2) may be specified as the fundamental wave MF1 and the peak frequency component IR1 having the highest intensity may be specified as the second harmonic wave.

Further, when it is determined at Step S1420 that the peak frequency component IR2 or IR3 and the peak frequency component IR1 are not in the relation of fundamental wave to second harmonic wave, it is determined that the body motion has no steady state (Step S1450), and the process ends.

That is, in the present processing, in the result of analysis of the body motion detection signal, in a case where the number of peak frequency components having sufficient intensities is one ([IR1]/[IR2]>H2), or the peak frequency components IR1 to IR4 are in the relation of fundamental wave and harmonic wave, and the peak frequency component IR1 is the fundamental wave or second harmonic wave, it is determined that the body motion has a steady state.

Returning to FIG. 18, it is determined from the result of determination by steady state determination means (Step S1230) whether or not the body motion has a steady state (Step S1240). When it is determined that the body motion has a steady state, processing for specifying pulse component in steady state motion is performed (Step S1250). On the other hand, when it is determined that the body motion has no steady state, processing for specifying pulse component in unsteady state motion is performed (Step S1260).

Figure 22:
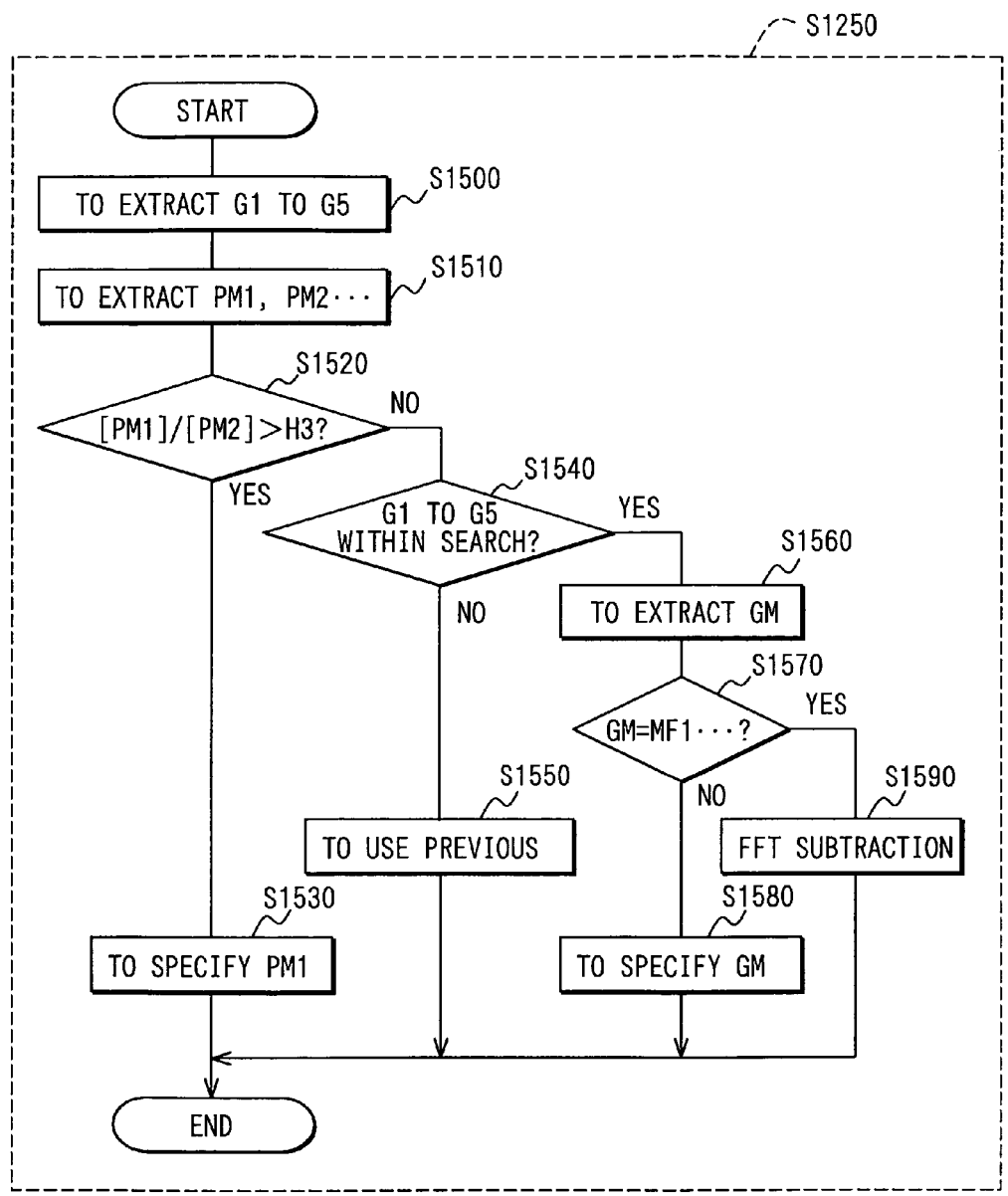
FIG. 22 is a flowchart showing the contents of processing for specifying pulse component at steady motion.

In the processing for specifying pulse component in steady state motion, as shown in FIG. 22, first, within a frequency range including a pulse wave fundamental wave, five peak frequency components G1 to G5 are extracted from the highest intensity from the result of analysis of pulse wave detection signal (Step S1500). Among the extracted peak frequency components G1 to G5, frequency components not overlapping with the body motion components MF1 to MF4 are extracted as nonoverlap peak frequency components PM1, PM2, . . . (Step S1510).

Figure 23A:
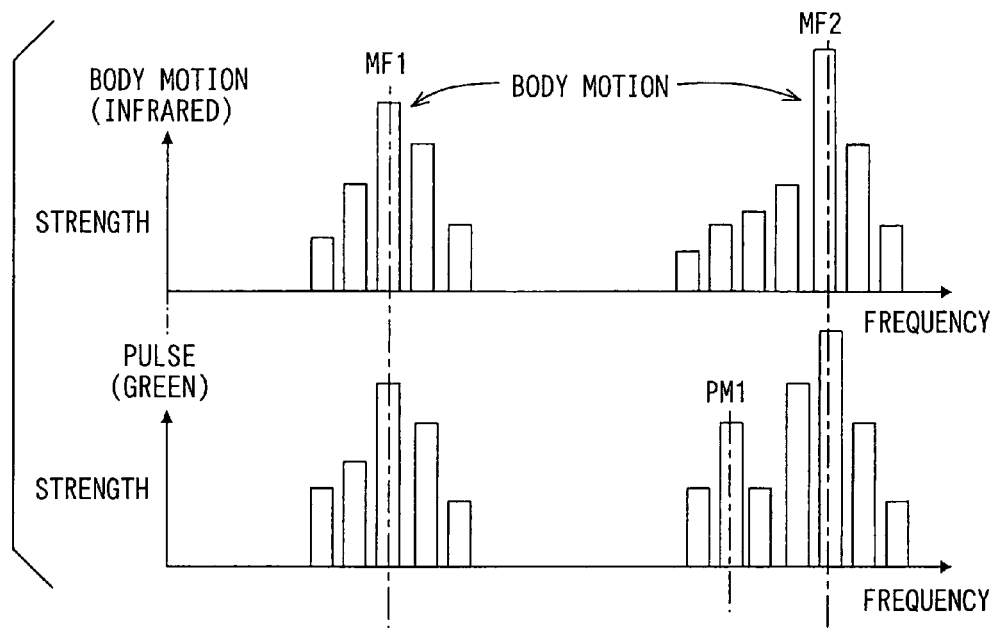
FIGS. 23A and 23B are graphs explaining the operation related to the processing for specifying pulse component at steady motion.

Then, it is determined whether or not the intensity ratio between the nonoverlap peak frequency component PM1 having the highest intensity and the nonoverlap peak frequency component PM2 having the next highest intensity, [PM1]/[PM2], is greater than a predetermined value H3 (in the present embodiment, 3) (Step S1520). When the intensity ratio [PM1]/[PM2] is greater than the predetermined value H3 or there is no nonoverlap peak frequency other than the nonoverlap peak frequency PM1, the nonoverlap peak frequency PM1 is specified as a pulse component (Step S1530), and the process ends (see FIG. 23A).

On the other hand, when the intensity ratio [PM1]/[PM2] is equal to or less than the predetermined value H3, it is determined whether or not the peak frequency components G1 to G5 exist within a search range including a frequency corresponding to the pulse rate calculated in the previous measurement (in the present embodiment, a frequency range corresponding to ±10 beats) (Step S1540). When none of the peak frequency components G1 to G5 exists in the search range, the result of previous measurement is used as the result of current measurement (pulse component) (Step Si 550), and the process ends.

Further, when at least one of the peak frequency components G1 to G5 exists in the search range, the maximum one of the components is extracted as a candidate peak frequency component GM (Step S1560). Then it is determined whether or not the candidate peak frequency component GM corresponds with any one of the body motion components MF1 to MF4 (Step S1570).

Figure 23B:
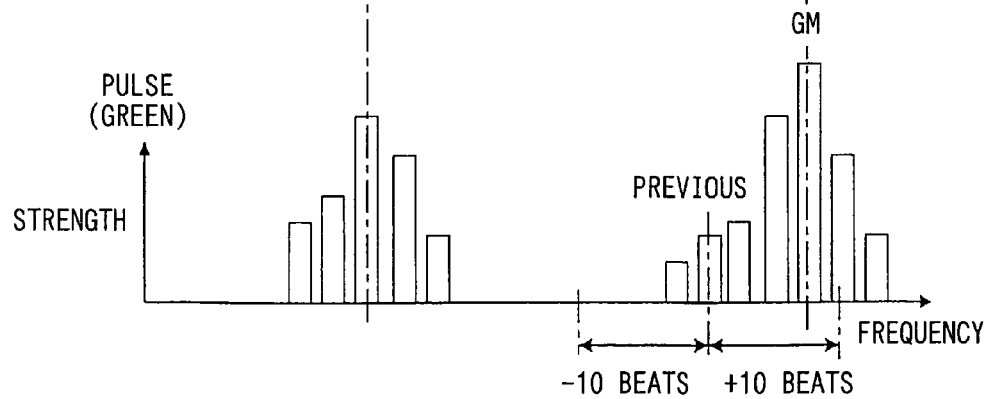

When the candidate peak frequency component GM does not corresponds with any one of the body motion components MF1 to MF4, the candidate peak frequency component GM is specified as a pulse component (Step S1580), and the process ends. Further, when the candidate peak frequency component GM corresponds with any one of the body motion components MF1 to MF4 (see FIG. 23B), a pulse component is specified by FFT subtraction processing (Step S1590), and the process ends.

Figure 24:
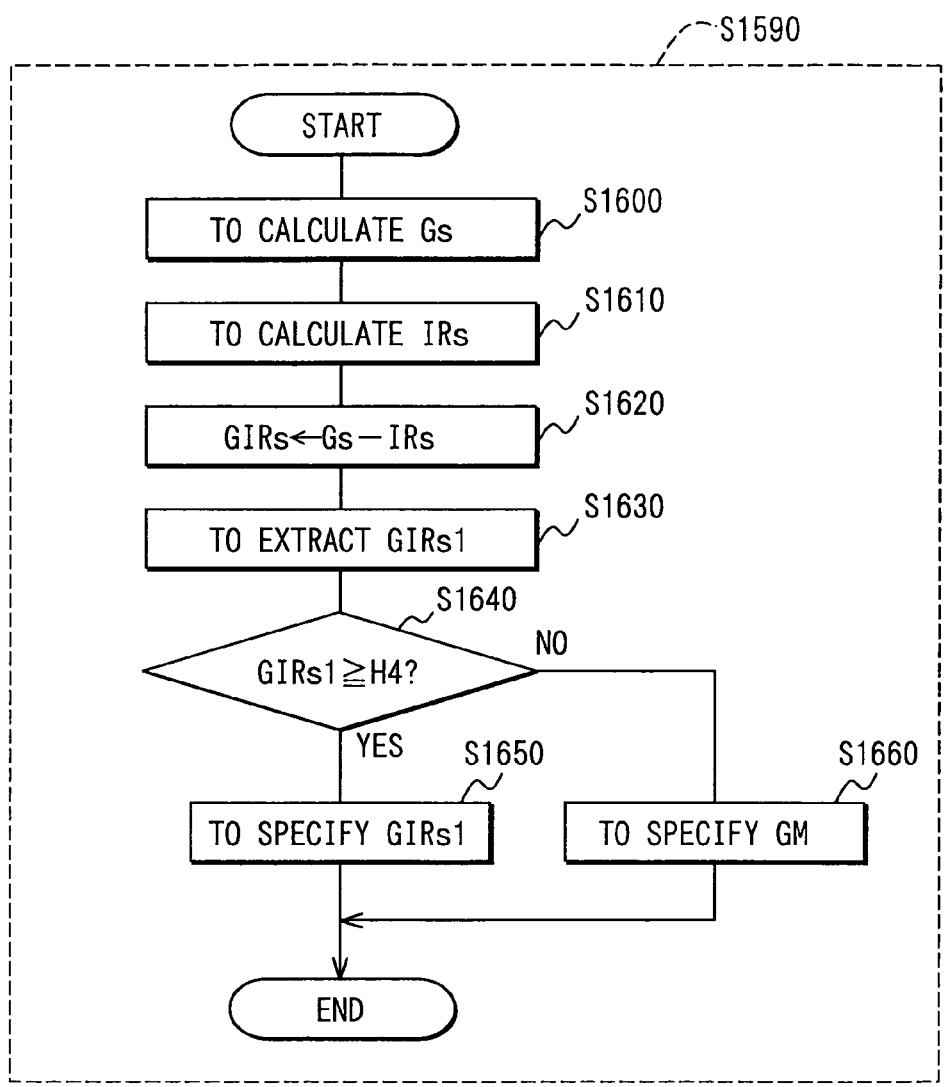
FIG. 24 is a flowchart showing the contents of FFT subtraction processing.
Figure 25A:
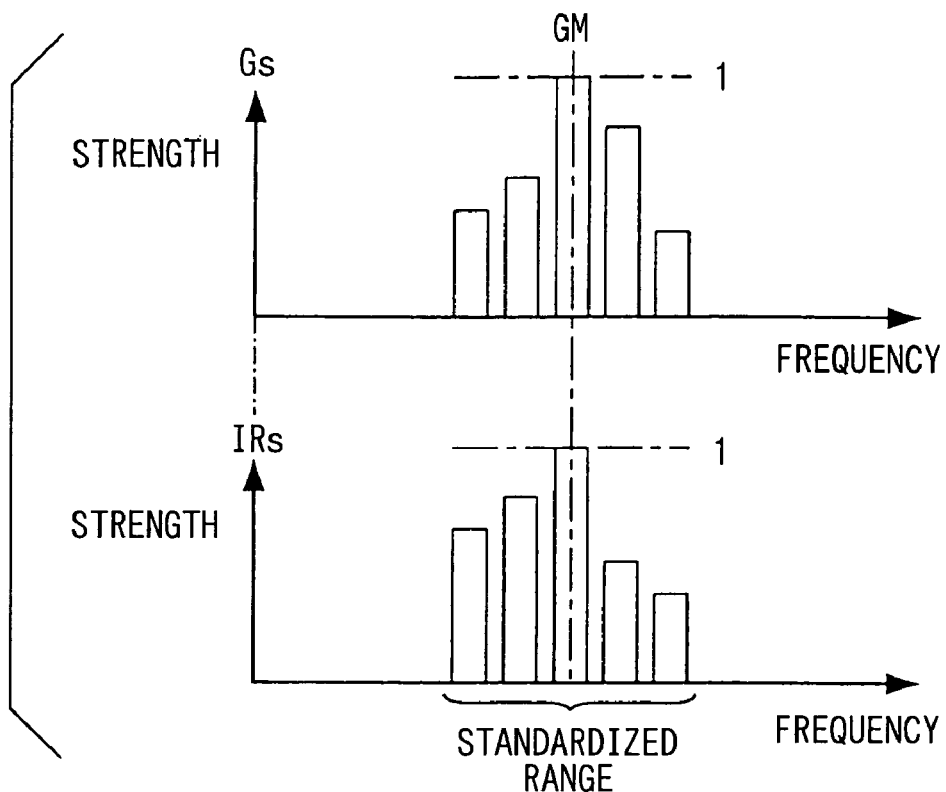
FIGS. 25A and 25B are graphs explaining the operation related to the FFT subtraction processing.
Figure 25B:

In the FFT subtraction processing at Step S1590, as shown in FIG. 24, first, from the result of analysis of pulse wave detection signal, frequency components within a predetermined range (in the present embodiment, total 11 points including 5 points on both sides) including the candidate peak frequency component GM extracted at Step S1560, as a central frequency component, are standardized such that the intensity of the candidate peak frequency component GM becomes 1 (hereinbelow, referred to as a "standardized pulse wave spectrum Gs") (Step S1600). Further, the frequency components in the above predetermined range, including a frequency component having the same frequency of that of the candidate peak frequency component GM, as a central frequency component, are standardized such that the intensity of the central frequency component becomes 1 (hereinbelow, referred to as a "standardized body motion spectrum IRs") (Step S1610). Note that regarding the standardized spectra Gs and IRs, see FIGS. 25A and 25B.

The standardized body motion spectrum IRs is subtracted from the standardized pulse wave spectrum Gs; thereby, a difference spectrum GIRs is obtained (=Gs−IR) (Step S1620). Then a peak frequency component GIRs1 in the difference spectrum GIRs (see FIG. 25B) is extracted (Step S1630).

Then it is determined whether or not the extracted peak frequency component GIRs1 is equal to or greater than a predetermined value H4 (in the present embodiment, 0.2). When the peak frequency component GIRs1 is equal to or greater than the predetermined value H4, the peak frequency component GIRs1 extracted from the difference spectrum is specified as a pulse component (Step S1650), and the process ends.

On the other hand, when the peak frequency component GIRs1 is less than the predetermined value H4, the candidate peak frequency component GM is specified as a pulse peak (Step S1660), and the process ends.

That is, when the body motion has a steady state (upon steady state motion), when a frequency component which does not overlap with the body motion components MF1 to MF4 and which has sufficiently high intensity exists among the peak frequency components extracted from the result of analysis of the pulse wave detection signal, the peak frequency component is specified as a pulse component. When such peak frequency component does not exist, a pulse component is specified based on a maximum component (candidate peak frequency component GM) among the peak frequency components in the search range presumed to include a pulse component. Especially, when the candidate peak frequency component GM overlaps with any one of the body motion components MF1 to MF4, the FFT subtraction is applied to frequency components around the candidate peak frequency component GM; thereby, a pulse component is extracted. Further, when a pulse component cannot be specified, the result of previous measurement can be employed.

Figure 26:
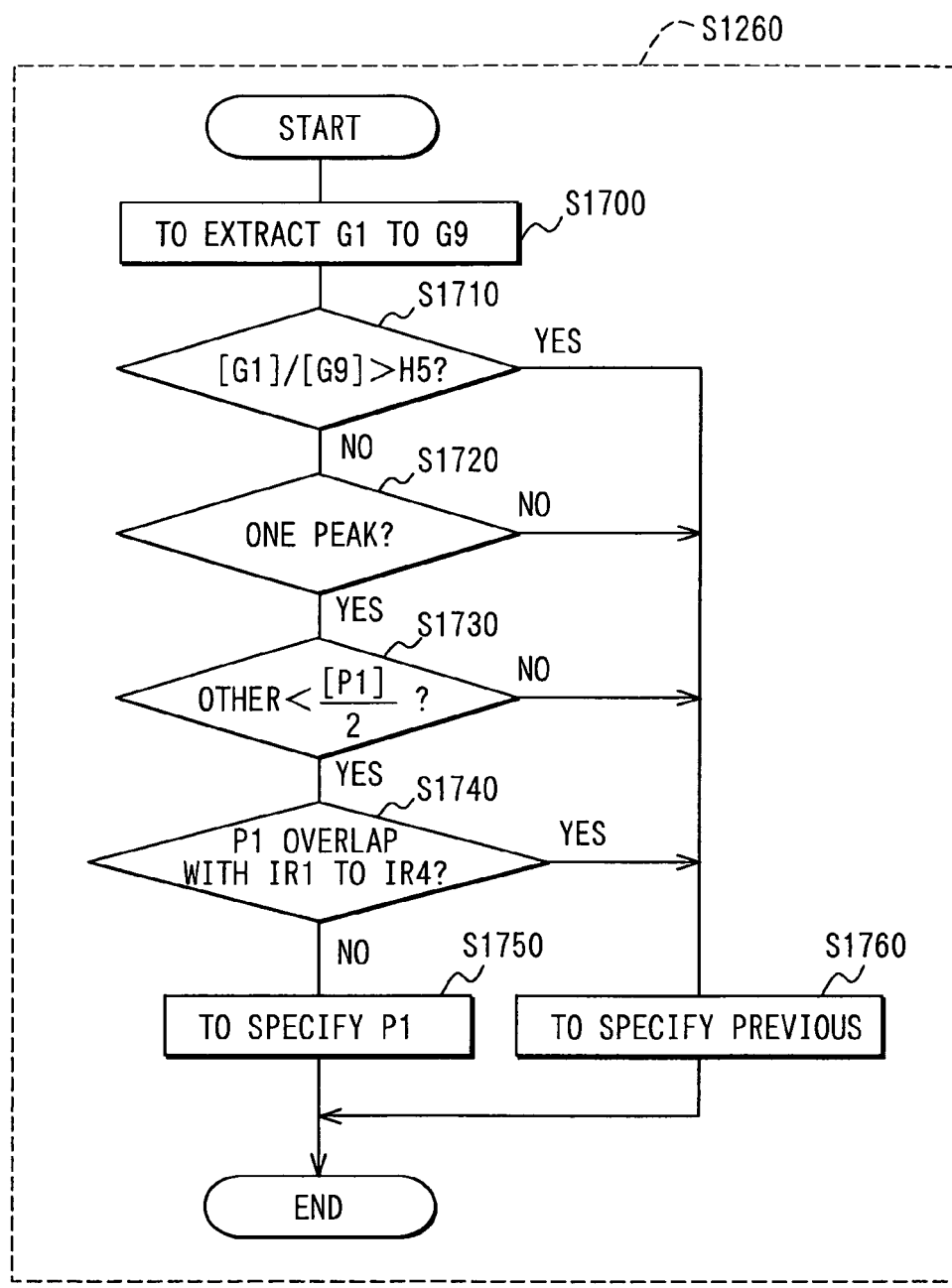
FIG. 26 is a flowchart showing the contents of processing for specifying pulse component at non-steady motion.

Next, in the processing for specifying pulse component in unsteady state motion, as shown in FIG. 26, first, from the result of analysis of pulse wave detection signal, nine peak frequency components G1 to G9 are extracted from the highest intensity within a frequency range including a pulse wave fundamental wave (Step S1700). Then it is determined whether or not the intensity ratio between the peak frequency component G1 having the highest intensity and the peak frequency component G9 having the ninth highest intensity, [G1]/[G9], is greater than a predetermined value H5 (in the present embodiment, 10) (Step S1710). When the intensity ratio is greater than the predetermined value H5, it is considered that multiple (9 or more) peak frequency components having considerable intensities exist, which may easily cause erroneous determination. Accordingly, the result of previous measurement (pulse component) is used as the result of current measurement (Step S1760), and the process ends.

Figure 27A:
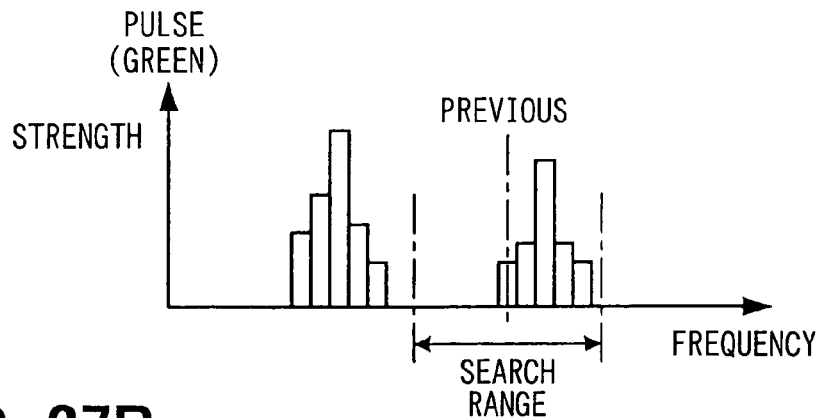
FIGS. 27A and 27B are graphs explaining operations related to the processing for specifying pulse component at non-steady motion.
Figure 27B:
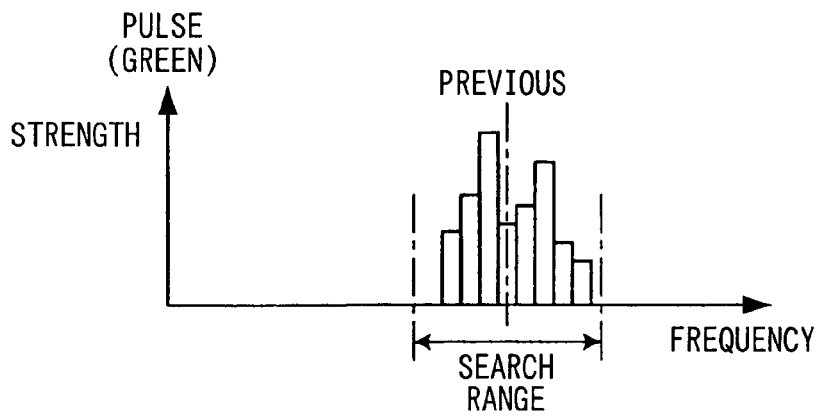

Further, when the intensity ratio [G1]/[G9] is equal to or less than the predetermined value H5, it is determined whether or not the number of peaks in the search range including a frequency corresponding to the pulse rate obtained in the previous measurement (in the present embodiment, a frequency range corresponding to ±10 beats), as a central frequency, is one (Step S1720). When multiple peaks exist in the search range (see FIG. 27B), the result of previous measurement is used as the result of current measurement (Step S1760), and the process ends.

When only one peak exists in the search range (see FIG. 27A), it is determined whether or not the intensities of other frequency components in a predetermined range (in the present embodiment, total 5 points including 2 points on both sides) including a peak frequency component P1 in the search range as a central frequency component are equal to or less than [P1]/2 (Step S1730). If even one of the frequency components is greater than [P1]/2, the peak frequency component P1 cannot be considered as a clear peak. Accordingly, the result of previous measurement is used as the result of current measurement (Step S1760), and the process ends.

When all the other frequency components are equal to or less than [P1]/2, it is determined whether or not the peak frequency component P1 overlaps any one of the body motion components IR1 to IR4 extracted at Step S1400 (Step S1740). When the peak frequency component P1 overlaps with any one of the body motion components IR1 to IR4, the possibility that the peak frequency component P1 is a pulse component is low. Accordingly, the result of previous measurement is used as the result of current measurement (Step S1760), and the process ends.

Further, when the peak frequency component P1 does not overlap with any one of the body motion components IR1 to IR4, the peak frequency component P1 is specified as a pulse component (Step S1750), and the process ends.

That is, when the body motion has no steady state (upon unsteady state motion), the peak frequency component P1 is specified as a pulse component with all the following conditions being satisfied: where the number of peak frequency components having sufficient intensities, extracted from the result of analysis of pulse wave detection signal, is comparatively small; where only one peak frequency component forming a clear peak exists in a search range presumed based on the result of previous measurement to include a pulse component; and where the peak frequency component P1 does not overlap with the body motion components IR1 to IR4.

Returning to FIG. 18, when a pulse component has been specified by the processing at Steps S1220, S1250, and S1260, barometer calculation processing for obtaining barometers such as a pulse rate and pulse interval is performed (Step S1270), and the process ends.

Figure 28:
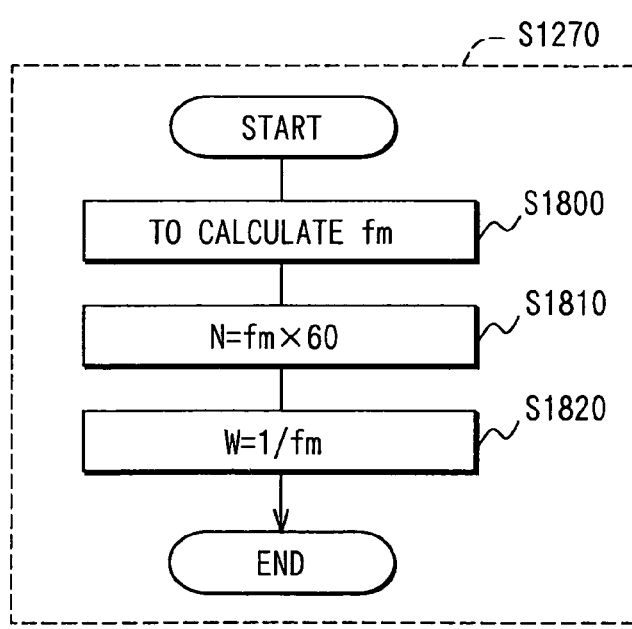
FIG. 28 is a flowchart showing the contents of barometer calculation processing.
Figure 29:
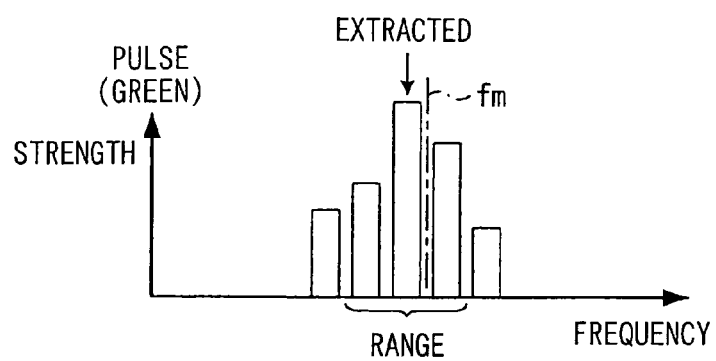
FIG. 29 is a graph explaining operations related to the barometer calculation processing.

In the barometer calculation processing, as shown in FIG. 28, first, a weighted mean frequency fm with intensity as weight is calculated based on frequency components in a predetermined range (in the present embodiment, total 3 points including 1 point on both sides) including the specified pulse component as a central component (Step S1800). Then the weighted mean frequency fm is multiplied by 60 [sec], thereby the number of pulse beats N per minute is calculated (Step S1810). Further, a reciprocal number 1/fm of the weighted mean frequency fm is obtained, thereby a pulse interval W is calculated (Step S1820), and the process ends (see FIG. 29).

Note that in this example, the number of pulse beats N and the pulse interval W are obtained as the barometers; however, it may be arranged such that when it is determined that the body motion has a steady state, a motion pitch is obtained from the fundamental wave of the body motion component.

As described above, in the biological status detection apparatus 1001 of the present embodiment, a photoreception signal from green light which is absorbed into hemoglobin by a large amount is used as a pulse wave detection signal, and a photoreception signal from infrared light which is absorbed into hemoglobin by a small amount in comparison with that in the green light is used as a body motion detection signal. Further, the light transmitting plate 1003b has a shape where the degree of adhesion to the test subject's skin is high in a portion (first portion) to transmit light emitted from the green light, while the degree of adhesion to the test subject's skin is low in a portion (second portion) to transmit infrared light when the apparatus is attached to the test subject. That is, in the pulse wave detection signal, a pulse component can be detected with high sensitivity, on the other hand, in the body motion detection signal, a body motion component can be detected with high sensitivity and detection of pulse component can be suppressed.

Further, in the LEDs 1011a and 1011b to emit green light and infrared light, the amount of light can be controlled in accordance with the amplitude of pulse wave detection signal.

Accordingly, in the biological status detection apparatus 1001 of the present embodiment, even if the apparatus 1001 is attached to a portion where the sensitivity of pulse wave detection is lower in comparison with a peripheral portion such as a finger, pulse wave and body motion can be detected with high sensitivity. Further, even if the status of attachment (the subject or position of attachment) has been changed, detection can always be performed in an appropriate status.

Further, in the biological status detection apparatus 1001 of the present embodiment, upon start of measurement, as the amount of light is set to a maximum value, the result of measurement can be reliably obtained immediately after the start of measurement.

Further, in the biological status detection apparatus 1001 of the present embodiment, as the pulse wave sensor 1011 detects a body motion detection signal as well as a pulse wave detection signal, the test subject's body motion can be detected with high accuracy without providing another body motion sensor.

Upon extraction of pulse component from the pulse wave detection signal, as the state of body motion (existence and absence of steady state motion) is determined as well as occurrence and nonoccurrence of body motion, a body motion component included in the pulse wave detection signal can be accurately specified in accordance with the result of determination. As a result, even if the test subject has had body motion, a pulse component can be extracted with high accuracy, and by extension, barometers such as the number of pulse beats N and pulse interval W can be obtained with high accuracy.

Further, in the biological status detection apparatus 1001 of the present embodiment, a weighted mean frequency is obtained based on frequency components within a predetermined range including a pulse component extracted from the result of analysis of pulse wave detection signal as a central component, and the number of pulse beats N and pulse interval W are obtained from the weighted mean frequency. Accordingly, the number of pulse beats N and pulse interval W can be obtained with a resolution seemingly higher than that of the result of analysis of FFT processing.

Further, in the biological status detection apparatus 1001 of the present embodiment, the occurrence and nonoccurrence of body motion is determined based on, not only the amplitude of the body motion detection signal, but the result of analysis of pulse wave detection signal and body motion detection signal. Here, this analysis utilizes the fact that a harmonic wave in pulse component is very low in comparison with a fundamental wave and the fact that the ratio of pulse component detection in the pulse wave detection signal and the ratio of body motion component in the body motion detection signal are different. Accordingly, the body motion can be detected with high accuracy.

Further, in a case where it is presumed that a pulse component overlaps with a body motion component, the FFT subtraction is applied to a frequency band around the portion to extract the pulse component. Accordingly, the amount of processing can be greatly reduced in comparison with conventional art using the FFT subtraction in the entire frequency range.

The second embodiment of the present invention has been described as above; however, the present invention is not limited to the above embodiment but can be implemented as various aspects.

For example, in the above embodiment, interpolation data is added to detection data in an FFT section and is used as subject data of FFT processing; however, when no body motion has occurred, as a peak frequency component can be easily extracted even if the frequency resolution is lowered, the FFT may be performed by using the detection without interpolation data. In this case, the amount of processing in the microcomputer 1024 can be greatly reduced.

Further, in the above embodiment, upon processing using the FFT subtraction (Step S1590), standardization is performed such that the intensity of peak frequency component becomes 1; however, the standardization may be performed such that mean intensities of low frequency components (e.g., 0.25 to 0.5 Hz) become equal to each other.

Further, in the above embodiment, in a case where it is presumed that a pulse component overlaps with a body motion component, the pulse component is extracted by using the FFT subtraction; however, the pulse component may be extracted by using a correlation coefficient method.

In the correlation coefficient method, the result of analysis of pulse wave detection signal and the result of analysis of body motion detection signal are divided into sections each having a predetermined frequency amplitude (e.g., 0.5 Hz), and a correlation coefficient of the results of analysis of both signals is calculated by each section. Then a section where the correlation coefficient is the minimum is extracted, and a frequency component having a highest intensity in the section is extracted as a pulse component.

Further, the extraction of pulse component may be performed by combination of multiple methods. For example, it may be arranged such that the FFT subtraction is applied to a section where the correlation coefficient is the minimum.

Further, the FFT subtraction and the correlation coefficient method may be used in the processing for specifying pulse component in unsteady state motion performed when body motion has no steady state.

Further, it may be arranged such that immediately after attachment of the biological status detection apparatus 1001 to the test subject, a message requiring bed rest is displayed on the display panel 1003a, and when the pulse rate has become stabled, measurement is started. In this case, as the pulse rate can be accurately detected in the initial stage of measurement, following performance of pulse rate upon failure of extraction of pulse component can be improved.

Third Embodiment

A third embodiment of the present invention relates to a pulse wave detection apparatus to detect a pulse wave of a living body as a test subject using a light emitting device and a photoreception device.

In recent years, portable type apparatuses to support periodical exercise such as a pedometer and a calorie consumption meter have been utilized for the purpose of precaution against life-style related diseases. To accurately determine the amount of exercise, it is effective to measure a pulse rate. For this purpose, an optical pulse wave sensor utilizing light absorption by blood component is frequently used. The optical pulse wave sensor, having a light emission device and a photoreception device, emits light from the light emission device to a human body, receives reflected light with the photoreception device, and detects a pulse wave from the changes in photoreception amount. As the optical pulse wave sensor, a well-known type of sensor is constructed such that the sensor having a light emission device and a photoreception device is fixed between the root and a second joint of human's index finger with a sensor fixing band (e.g., see WO97/037588 A1 (U.S. Pat. No. 6,241,684 B1))

However, in a case where the optical pulse wave sensor is used in the open air, sunlight noise causes a serious problem. That is, in the open air, as sunlight enters the pulse wave sensor, a pulse wave component to be detected is mixed in the sunlight noise and the pulse cannot be detected with high accuracy.

The present embodiment has been made in view of this problem, and provides a pulse wave detection apparatus to eliminate the influence of sunlight and detect a pulse wave with high accuracy.

Figure 31:
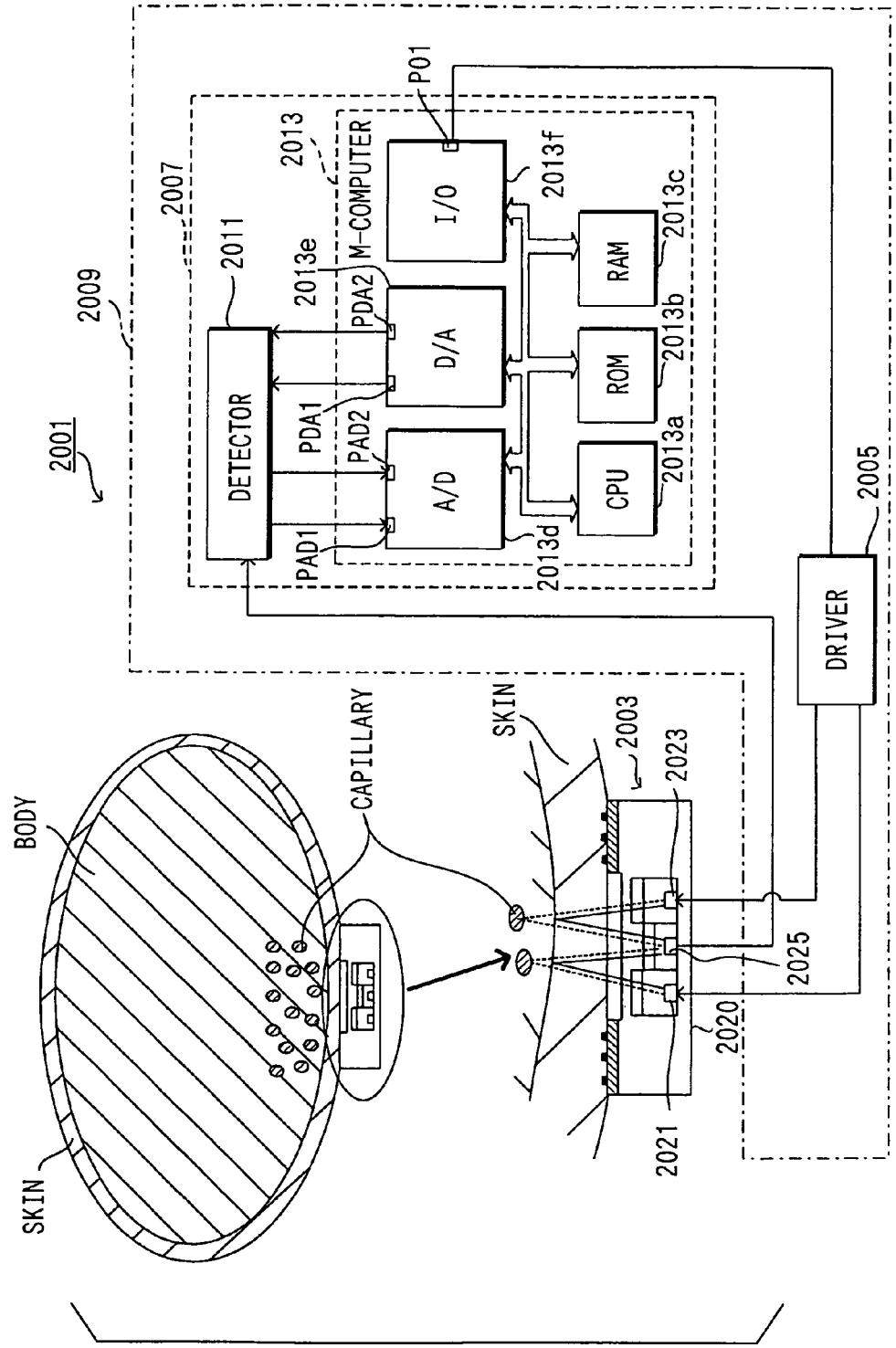
FIG. 31 is an explanatory diagram showing the principal construction of a pulse wave detection apparatus according to a third embodiment of the present invention.

A pulse wave detection apparatus 2001 according to the present embodiment detects a human body's pulse rate. As shown in FIG. 31, the pulse wave detection apparatus 2001 has a pulse wave sensor 2003 including an infrared LED 2021 and a green LED 2023 as light emission devices; a photo diode (PD) 2025 as a photoreception device; a driver 2005 which drives the pulse wave sensor 2003 by outputting driving signals to the infrared LED 2021 and the green LED 2023 to emit light at different timings; and a data processing unit 2007 which processes a signal from the pulse wave sensor 2003 and controls the driver 2005. Note that the driver 2005 and the data processing unit 2007 are accommodated in a casing of a pulse wave detection apparatus main body 2009.

Figure 32A:
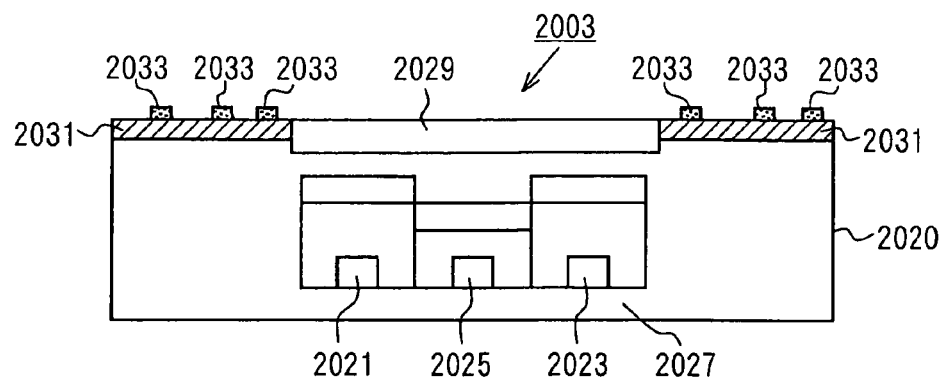
FIGS. 32A and 32B are cross-sectional view and plan view showing the structure of a pulse wave sensor.
Figure 32B:
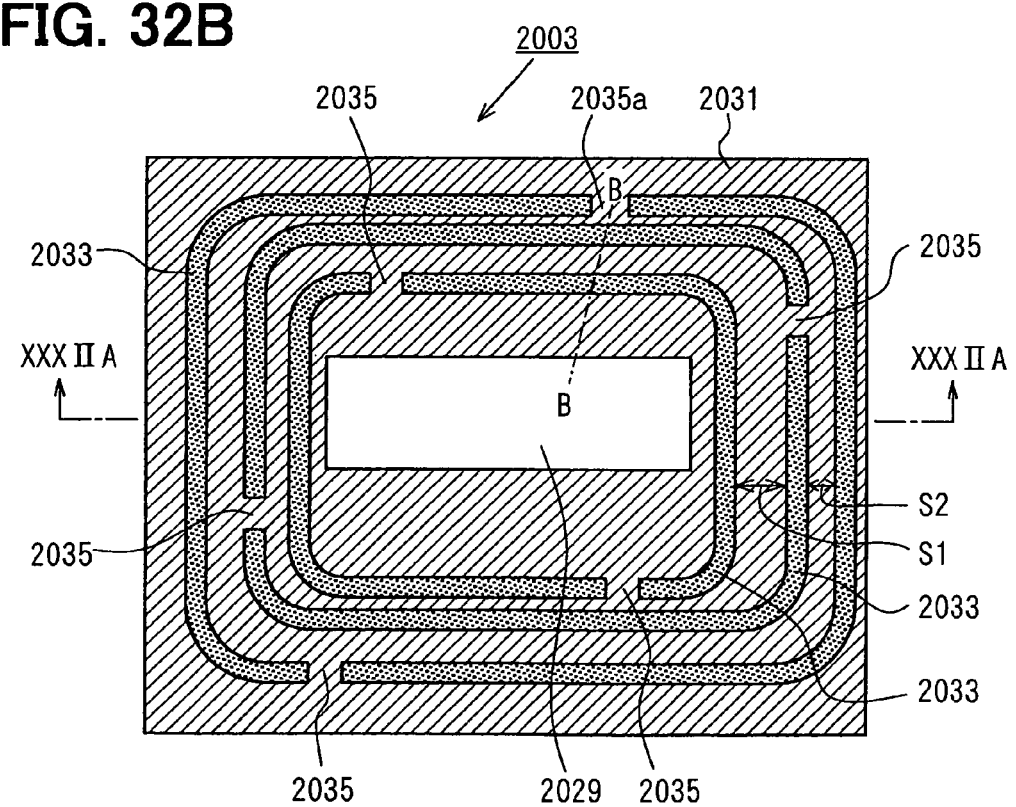

First, the construction of the pulse wave sensor 2003 will be described with reference to FIGS. 32A and 32B. FIG. 32A is a cross-sectional view showing the structure of the pulse wave sensor 2003. FIG. 32B is a plan view showing the pulse wave sensor 2003 from the side in contact with human skin.

The pulse wave sensor 2003 is fixed to human body's arm or the like when it is used. As shown in FIG. 32A, the pulse wave sensor is an optical reflective type sensor having the infrared LED 2021 to emit infrared light having a wavelength of about 940 nm, the green LED 2023 to emit green light having a wavelength of about 520 nm, and the PD 2025 to receive light and output a signal corresponding to the amount of received light (photoreception signal).

The infrared LED 2021, the green LED 2023, and the PD 2025 are arrayed in a bottom 2027 of a casing 2020 of the pulse wave sensor 2003 such that the PD 2025 is positioned between the infrared LED 2021 and the green LED 2023. Infrared light or green light is emitted to the human body via a light transmitting plate 2029. Further, a light shielding plate 2031 to block light surrounds a peripheral end of the light transmitting plate 2029. Note that as the light shielding plate 2031, a material having a flexible characteristic is used such that when the pulse wave sensor 2003 is fixed to the human body's arm or the like, the light shielding plate 2031 becomes contact with the human body's skin without gap. For example, silicon material is preferable. Further, the surface of the light shielding plate 2031 on the side in contact with the human body's skin is coated with light absorbing color (e.g., black). Note that in the figure, the light shielding plate 2031 and the casing 2020 are separate members, but the casing 2020 may be processed to have the same function as that of the light shielding plate 2031.

Further, convex members 2033 are arranged on the light shielding plate 2031 so as to surround the light transmitting plate 2029 thrice. The triple surrounding of the convex members 2033 may be changed to single, double or quadruple surrounding. Further, the height of the convex member 2033 is designed to be sufficient for causing appropriate depressed portions in the skin when the pulse wave sensor 2003 is fixed to the human body's arm or the like. For example, the height of the convex member 2033 is about 0.3 mm. As described later, the convex members 2033 are provided to prevent reception of external light in the PD 2025. Further, the convex members 2033 are multiple projection lines each having head and tail ends. A gap 2035 is formed between the both ends of each projection line for prevention of steaming. Further, the intervals among the triple layers of the convex members 2033 (e.g., see intervals S1 and S2 in FIG. 32B) are not equal but random intervals. Note that as the convex members 2033, a material having a flexible characteristic is used such that when the pulse wave sensor 2003 is fixed to the human body's arm or the like, the convex members 2033 comes to make a contact with the human body's skin without gap. For example, silicon material is preferable. In the figure, the convex members 2033, the light shielding plate 2031 and the casing 2020 are separate members, but the casing 2020 may be processed to have the same functions as those of the convex member 2033 and the light shielding plate 2031.

Further, at least one convex member 2033 is provided on a line segment (e.g., a line segment B-B) connecting the light transmitting plate 2029 and a gap (e.g., gap 2035a) formed in a position most distant from the light transmitting plate 2029.

In the pulse wave sensor 2003 having the above construction, first, as shown in FIG. 31, the light transmitting plate 2029 and the light shielding plate 2031 are brought into contact with the human body's arm skin and the pulse sensor 2003 is fixed. Thereafter, the infrared LED 2021 and the green LED 2023 alternately emit infrared light and green light to the human body, and the PD 2025 receives reflected light. Then PD 2025 outputs the change of photoreception amount as a photoreception signal (e.g., a voltage signal) to the data processing unit 2007.

Note that in the light emitted from the infrared LED 2021 and the green LED 2023 to the human body, a part of the light arrives at small artery and arteriole (capillary artery) running through the human body and is absorbed in hemoglobin in blood flowing through the capillary artery, and the rest of the light is reflected with the capillary artery and scattered. At this time, as the amount of hemoglobin in the capillary artery changes in an undulating manner due to blood pulsation, the light absorbed into the hemoglobin is also changed in an undulating manner. That is, the amount of light reflected from the capillary artery and detected by the PD 2025 changes in correspondence with the blood pulsation.

Accordingly, information on a pulse wave can be obtained from the photoreception signal outputted from the PD 2025 (corresponding to the reflected light of the light emitted from the infrared LED 2021 or the green LED 2023).

Figure 35:
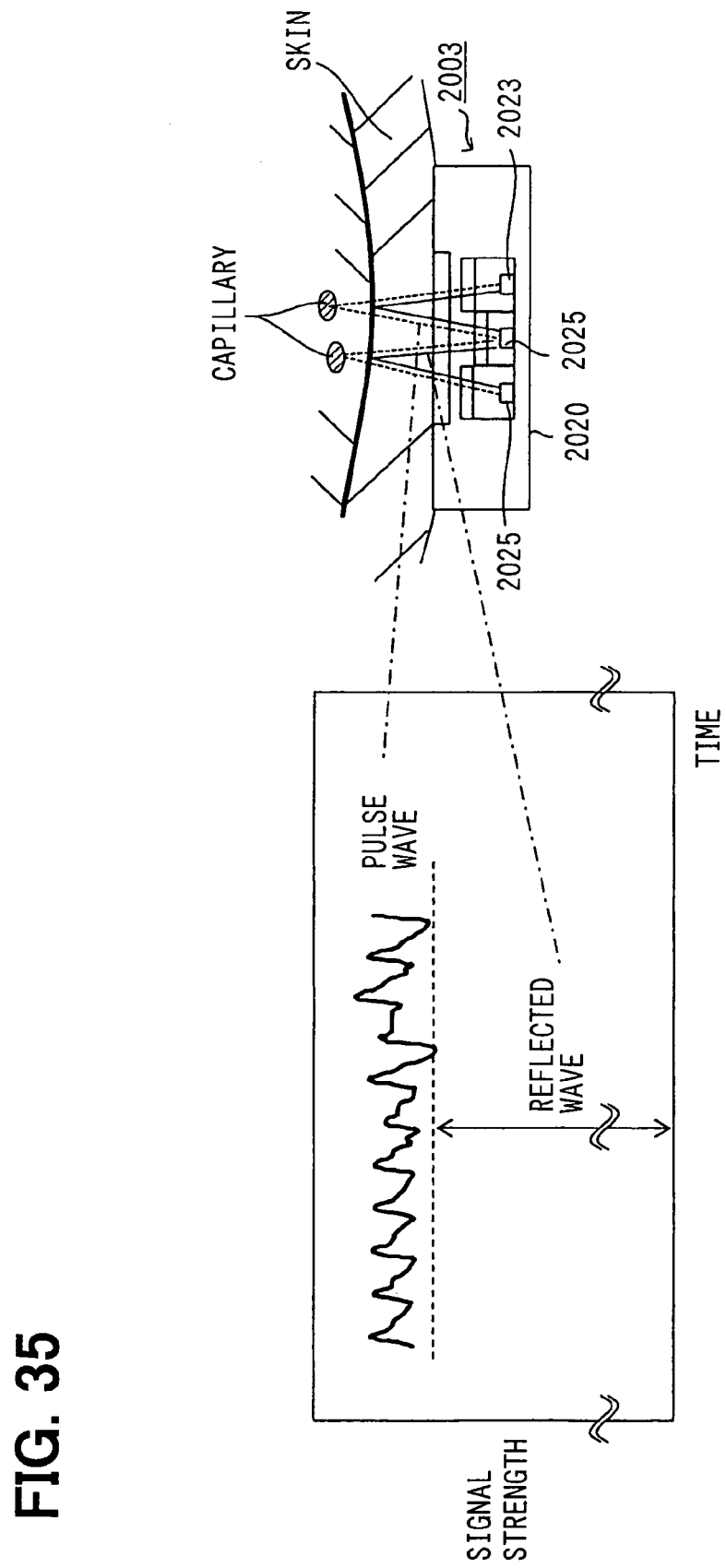
FIG. 35 is an explanatory diagram showing a photoreception signal obtained from the pulse wave sensor.

Hereinbelow, the reason of use of the infrared LED 2021 and the green LED 2023 for pulse wave detection will be described. As shown in FIG. 35, the photoreception signal outputted from the PD 2025 includes a signal indicating a pulse wave reflected from the capillary artery (pulse wave component) and a component of reflected wave from the skin surface or other portion than the capillary artery (reflected wave component). The photoreception signal is frequency-analyzed mainly to a pulse component synchronized with heartbeat, a body motion component synchronized with body motion, and approximately a direct current component (as a reflected wave component except the body motion component).

The direct current component is based on the changes in light amount accompanied by blood stream changes due to as follows: expansion and contraction of blood vessel (hereinbelow, referred to as "noise A"); the change of amount of light scattered on the skin surface accompanied by shift of the pulse wave sensor 2003 (hereinbelow, referred to as "noise B"); and the change of amount of light incident from the outside of the pulse wave sensor 2003 (e.g., sunlight) etc. The direct current component is cut with the detector 2011 using a method to be described later.

Regarding the pulse component and body motion component, the light absorption characteristics of the infrared light and green light are different. In the photoreception signal outputted from the PD 2025 upon light emission from the green LED 2023, the pulse component and the body motion component are obtained at respectively extractable signal level. By contrast, in the photoreception signal outputted from the PD 2025 upon light emission from the infrared LED 2021, the pulse component is at a very low level in comparison with the body motion component and only the body motion component is detected at an extractable signal level.

That is, the photoreception signal outputted from the PD 2025 upon light emission from the green LED 2023 (including the pulse component and the body motion component) is compared with the photoreception signal outputted from the PD 2025 upon light emission from the infrared LED 2021 (including only the body motion component); thereby, only the pulse component is extracted.

Figure 36A:
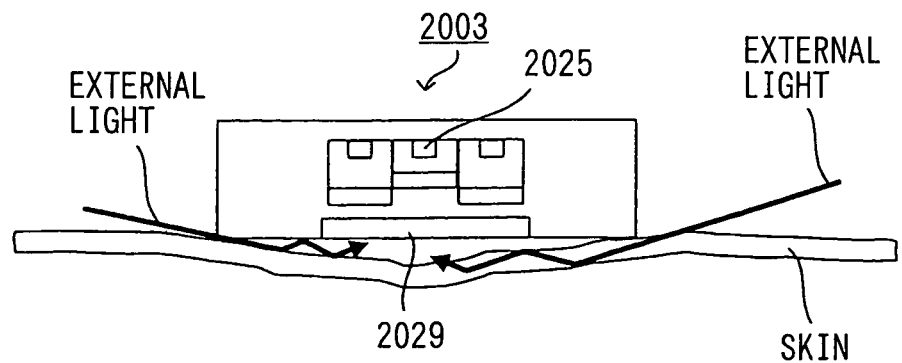
FIGS. 36A to 36C are cross-sectional views showing propagation of external light on skin surface and propagation of external light inside of the skin.
Figure 36B:
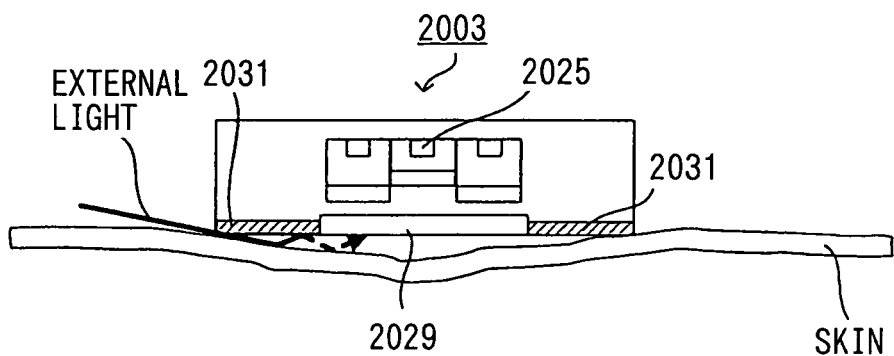

The light from the outside of the pulse wave sensor 2003 such as sunlight (hereinbelow, also referred to as "external light") is generally propagated on the skin surface and the inside of the skin and inputted into the PD 2025, as shown in FIG. 36A. As shown in FIG. 36B, a part of the external light propagated on the skin surface is absorbed in the surface of the light shielding plate 2031 coated with light absorbing color.

Figure 36C:
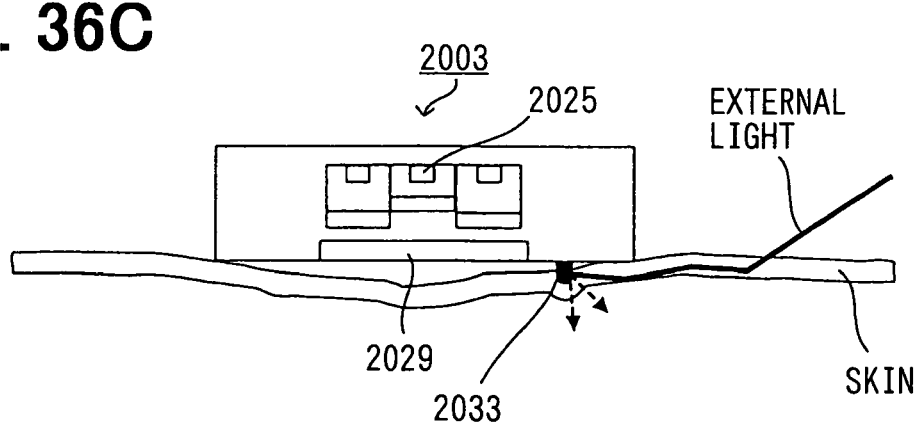

Further, the light shielding plate 2031 (in close contact with the skin) prevents formation of gap which may cause incident of external light. Further, regarding the external light propagated inside the skin, the convex members 2033 formed on the surface of the light shielding plate 2031 press the skin. As shown in FIG. 36C, as the convex members 2033 block the path of the external light propagated inside the skin, the external light is scattered with the convex members 2033.

The above arrangement can suppress the arrival of external light at the PD 2025. The data processing unit 2007 has a detector 2011 to amplify the photoreception signal obtained from the pulse wave sensor 2003 and a microcomputer 2013 to process a signal from the detector 2011 and perform various computation processings such as pulse wave detection.

Figure 33:
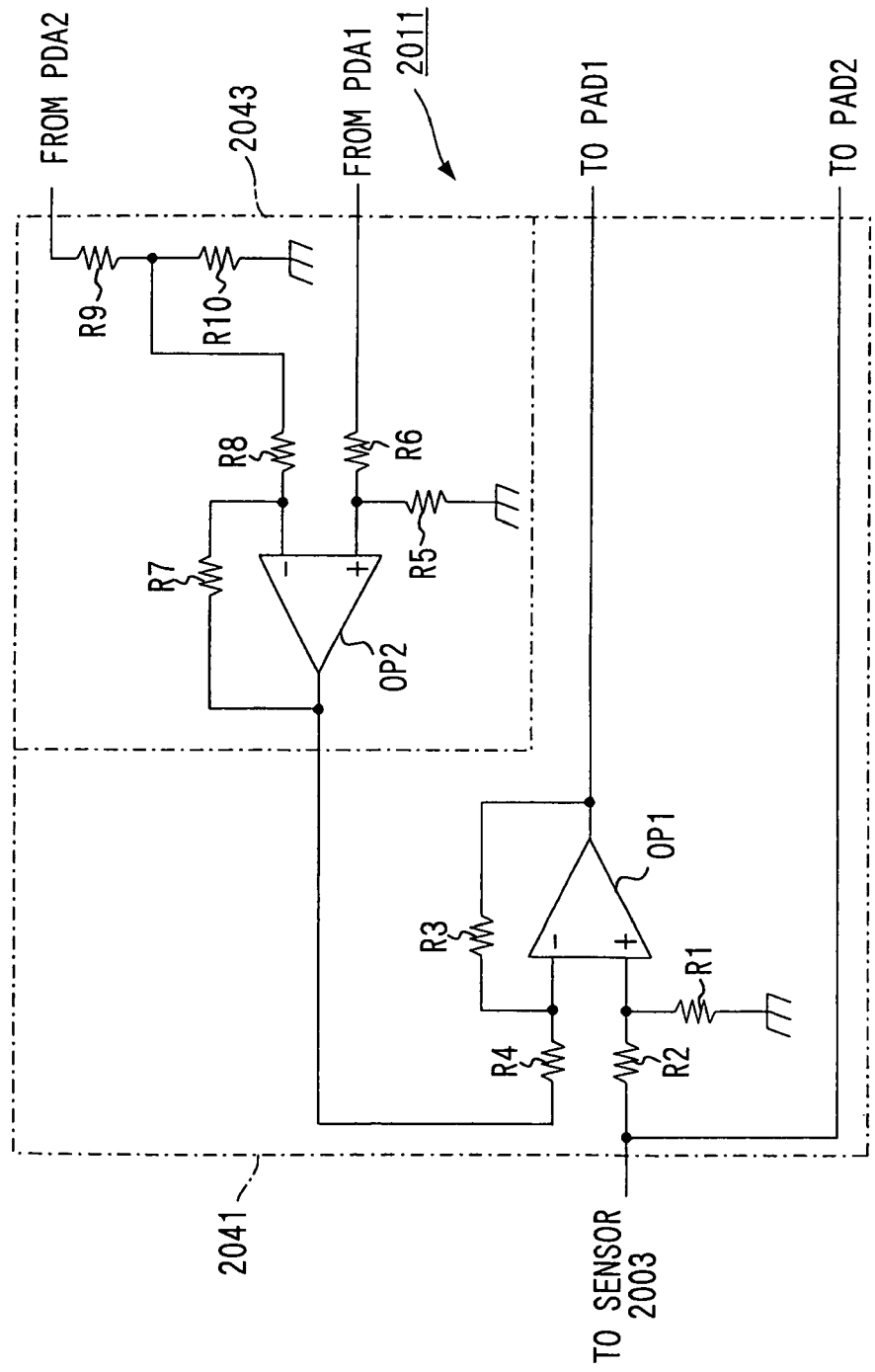
FIG. 33 is a circuit diagram showing the construction of a detector.

As shown in FIG. 33, the detector 2011 has an amplifier 2041 to amplify the photoreception signal obtained from the pulse wave sensor 2003, and a corrector 2043 to output a direct current component signal corresponding to the above-described direct current component to the amplifier 2041.

The amplifier 2041 mainly has an operational amplifier OP1. The photoreception signal from the pulse wave sensor 2003 is inputted into a non-inverting input terminal (+) of the operational amplifier OP1 via a resistor R2, and the non-inverting input terminal is grounded via a resistor R1. Further, the direct current component signal from the corrector 2043 is inputted into an inverting input terminal (−) of the operational amplifier OP1 via a resistor R4, and the inverting input terminal is connected to an output terminal of the operational amplifier OP1 via a resistor R3. Further, the output terminal of the operational amplifier OP1 is connected to an A/D port PAD1 of a 10-bit A/D converter 2013d to be described later. Further, the photoreception signal from the pulse wave sensor 2003 is also inputted into an A/D port PAD2 of the A/D converter 2013d to be described later. Note that the resistance value of the resistor R1 is equal to that of the resistor R3, and that of the resistor R2 is equal to that of the resistor R4. Further, the resistance values of the resistors R1 to R4 are set such that the amplification degree of the operation amplifier OP1 is, e.g., {(R1 resistance value)/(R2 resistance value)}=1000.

The amplifier 2041 having the above construction amplifies a signal, obtained by cutting the voltage value of the direct current component signal from the voltage value of the photoreception signal, and outputs the amplified signal.

That is, in the light emitted from the infrared LED 2021 and the green LED 2023, as the amount of light absorbed in hemoglobin is small, amplification is required for detecting the change of pulse component which appears in the photoreception signal by the A/D converter 2013d of the microcomputer 2013. In the present embodiment, about 1000 times amplification is required.

Further, as the change of direct current component is several times to several hundred times that of pulse component, when the direct current component is amplified without differentiation, the amplified signal exceeds an upper limit of voltage inputted into the A/D converter 2013d. Accordingly, the direct current component is differentiated from the photoreception signal and the signal is amplified.

The corrector 2043 mainly has an operational amplifier OP2 and voltage dividing resistors R9 and R10. A D/A port PDA2 of a 10-bit D/A converter 2013e to be described later is grounded via the voltage-dividing resistors R9 and R10. Further, a signal from a D/A port PDA1 of the D/A converter 2013e to be described later is inputted into a non-inverting input terminal (+) of the operational amplifier OP2 via a resistor R6. The non-inverting input terminal is grounded via a resistor R5. Further, an inverting input terminal (−) of the operational amplifier OP2 is connected to a connection point between the voltage dividing resistors R9 and R10 via a resistor R8, and is connected to an output terminal of the operational amplifier OP2 via a resistor R7. Note that the resistance value of the resistor R5 is equal to that of the resistor R7, and that of the resistor R6 is equal to that of the resistor R8. Further, the resistance values of the resistors R5 to R8 are set such that the amplification degree of the operation amplifier OP2 is, e.g., {(R5 resistance value)/(R6 resistance value)}=1. Further, the resistance values of the voltage dividing resistors R9 and R10 are set such that the amplification degree of the operation amplifier is, e.g., {(R9 resistance value)/(R10 resistance value )}=1024.

In the corrector 2043 having the above construction, a signal that is obtained by multiplying a voltage value (V2) of an analog signal outputted from the D/A port PDA2 by (1/1024) is inputted into the inverting input terminal (−) of the operational amplifier OP2; further, a signal having a voltage value (V1) equal to an analog signal outputted from the D/A port PDA1 is inputted into the non-inverting input terminal (+) of the operational amplifier OP2. Then an analog signal having a voltage value (V1−V2/1024) is outputted from the output terminal of the operational amplifier OP2.

That is, the resolution of the voltage value of the analog signal outputted from the output terminal of the operational amplifier OP2 is 1024 times that of the voltage value of the analog signal outputted from the D/A port PDA2.

More specifically, an analog signal having a resolution for 20 bits is outputted by using two 10-bit D/A ports. The analog signal having the voltage value V1 is outputted from the D/A port PDA1 and the analog signal having the voltage value V2 is outputted from the D/A port PDA2 such that the above value (V1−V2/1024) corresponds with the voltage value of the above-described direct component signal.

In this arrangement, input of signal exceeding an input voltage width of the A/D port PAD1 into the A/D port PAD1 can be prevented when the voltage value of the analog signal to be outputted from the D/A port PDA2 is changed by 1 bit of minimum resolution. For example, suppose that the input voltage width of the 10-bit A/D port PAD1 is 3V and that of the 10-bit D/A port PDA1, 3V when the analog signal corresponding to the direct current component signal is outputted by using only the D/A port PDA1. In this case, the minimum voltage change of the analog signal outputted from the D/A port PDA1 is 3 mV. Here, further supposing that the amplification factor of the operational amplifier OP1 is 1000 times as in the above, the output change in the operational amplifier OP1 by the 3 mV voltage change of the direct current signal is 3V. That is, the output voltage from the operational amplifier OP1 exceeds the input voltage width of the A/D port PAD1 by several-bit voltage change of the direct current component signal outputted from the D/A port PDA1.

On the other hand, in the present embodiment, as an analog signal having resolution for 20 bits is outputted as a direct component signal, assuming that the output voltage width is 3V, the minimum voltage change is about 3 μV, and the output change of the operational amplifier OP1 due to the minimum voltage change is about 3 mV. That is, the output voltage from the operational amplifier OP1 does not exceed the input voltage width of the A/D port PAD1 by several-bit voltage changes of the direct current component signals outputted from the D/A ports PDA1 and PDA2.

In the detector 2011 having the above construction, the photoreception signal with the voltage value of the direct component signal as offset is amplified while the voltage value of the direct current component signal is controlled in accordance with the analog signal from the D/A converter 2013e, and the amplified signal is outputted to the A/D converter 2013d.

As shown in FIG. 31, the microcomputer 2013 has a CPU 2013a which performs processing based on predetermined processing programs, a ROM 2013b in which various control programs are stored, a RAM 2013c in which various memories for storing various data are provided, an A/D converter 2013d which converts a voltage value of analog signal into 10-bit digital value, a D/A converter 2013e which converts the 10-bit digital data generated by the CPU 2013a into an analog signal, and an input/output port 2013f having multiple input ports to input various digital signals and multiple output ports to output various digital signals.

Note that as shown in FIG. 31, the A/D converter 2013d has the A/D ports PAD1 and PAD2 to input analog signals, and the D/A converter 2013e has the D/A ports PDA1 and PDA2 to output analog signals. Further, as shown in FIG. 31, the input/output port 2013f has an output port PO1. A driver 2007 is connected to the output port PO1.

In the microcomputer 2013 having the above construction, the CPU 2013a performs processing for outputting a signal having a component corresponding to the above noise A and noise B from the above-described direct current component signal, and processing for outputting a signal having a component corresponding to external light.

First, the processing for outputting a signal having a component corresponding to the noise A and the noise B will be described. The frequency of voltage fluctuation of photoreception signal due to the noise A and the noise B is sufficiently low in comparison with a pulse component, and the voltage fluctuation due to these noises is small in a short period. Accordingly, the CPU 2013a analyzes the voltage fluctuation of photoreception signal within each predetermined period (e.g., 10 seconds), thereby controls output values in the D/A ports PDA1 and PDA2 in correspondence with the voltage fluctuation due to the noise A and the noise B. Thus direct current component signal corresponding to the noise A and the noise B is outputted from the corrector 2043. That is, the voltage value of the direct current component can be controlled by each time.

Figure 34:
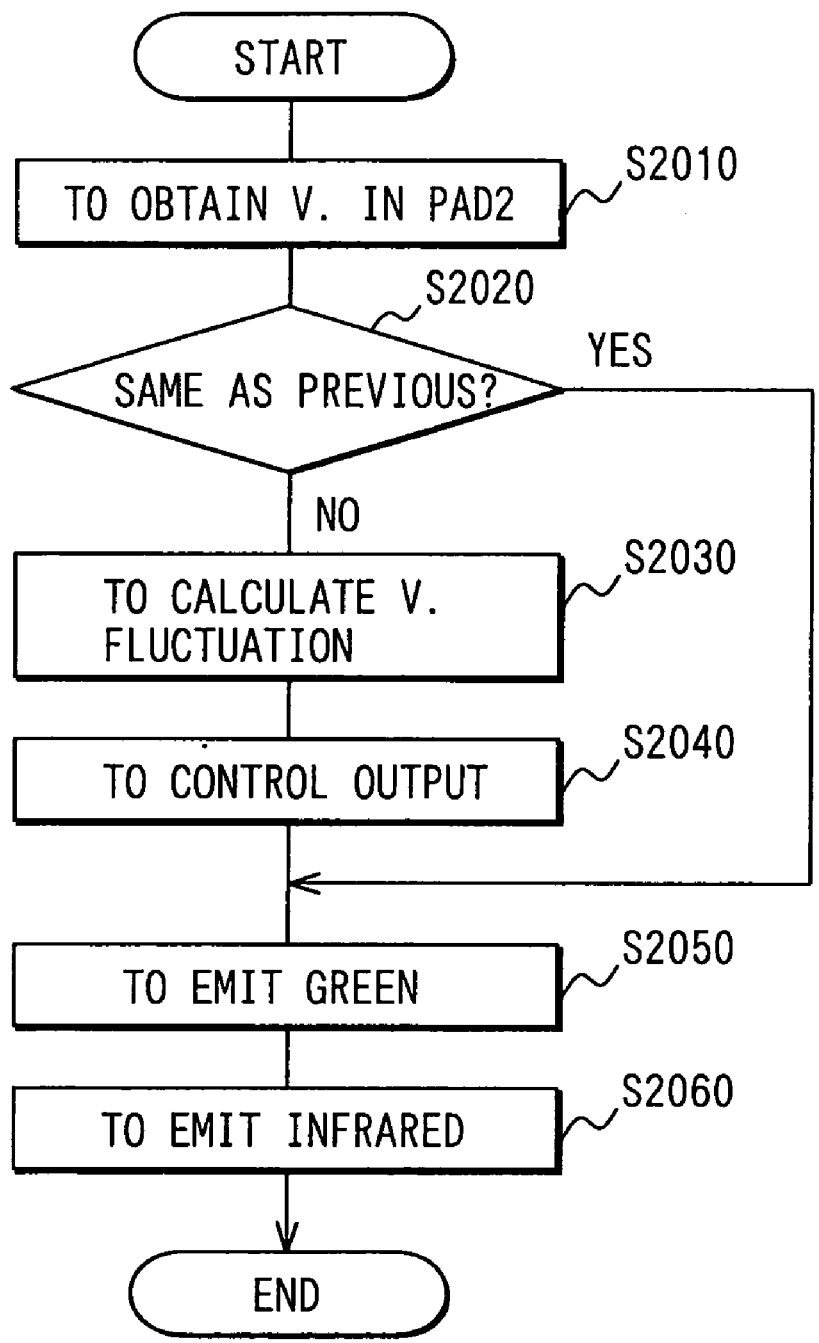
FIG. 34 is a flowchart showing a procedure of external light control processing.

Next, external light control processing for outputting a signal having a component corresponding to the external light (hereinbelow, referred to as a "external light reception signal") will be described with reference to FIG. 34. FIG. 34 is a flowchart showing the external light control processing. The external light control processing is repeatedly performed upon each light emission from the infrared LED 2021 and the green LED 2023 while the CPU 2013a is activated (power ON).

In the external light control processing, first, at Step S2010, the CPU 2013a obtains data on the voltage value of signal inputted in the A/D port PAD2. Then at Step S2020, it is determined whether or not the voltage value data obtained at Step S2010 is the same as the voltage value data previously obtained from the A/D port PAD2. When it is determined that the currently obtained voltage value data is the same as the previously obtained data (Step S2020: YES), the process proceeds to Step S2050. On the other hand, when it is determined that the currently obtained voltage value data is not the same as that previously obtained data (Step S2020: NO), the process proceeds to Step S2030.

At Step S2030, the voltage fluctuation in the output from the D/A ports PDA1 and PDA2 is calculated based on a difference value between the voltage value obtained at Step S2010 and the previously obtained voltage value. Further, at Step S2040, present output values in the D/A ports PDA1 and PDA2 are controlled in correspondence with the voltage fluctuation calculated at Step S2030. Thereafter, the process proceeds to Step S2050.

At Step S2050, light emission from the green LED 2023 is performed, and data on voltage value of signal inputted into the A/D port PAD1 is obtained. Further, at Step S2060, light emission from the infrared LED 2021 is performed, and data on voltage value of signal inputted into the A/D port PAD 1 is obtained, and the external light controlling processing ends.

That is, in the external light control processing, a photoreception signal from the PD 2025 when the infrared LED 2021 and the green LED 2023 do not emit light is regarded as an external light reception signal, and voltage values of analog signals outputted from the D/A ports PDA1 and PDA2 are controlled in correspondence with the voltage value of the external light reception signal.

In the pulse wave detection apparatus 2001 having the above construction, immediately before light emission from the green LED 2023, light received by the PD 2025 is detected as an external light reception signal (Step S2010), and the external light reception signal is outputted (Step S2020 to Step S2040). Then, light emission is performed in the green LED 2023 then in the infrared LED 2021. Then differentiation is performed between a photoreception signal, outputted from the PD 2025 upon light emission from the green LED 2023 or the infrared LED 2021, and the external light reception signal in the amplifier 2041, and a differentiated signal is obtained (Step S2050 to Step S2060); thereby, a pulse wave is detected.

As the human body's pulse wave can be detected in consideration of light component due to external light in photoreception signal upon light emission from the infrared LED 2021 or the green LED 2023, the influence of external light can be eliminated and the pulse wave can be detected with high accuracy.

Further, the signal from which the influence of external light is eliminated can be obtained by simple calculation of differentiation of external light reception signal from the photoreception signal.

Further, as the external light reception signal is detected when the light emission from the infrared LED 2021 and the green LED 2023 is stopped, the external light can be detected without influence of light emitted from the infrared LED 2021 or the green LED 2023.

Further, as the external light reception signal is detected immediately before light emission from the green LED 2023, the influence of external light inputted into the PD 2025 upon light emission from the infrared LED 2021 and the green LED 2023 can be eliminated with high accuracy. At this time, light emission may be started from the green LED 2023 or the infrared LED 2021.

Further, the pulse wave detection apparatus 2001 of the present embodiment is used when the pulse wave sensor 2003 is fixed on the human body's skin; further, the surface of the light shielding plate 2031 in contact with the skin is coated with light absorbing color. Accordingly, when external light incident from a gap formed between the light shielding plate 2031 and the skin arrives at the light shielding plate 2031, the external light is absorbed into the light shielding plate 2031; thus, reception of external light by the PD 2025 can be suppressed.

Further, as multiple convex members 2033 are arranged to surround the light transmitting plate 2029 on the surface of the light shielding plate 2031 on the side in contact with the skin, the convex member 2033 blocks the path of external light propagated inside the skin; thereby, the external light is scattered by the convex member 2033. Thus the reception of external light by the PD 2025 can be suppressed. Note that as the number of convex members 2033 is increased, many convex members 2033 are arranged on paths of external light propagated inside the skin to the PD 2025; thereby, the reception of external light by the PD 2025 can be suppressed.

Further, as the multiple convex members 2033 are arranged at random intervals, the convex members 2033 are arranged on the paths of external light propagated inside the skin, at intervals not corresponding with an integral multiple of external light frequency. Thus the photoreception of external light by the PD 2025 can be suppressed.

Further, as the convex members 2033 are projection lines each having head and tail ends, the air in a gap between the pulse wave sensor 2003 and the skin and the air outside the pulse wave sensor 2003 can be easily circulated via the gap 2035 formed between the points of projection line. That is, steaming which easily occurs in a portion where the pulse wave sensor 2003 and the skin are in close contact can be suppressed.

Further, at least one convex member 2033 is provided on a line segment (e.g., a line segment B-B) connecting a gap 2035a formed in a position most distant from the light transmitting plate 2029 and the light transmitting plate 2029. Even if external light is incident from the gap 2035a, the photoreception of external light by the PD 2025 can be thereby suppressed.

Further, as the material of the light shielding plate 2031 and the convex member 2033, silicon material having a flexible characteristic is used such that the light shielding plate 2031 comes to make a contact with the human body's skin without gap when the pulse wave sensor 2003 is fixed to the human body's skin. Accordingly, a gap as a cause of incidence of external light is not formed, and the photoreception of external light by the PD 2025 can be suppressed.

The third embodiment of the present invention has been described as above; however, the present invention is not limited to the above embodiment but various aspects can be made.

For example, in the above embodiment, the surface of the light shielding plate 2031 on the side in contact with the skin is coated with light absorbing color. However, a material having light absorbing characteristic (e.g., resin or rubber material) may be use as the material of the light shielding plate 2031. In this case, when external light incident from a gap formed between the light shielding plate 2031 and the skin arrives at the light shielding plate, the external light is absorbed into the light shielding plate 2031; thus, the photoreception of external light by the PD 2025 can be suppressed.

Further, the surface of the light shielding plate 2031 on the side in contact with the skin may have rough unevenness so as not to be regarded as a mirror finished surface. In this case, when external light incident from a gap formed between the light shielding plate 2031 and the skin arrives at the light shielding plate 2031, the external light is scattered. Thus the photoreception of external light by the PD 2025 can be suppressed.

Further, in the above embodiment, sunlight enters as the external light; however, any other light than sunlight may be handled as external light as long as the light is incident from the outside the pulse wave sensor 2003. For example, light emitted from a fluorescent lamp may be handled as external light.

Further, in the above embodiment, silicon material is used as the material of the light shielding plate 2031 and the convex members 2033. However, any other material than silicon material may be employed as long as it has a flexible characteristic such that it becomes in contact with the skin without gap upon fixing of the pulse wave sensor 2003 to the human body's arm or the like. For example, rubber, cloth, or gel solid material may be employed.

Further, in the above embodiment, the light shielding plate 2031 and the convex members 2033 are separate members from the casing 2020, but the they may be integrally formed with each other as the same member to attain similar advantage.

Further, in the above embodiment, the gap 2035 is formed in the convex members 2033; however, the convex member 2033 may have a ring shape without gap 2035.

It will be obvious to those skilled in the art that various changes may be made in the above-described embodiments of the present invention. However, the scope of the present invention should be determined by the following claims.

What is claimed is:

1. A portable biological information monitor apparatus which is adapted to be attached to a body of a test subject when it is used, comprising:
    biological information detection means for repeatedly detecting biological information reflecting at least two of (i) pulse, (ii) body motion, and (iii) autonomic nervous function of the test subject;
    barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and
    storage means for storing the barometer generated by the barometer generation means,
    wherein the barometer generation means changes timing for generation of the barometer in accordance with the generation mode,
    wherein the barometer generation means changes a time interval for generation of the barometer in accordance with the generation mode,
    wherein the biological information detection means includes an optical pulse wave sensor to detect a pulse wave by utilizing a light absorbing characteristic of a blood component.

2. The portable biological information monitor apparatus according to claim 1, further comprising:
    evaluation means for evaluating the test subject's status based on the barometer generated by the barometer generation means.

3. The portable biological information monitor apparatus according claim 2,
    wherein the evaluation means includes individual action evaluation means for evaluating the test subject's status in each generation mode.

4. The portable biological information monitor apparatus according to claim 3,
    wherein the individual action evaluation means performs evaluation by using barometers generated in a predetermined period from all the barometers generated in a generation mode subjected to evaluation.

5. The portable biological information monitor apparatus according to claim 3,
    wherein the evaluation means includes comprehensive evaluation means for comprehensively evaluating the test subject's status based on the result of evaluation in each generation mode obtained by the individual action evaluation means.

6. The portable biological information monitor apparatus according to claim 1,
    wherein the biological information detection means includes an optical body motion sensor to detect body motion by utilizing reflected light from a surface of the body.

7. The portable biological information monitor apparatus according to claim 1, further comprising:
    display means for displaying at least information generated in the apparatus.

8. The portable biological information monitor apparatus according to claim 7,
    wherein the storage means stores a past result, and
    wherein the displaying means displays by retrieving the past result stored by the storage means.

9. The portable biological information monitor apparatus according to claim 1, further comprising:
    communication means for performing communication with an external device.

10. A portable biological information monitor apparatus which is adapted to be attached to a body of a test subject when it is used, comprising:
    biological information detection means for repeatedly detecting biological information reflecting at least one of pulse, body motion, and autonomic nervous function of the test subject;
    barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means;
    storage means for storing the barometer generated by the barometer generation means; and action mode selection means that has a plurality of action modes including a continuous action mode and a limited action mode, the action mode selection means for actuating the biological information detection means while the action mode selection means is in one of the continuous action mode to always perform detection of the biological information and the limited action mode to perform the detection of the biological information only in a designated period, in accordance with a command from outside, wherein the barometer generation means changes timing for generation of the barometer in accordance with the generation mode.

11. The portable biological information monitor apparatus according to claim 10, further comprising:

generation mode manual selection means for, when the action mode is a limited action mode, selecting the generation mode of the barometer generation means in accordance with a command from the outside.

12. A portable biological information monitor apparatus which is adapted to be attached to a body of a test subject when it is used, comprising:

biological information detection means for repeatedly detecting biological information reflecting at least one of pulse, body motion, and autonomic nervous function of the test subject;

barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subjects status in wake based on the biological information detected by the biological information detection means;

storage means for storing the barometer generated by the barometer generation means;

action mode selection means that has a plurality of action modes including a continuous action mode and a limited action mode, the action mode selection means for actuating the biological information detection means while the action mode selection means is in one of the continuous action mode to always perform detection of the biological information and the limited action mode to perform the detection of the biological information only in a designated period, in accordance with a command from outside;

action determination means for, when the action mode is the continuous action mode, determining one of the generation modes corresponding to the test subject's action based on the barometer generated by the barometer generation means; and generation mode automatic selection means for selecting the generation mode of the barometer generation means in accordance with the result of determination by the action determination means.

13. A portable biological information monitor apparatus which is adapted to be attached to a body of a test subject when it is used, comprising:

biological information detection means for repeatedly detecting biological information reflecting at least one of pulse, body motion, and autonomic nervous function of the test subject;

barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means;

storage means for storing the barometer generated by the barometer generation means; and evaluation means for evaluating the test subject's status based on the barometer generated by the barometer generation means, wherein the evaluation means includes individual action evaluation means for evaluating the test subject's status in each generation mode, wherein the individual action evaluation means performs evaluation of sleep abnormality including at least one of arrhythmia, apnea, and hyperanakinesia, as the test subject's status in sleep, from the sleep evaluation barometer.

14. The portable biological information monitor apparatus according to claim 13, wherein the sleep evaluation barometer for evaluation of the sleep abnormality includes at least one of a mean value of a coefficient indicating nonsingular fluctuation in pulse regardless of time order, and a ratio of appearance of the coefficient equal to or greater than a predetermined threshold value.

15. A portable biological information monitor apparatus which is adapted to be attached to a body of a test subject when it is used, comprising:

biological information detection means for repeatedly detecting biological information reflecting at least one of pulse, body motion, and autonomic nervous function of the test subject;

barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and storage means for storing the barometer generated by the barometer generation means, wherein the barometer generation means changes timing for generation of the barometer in accordance with the generation mode, wherein the biological information detection means includes a biological status detection apparatus including:

a pulse wave sensor including a light emission unit to generate light being emitted to the test subject and a photoreception unit to receive reflected light from the test subject, wherein the pulse wave sensor outputs a pulse wave detection signal and a body motion detection signal, wherein the pulse wave detection signal includes a pulse component synchronized with pulse and a body motion component synchronized with body motion while the body motion detection signal includes the body motion component emphasized in comparison with the pulse wave detection signal;

analysis means for frequency-analyzing the pulse wave detection signal and the body motion detection signal outputted from the pulse wave sensor;

body motion determination means for determining occurrence and nonoccurrence of body motion based on at least a detection signal from the pulse wave sensor or the result of analysis by the analysis means;

steady state determination means for, when the body motion determination means determines that body motion occurs, determining a steady state of the body motion based on a result of analysis by the analysis means; and pulse component extraction means for extracting the pulse component from the pulse wave detection signal, based on the result of analysis by the analysis means, a result of determination by the body motion determination means, and a result of determination by the steady state determination means.

16. The portable biological information monitor apparatus according to claim 15,
wherein the light emission unit includes:
a first light emission device to emit light when the pulse wave sensor outputs the pulse wave detection signal; and
a second light emission device to emit light when the pulse wave sensor outputs the body motion detection signal.

17. The portable biological information monitor apparatus according to claim 16,
wherein the first light emission device emits light including a wavelength to cause light absorption by blood component at a higher level than that of the second light emission device.

18. The portable biological information monitor apparatus according to claim 17,
wherein the first light emission device emits light in a green area, and the second light emission device emits light in an infrared area.

19. The portable biological information monitor apparatus according to claim 16,
wherein the pulse wave sensor includes:
a casing, accommodating the light emission unit and the photoreception unit, and including an opening in a portion through which light emitted from the light emission unit and reflected light to the photoreception unit pass; and
a light transmitting plate, provided in the opening of the casing, to transmit light,
wherein in the light transmitting plate, a first portion to transmit at least emitted light based on the first light emission device is projected outward from the casing.

20. The portable biological information monitor apparatus according to claim 16,
wherein the photoreception unit is a single photoreception device.

21. The portable biological information monitor apparatus according to claim 15,
wherein the body motion determination means includes a first body motion determination means for, when amplitude of the body motion detection signal or a difference value of the body motion detection signal is greater than a preset threshold value, determining occurrence of body motion.

22. The portable biological information monitor apparatus according to claim 15,
wherein the body motion determination means includes a second body motion determination means for, when an intensity ratio between a highest peak frequency component and a second highest peak frequency component in the pulse wave detection signal, within a frequency area including a fundamental wave of the pulse component, is equal to or less than a preset ratio, determining occurrence of body motion.

23. The portable biological information monitor apparatus according to claim 15,
wherein the biological status detection apparatus further includes barometer calculation means for calculating a barometer including at least one of a pulse rate and a pulse interval based on the pulse component extracted by the pulse component extraction means.

24. A portable biological information monitor apparatus which is adapted to be attached to a body of a test subject when it is used, comprising:
biological information detection means for repeatedly detecting biological information reflecting at least one of pulse, body motion, and autonomic nervous function of the test subject;

barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and storage means for storing the barometer generated by the barometer generation means, wherein the biological information detection means includes a biological status detection apparatus including:
a pulse wave sensor including a light emission unit to generate light being emitted to the test subject and a photoreception unit to receive reflected light from the test subject, wherein the pulse wave sensor outputs a pulse wave detection signal and a body motion detection signal, wherein the pulse wave detection signal includes a pulse component synchronized with pulse and a body motion component synchronized with body motion while the body motion detection signal includes the body motion component emphasized in comparison with the pulse wave detection signal;

analysis means for frequency-analyzing the pulse wave detection signal and the body motion detection signal outputted from the pulse wave sensor;

body motion determination means for determining occurrence and nonoccurrence of body motion based on at least a detection signal from the pulse wave sensor or the result of analysis by the analysis means;

steady state determination means for, when the body motion determination means determines that body motion occurs, determining a steady state of the body motion based on a result of analysis by the analysis means; and pulse component extraction means for extracting the pulse component from the pulse wave detection signal, based on the result of analysis by the analysis means, a result of determination by the body motion determination means, and a result of determination by the steady state determination means, wherein the light emission unit includes:
- a first light emission device to emit light when the pulse wave sensor outputs the pulse wave detection signal; and
- a second light emission device to emit light when the pulse wave sensor outputs the body motion detection signal, wherein the pulse wave sensor includes:
- a casing, accommodating the light emission unit and the photoreception unit, and including an opening in a portion through which light emitted from the light emission unit and reflected light to the photoreception unit pass; and
- a light transmitting plate, provided in the opening of the casing, to transmit light, wherein in the light transmitting plate, a first portion to transmit emitted light based on the first light emission device is projected outward from the casing further than a second portion to transmit emitted light based on the second light emission device.

25. The portable biological information monitor apparatus according to claim 24, wherein in the casing, a peripheral portion of the opening is projected outward further than other portion in a surface where the opening is formed.

26. A portable biological information monitor apparatus which is adapted to be attached to a body of a test subject when it is used, comprising:

biological information detection means for repeatedly detecting biological information reflecting at least one of pulse, body motion, and autonomic nervous function of the test subject;

barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and storage means for storing the barometer generated by the barometer generation means, wherein the biological information detection means includes a biological status detection apparatus including:

a pulse wave sensor including a light emission unit to generate light being emitted to the test subject and a photoreception unit to receive reflected light from the test subject, wherein the pulse wave sensor outputs a pulse wave detection signal and a body motion detection signal, wherein the pulse wave detection signal includes a pulse component synchronized with pulse and a body motion component synchronized with body motion while the body motion detection signal includes the body motion component emphasized in comparison with the pulse wave detection signal;

analysis means for frequency-analyzing the pulse wave detection signal and the body motion detection signal outputted from the pulse wave sensor;

body motion determination means for determining occurrence and nonoccurrence of body motion based on at least a detection signal from the pulse wave sensor or the result of analysis by the analysis means;

steady state determination means for, when the body motion determination means determines that body motion occurs, determining a steady state of the body motion based on a result of analysis by the analysis means; and pulse component extraction means for extracting the pulse component from the pulse wave detection signal, based on the result of analysis by the analysis means, a result of determination by the body motion determination means, and a result of determination by the steady state determination means, wherein the body motion determination means includes third body motion determination means for, when intensity of the highest peak frequency component in the pulse wave detection signal, within the frequency area including the fundamental wave of the pulse component, is equal to or less than that of a peak frequency component in the body motion detection signal including the same frequency as that of the highest peak frequency component, determining occurrence of body motion.

27. A portable biological information monitor apparatus which is adapted to be attached to a body of a test subject when it is used, comprising:

biological information detection means for repeatedly detecting biological information reflecting at least one of pulse, body motion, and autonomic nervous function of the test subject;

barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and storage means for storing the barometer generated by the barometer generation means, wherein the biological information detection means includes a biological status detection apparatus including:

a pulse wave sensor including a light emission unit to generate light being emitted to the test subject and a photoreception unit to receive reflected light from the test subject, wherein the pulse wave sensor outputs a pulse wave detection signal and a body motion detection signal, wherein the pulse wave detection signal includes a pulse component synchronized with pulse and a body motion component synchronized with body motion while the body motion detection signal includes the body motion component emphasized in comparison with the pulse wave detection signal;

analysis means for frequency-analyzing the pulse wave detection signal and the body motion detection signal outputted from the pulse wave sensor;

body motion determination means for determining occurrence and nonoccurrence of body motion based on at least a detection signal from the pulse wave sensor or the result of analysis by the analysis means;

steady state determination means for, when the body motion determination means determines that body motion occurs, determining a steady state of the body motion based on a result of analysis by the analysis means; and pulse component extraction means for extracting the pulse component from the pulse wave detection signal, based on the result of analysis by the analysis means, a result of determination by the body motion determination means, and a result of determination by the steady state determination means, wherein the steady state determination means includes first steady state determination means for, when an intensity ratio between a highest peak frequency component and a second highest peak frequency component in the body motion detection signal is higher than a preset ratio, determining the steady state of the body motion.

28. A portable biological information monitor apparatus which is adapted to be attached to a body of a test subject when it is used, comprising:

biological information detection means for repeatedly detecting biological information reflecting at least one of pulse, body motion, and autonomic nervous function of the test subject;

barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and storage means for storing the barometer generated by the barometer generation means, wherein the biological information detection means includes a biological status detection apparatus including:

a pulse wave sensor including a light emission unit to generate light being emitted to the test subject and a photoreception unit to receive reflected light from the test subject, wherein the pulse wave sensor outputs a pulse wave detection signal and a body motion detection signal, wherein the pulse wave detection signal includes a pulse component synchronized with pulse and a body motion component synchronized with body motion while the body motion detection signal includes the body motion component emphasized in comparison with the pulse wave detection signal;

analysis means for frequency-analyzing the pulse wave detection signal and the body motion detection signal outputted from the pulse wave sensor;

body motion determination means for determining occurrence and nonoccurrence of body motion based on at least a detection signal from the pulse wave sensor or the result of analysis by the analysis means;

steady state determination means for, when the body motion determination means determines that body motion occurs, determining a steady state of the body motion based on a result of analysis by the analysis means; and pulse component extraction means for extracting the pulse component from the pulse wave detection signal, based on the result of analysis by the analysis means, a result of determination by the body motion determination means, and a result of determination by the steady state determination means, wherein the steady state determination means includes second steady state determination means for, when a highest peak frequency component and a second or third highest peak frequency component in the body motion detection signal are in relation of a fundamental wave to a second harmonic wave, determining the steady state of the body motion.

29. A portable biological information monitor apparatus which is adapted to be attached to a body of a test subject when it is used, comprising:

biological information detection means for repeatedly detecting biological information reflecting at least one of pulse, body motion, and autonomic nervous function of the test subject;

barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and storage means for storing the barometer generated by the barometer generation means, wherein the biological information detection means includes a biological status detection apparatus including:

a pulse wave sensor including a light emission unit to generate light being emitted to the test subject and a photoreception unit to receive reflected light from the test subject, wherein the pulse wave sensor outputs a pulse wave detection signal and a body motion detection signal, wherein the pulse wave detection signal includes a pulse component synchronized with pulse and a body motion component synchronized with body motion while the body motion detection signal includes the body motion component emphasized in comparison with the pulse wave detection signal;

analysis means for frequency-analyzing the pulse wave detection signal and the body motion detection signal outputted from the pulse wave sensor;

body motion determination means for determining occurrence and nonoccurrence of body motion based on at least a detection signal from the pulse wave sensor or the result of analysis by the analysis means;

steady state determination means for, when the body motion determination means determines that body motion occurs, determining a steady state of the body motion based on a result of analysis by the analysis means; and pulse component extraction means for extracting the pulse component from the pulse wave detection signal, based on the result of analysis by the analysis means, a result of determination by the body motion determination means, and a result of determination by the steady state determination means, wherein the pulse component extraction means includes first pulse component extraction means for, when nonoccurrence of body motion is determined by the body motion determination means, extracting a highest peak frequency component in the pulse wave detection signal as the pulse component.

30. A portable biological information monitor apparatus which is adapted to be attached to a body of a test subject when it is used, comprising:
biological information detection means for repeatedly detecting biological information reflecting at least one of pulse, body motion, and autonomic nervous function of the test subject;
barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and
storage means for storing the barometer generated by the barometer generation means,
wherein the biological information detection means includes a biological status detection apparatus including:
a pulse wave sensor including a light emission unit to generate light being emitted to the test subject and a photoreception unit to receive reflected light from the test subject, wherein the pulse wave sensor outputs a pulse wave detection signal and a body motion detection signal, wherein the pulse wave detection signal includes a pulse component synchronized with pulse and a body motion component synchronized with body motion while the body motion detection signal includes the body motion component emphasized in comparison with the pulse wave detection signal;
analysis means for frequency-analyzing the pulse wave detection signal and the body motion detection signal outputted from the pulse wave sensor;
body motion determination means for determining occurrence and nonoccurrence of body motion based on at least a detection signal from the pulse wave sensor or the result of analysis by the analysis means;
steady state determination means for, when the body motion determination means determines that body motion occurs, determining a steady state of the body motion based on a result of analysis by the analysis means; and
pulse component extraction means for extracting the pulse component from the pulse wave detection signal, based on the result of analysis by the analysis means, a result of determination by the body motion determination means, and a result of determination by the steady state determination means,
wherein the pulse component extraction means includes:
body motion component specifying means for, when the steady state of the body motion is determined by the steady state determination means, specifying a fundamental wave and a harmonic wave of the body motion component; and
second pulse component extraction means for, within the frequency area including the fundamental wave of the pulse component, an intensity ratio between a highest peak frequency component and a second highest peak frequency component in the pulse wave detection signal, except components corresponding to the fundamental wave and the harmonic wave specified by the body motion component specifying means, is higher than a predetermined ratio, extracting the highest peak frequency component as the pulse component.

31. The portable biological information monitor apparatus according to claim 30,
wherein the pulse component extraction means includes:
overlap estimation means for estimating existence and absence of overlap between the pulse component and the body motion component, based on the highest peak frequency component in the pulse wave detection signal within a preset search range including a frequency of a pulse component specified in previous measurement as a central frequency, and the fundamental wave and the harmonic wave of the body motion component specified by the body motion component specifying means; and
third pulse component extraction means for, when absence of overlap is estimated by the overlap estimation means, extracting the highest peak frequency component in the pulse wave detection signal within the search range as the pulse component.

32. The portable biological information monitor apparatus according to claim 31,
wherein the pulse component extraction means includes fourth pulse component extraction means for, when existence of overlap is estimated by the overlap estimation means, estimating a frequency component corresponding to the pulse component, from the result of analysis by the analysis means within a preset range including the highest peak frequency component in the pulse wave detection signal within the search range as a central component.

33. The portable biological information monitor apparatus according to claim 32,
wherein the fourth pulse component extraction means standardizes intensity of the result of analysis of the pulse wave detection signal and the body motion detection signal, and estimates a frequency component including a maximum intensity difference between the both signals as the pulse component.

34. The portable biological information monitor apparatus according to claim 32,
wherein the fourth pulse component extraction means calculates a correlation value between the result of analysis of the pulse wave detection signal and that of the body motion detection signal by a preset section, and estimates a frequency component including a maximum intensity in a section where the correlation value is minimum as the pulse component.

35. A portable biological information monitor apparatus which is adapted to be attached to a body of a test subject when it is used, comprising:
biological information detection means for repeatedly detecting biological information reflecting at least one of pulse, body motion, and autonomic nervous function of the test subject;
barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and storage means for storing the barometer generated by the barometer generation means, wherein the biological information detection means includes a biological status detection apparatus including:
- a pulse wave sensor including a light emission unit to generate light being emitted to the test subject and a photoreception unit to receive reflected light from the test subject, wherein the pulse wave sensor outputs a pulse wave detection signal and a body motion detection signal, wherein the pulse wave detection signal includes a pulse component synchronized with pulse and a body motion component synchronized with body motion while the body motion detection signal includes the body motion component emphasized in comparison with the pulse wave detection signal;
- analysis means for frequency-analyzing the pulse wave detection signal and the body motion detection signal outputted from the pulse wave sensor;
- body motion determination means for determining occurrence and nonoccurrence of body motion based on at least a detection signal from the pulse wave sensor or the result of analysis by the analysis means;
- steady state determination means for, when the body motion determination means determines that body motion occurs, determining a steady state of the body motion based on a result of analysis by the analysis means; and
- pulse component extraction means for extracting the pulse component from the pulse wave detection signal, based on the result of analysis by the analysis means, a result of determination by the body motion determination means, and a result of determination by the steady state determination means, wherein the biological status detection apparatus further includes barometer calculation means for calculating a barometer including at least one of a pulse rate and a pulse interval based on the pulse component extracted by the pulse component extraction means, wherein the barometer calculation means obtains a weighted mean frequency, based on frequency components of the pulse wave detection signal in a preset frequency range including the pulse component extracted by the pulse component extraction means as a central component, with intensity of frequency component as weight, and calculates the barometer from the weighted mean frequency.

36. A portable biological information monitor apparatus which is adapted to be attached to a body of a test subject when it is used, comprising:
- biological information detection means for repeatedly detecting biological information reflecting at least one of pulse, body motion, and autonomic nervous function of the test subject;
- barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and
- storage means for storing the barometer generated by the barometer generation means, wherein the biological information detection means includes a biological status detection apparatus including:
  - a pulse wave sensor including a light emission unit to generate light being emitted to the test subject and a photoreception unit to receive reflected light from the test subject, wherein the pulse wave sensor outputs a pulse wave detection signal and a body motion detection signal, wherein the pulse wave detection signal includes a pulse component synchronized with pulse and a body motion component synchronized with body motion while the body motion detection signal includes the body motion component emphasized in comparison with the pulse wave detection signal;
  - analysis means for frequency-analyzing the pulse wave detection signal and the body motion detection signal outputted from the pulse wave sensor;
  - body motion determination means for determining occurrence and nonoccurrence of body motion based on at least a detection signal from the pulse wave sensor or the result of analysis by the analysis means;
  - steady state determination means for, when the body motion determination means determines that body motion occurs, determining a steady state of the body motion based on a result of analysis by the analysis means; and
  - pulse component extraction means for extracting the pulse component from the pulse wave detection signal, based on the result of analysis by the analysis means, a result of determination by the body motion determination means, and a result of determination by the steady state determination means, wherein the biological status detection apparatus further includes light emission intensity control means for controlling light emission intensity in the light emission unit based on amplitude of the pulse wave detection signal outputted from the photoreception unit.

37. A portable biological information monitor apparatus which is adapted to be attached to a body of a test subject when it is used, comprising:
- biological information detection means for repeatedly detecting biological information reflecting at least one of pulse, body motion, and autonomic nervous function of the test subject;
- barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and
- storage means for storing the barometer generated by the barometer generation means, wherein the barometer generation means changes timing for generation of the barometer in accordance with the generation mode, wherein the biological information detection means includes a pulse wave detection apparatus including:
- light emission means for emitting light to the body;
- photoreception means for receiving at least reflected light of the light emitted from the light emission means;

a light transmitting plate provided to face a light emitting side of the light emission means for transmitting light; and a light shielding plate provided to cover a peripheral end of the light transmitting plate for blocking light, wherein a pulse wave of the body is detected by making contact between a skin of the body and an outer surface of the light transmitting plate and the light shielding plate, wherein the outer surface is opposite to a surface that faces the light emission means and the photoreception means, and wherein the light shielding plate restricts the photoreception means from receiving light emitted from outside of the pulse wave detection apparatus via the skin of the body, wherein a light shielding convex member is provided on the outer surface of the light shielding plate, the light shielding convex member adapted to cause a depressed portion in the skin when the pulse wave detection apparatus is fixed to the body's skin, and wherein the light shielding convex member is arranged in a transmission route of external light to reach the photoreception means through the skin to surround the light transmitting plate, thereby restricting the external light from being propagated inside the skin to the photoreception means.

38. The portable biological information monitor apparatus according to claim 37,
wherein a plurality of light shielding convex members are provided.

39. The portable biological information monitor apparatus according to claim 38,
wherein the plurality of light shielding convex members are arranged at random intervals.

40. The portable biological information monitor apparatus according to claim 37,
wherein each of the light shielding convex member is a projection line including a head end and a tail end.

41. The portable biological information monitor apparatus according to claim 37,
wherein the photoreception means outputs a photoreception signal corresponding to a photoreception amount of received light, and
wherein the pulse wave detection apparatus further includes:
amplifying means for amplifying the photoreception signal;
correcting means for outputting to the amplifying means a direct component signal corresponding to a direct current component included in the photoreception signal;
external light detection means for detecting external light that is emitted from outside of the pulse wave detection apparatus and received by the photoreception means, and for outputting to the correcting means an external light reception signal corresponding to a photoreception amount of the external light; and
pulse wave detection means for detecting the body's pulse wave based on the external light reception signal and the photoreception signal upon light emission by the light emission means.

42. The portable biological information monitor apparatus according to claim 41, wherein
the external light detection means is configured to use an A/D convener different from an A/D converter for detecting the external light reception signal.

43. The portable biological information monitor apparatus according to claim 41, wherein the correcting means for outputting to the amplifying means the direct component signal corresponding to a direct current component included in the photoreception signal uses an output signal from a D/A converter.

44. The portable biological information monitor apparatus according to claim 37, wherein
the light shielding plate and the light shielding convex member are formed by processing a casing of the pulse wave detection apparatus.

45. A portable biological information monitor apparatus which is adapted to be attached to a body of a test subject when it is used, comprising:
biological information detection means for repeatedly detecting biological information reflecting at least one of pulse, body motion, and autonomic nervous function of the test subject;
barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and
storage means for storing the barometer generated by the barometer generation means,
wherein the biological information detection means includes a pulse wave detection apparatus including:
light emission means for emitting light to the body;
photoreception means for receiving at least reflected light of the light emitted from the light emission means;
a light transmitting plate provided to face a light emitting side of the light emission means for transmitting light; and
a light shielding plate provided to cover a peripheral end of the light transmitting plate for blocking light,
wherein a pulse wave of the body is detected by making contact between a skin of the body and an outer surface of the light transmitting plate and the light shielding plate, wherein the outer surface is opposite to a surface that faces the light emission means and the photoreception means, and
wherein the light shielding plate restricts the photoreception means from receiving light emitted from outside of the pulse save detection apparatus via the skin of the body,
wherein a light shielding convex member is provided on the outer surface of the light shielding plate, the light shielding convex member being adapted to cause a depressed portion in the skin when the pulse wave detection apparatus is fixed to the body's skin,
wherein material of the light shielding convex member includes a flexible characteristic so as to bring the light shielding convex member into contact with the body's skin without gap when the pulse wave detection apparatus is fixed to the body's skin,
wherein the light shielding convex member is arranged to surround the light transmitting plate,
wherein each of the light shielding convex member is a projection line including a head end and a tail end,
wherein at least one light shielding convex member is provided on a line connecting a gap, formed between the ends of the line projection of light shielding convex member in a position most distant from the light transmitting plate, among the plurality of light shielding convex members, with the light transmitting plate.

46. A portable biological information monitor apparatus which is adapted to be attached to a body of a test subject when it is used, comprising:

biological information detection means for repeatedly detecting biological information reflecting at least one of pulse, body motion, and autonomic nervous function of the test subject;

barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means; and storage means for storing the barometer generated by the barometer generation means, wherein the barometer generation means changes timing for generation of the barometer in accordance with the generation mode, wherein the biological information detection means includes a pulse wave detection apparatus including:

light emission means for emitting light to the body;

photoreception means for receiving at least reflected light of the light emitted from the light emission means, and outputting a photoreception signal corresponding to a photoreception amount of the received light;

amplifying means for amplifying the photoreception signal;

correcting means for outputting to the amplifying means a direct component signal corresponding to a direct current component included in the photoreception signal;

external light detection means for detecting external light that is emitted from outside of the pulse wave detection apparatus and received by the photoreception means, and outputting to the correcting means an external light reception signal corresponding to a photoreception amount of the external light; and pulse wave detection means for detecting the body's pulse wave based on the external light reception signal and the photoreception signal upon light emission by the light emission means.

47. The portable biological information monitor apparatus according to claim 46, wherein the pulse wave detection means detects the pulse wave based on a differentiated signal obtained by differentiation of the external light reception signal outputted to the correcting means from the photoreception signal in the amplifying means.

48. The portable biological information monitor apparatus according to claim 46, wherein the external light detection means detects the external light when light emission by the light emission means is stopped.

49. The portable biological information monitor apparatus according to claim 48, wherein the light emission means emits light intermittently, and wherein the external light detection means detects the external light upon each stoppage of light emission by the light emission means.

50. The portable biological information monitor apparatus according to claim 46, wherein the correcting means for outputting to the amplifying means the direct component signal corresponding to a direct current component included in the photoreception signal uses an output signal from a D/A. converter.

51. The portable biological information monitor apparatus according to claim 46, wherein the external light detection means is configured to use an A/D converter different from an A/D converter for detecting the external light reception signal.

52. An information management apparatus comprising:

first communication means for performing communication with a portable biological information monitor apparatus that is adapted to be attached to a body of a test subject when it is used, wherein the portable biological information monitor apparatus includes, biological information detection means for repeatedly detecting biological information reflecting at least two of (i) pulse, (ii) body motion, and (iii) autonomic nervous function of the test subject, barometer generation means that has a plurality of generation modes corresponding to the test subject's actions and operates in any of the generation modes, wherein the generation modes include at least a first generation mode to generate a sleep evaluation barometer as a barometer for evaluation of a test subject's status in sleep based on the biological information detected by the biological information detection means and a second generation mode to generate a wake evaluation barometer as a barometer for evaluation of a test subject's status in wake based on the biological information detected by the biological information detection means, wherein the barometer generation means changes timing for generation of the barometer in accordance with the generation mode, wherein the barometer generation means changes a time interval for generation of the barometer in accordance with the generation mode, wherein the biological information detection means includes an optical pulse wave sensor to detect a pulse wave by utilizing a light absorbing characteristic of a blood component, storage means for storing the barometer generated by the barometer generation means, and second communication means for performing communication with the first communication means;

information accumulation means for accumulating information obtained from the portable biological information monitor apparatus via the first communication means;

evaluation means for evaluating the test subject's status based on the information accumulated in the information accumulation means; and display means for displaying at least one of the information accumulated in the information accumulation means and the result of evaluation by the evaluation means.

53. The information management apparatus according to claim 52, further comprising a remote controller, for controlling operation of the portable biological information monitor apparatus via the first communication means.

* * * * *